us 008202868B2

(12) United States Patent
Haupt et al.

(10) Patent No.: US 8,202,868 B2
(45) Date of Patent: Jun. 19, 2012

(54) 4-PIPERAZINYL-PYRIMIDINE COMPOUNDS SUITABLE FOR TREATING DISORDERS THAT RESPOND TO MODULATION OF THE DOPAMINE $D_3$ RECEPTOR

(75) Inventors: Andreas Haupt, Schwetzingen (DE); Liliane Unger, Ludwigshafen (DE); Karla Drescher, Dossenheim (DE); Ana Lucia Jongen-Relo, Hochdorf-Assenheim (DE); Roland Grandel, Dossenheim (DE); Wilfried Braje, Mannheim (DE); Herve Geneste, Neuhofen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 861 days.

(21) Appl. No.: 11/659,063

(22) PCT Filed: Aug. 8, 2005

(86) PCT No.: PCT/EP2005/008592
§ 371 (c)(1),
(2), (4) Date: Jun. 26, 2009

(87) PCT Pub. No.: WO2006/015842
PCT Pub. Date: Feb. 16, 2006

(65) Prior Publication Data
US 2009/0264437 A1    Oct. 22, 2009

Related U.S. Application Data

(60) Provisional application No. 60/600,042, filed on Aug. 9, 2004.

(51) Int. Cl.
C07D 417/12 (2006.01)
C07D 403/12 (2006.01)
A61K 31/505 (2006.01)

(52) U.S. Cl. ......... 514/252.02; 514/252.11; 514/252.18; 514/252.19; 544/238; 544/295; 544/296

(58) Field of Classification Search .................. 544/238, 544/295, 296; 514/252.02, 252.11, 252.14, 514/252.18, 252.19
See application file for complete search history.

(56) References Cited

U.S. PATENT DOCUMENTS
2008/0171751 A1 *   7/2008   Unger et al. ............. 514/252.19

FOREIGN PATENT DOCUMENTS

| WO | WO 96/02249 A1 | 7/1994 |
|---|---|---|
| WO | WO 9602246 A1 | 7/1994 |
| WO | WO 9602519 A1 | 7/1994 |
| WO | WO 9602520 A1 | 7/1994 |
| WO | WO 99/02503 | 7/1997 |
| WO | WO 00/42036 | 1/1999 |
| WO | WO 00/42037 | 1/1999 |
| WO | WO 00/42038 | 1/1999 |
| WO | WO 2004/080981 A1 | 3/2003 |

OTHER PUBLICATIONS

Le Foll et al., PubMed Abstract (Expert Opinion Investig Drugs, 16(1):45-57), Jan. 2007.*
Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
International Search Report in WO2006/015842A1 mailed on Oct. 24, 2005.
J.C. Schwartz et al., The Dopamine D3 Receptor as a Target for Antipsychotics, in Novel Antipsychotic Drugs, H.Y. Meltzer, Ed. Raven Press, New York 1992, pp. 135-144.
M. Dooley et al., Drugs and Aging 1998, 12, 495-514.
J.N. Joyce, Pharmacology and and Therapeutic Target for Antipsychotic and Antiparkinsonian Drugs, Pharmacology & Therapeutics 90(2001) 231-259.
P. Sokoloff et al., Localization and Function of the D3 Dopamine Receptor, Arzneium. Forsch./Drug Res. 42(1), 224 (1992).
P. Sokoloff et al. Molecular Cloning and Characterization of a Novel Dopamine Receptor (D3) as a Target for Neuroleptics, Nature, 347, 146 (1990).

* cited by examiner

*Primary Examiner* — Deepak Rao
(74) *Attorney, Agent, or Firm* — Lisa V. Mueller; Michael Best & Friedrich LLP

(57) ABSTRACT

The present invention relates to novel 4-piperazinylpyrimidine compounds. The compounds possess valuable therapeutic properties and are suitable, in particular, for treating diseases that respond to modulation of the dopamine $D_3$ receptor. The 4-piperzinylpyrimidine compounds have the general formula I

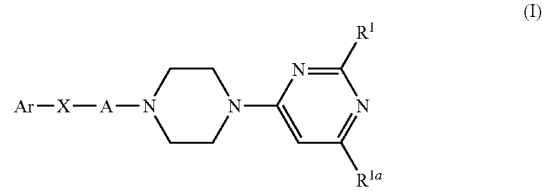

(I)

wherein Ar, X, A, $R^1$ and $R^{1a}$ are as defined in the claims.

27 Claims, No Drawings

4-PIPERAZINYL-PYRIMIDINE COMPOUNDS SUITABLE FOR TREATING DISORDERS THAT RESPOND TO MODULATION OF THE DOPAMINE D$_3$ RECEPTOR

This application is a 371 of PCT/EP2005/008592 filed Aug. 8, 2005 which claims the benefit of U.S. Provisional Application No. 60/600,042 filed Aug. 9, 2004.

BACKGROUND OF THE INVENTION

The present invention relates to novel 4-piperazinylpyrimidine compounds. The compounds possess valuable therapeutic properties and are suitable, in particular, for treating diseases that respond to modulation of the dopamine D$_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, namely the D$_1$ and D$_2$ receptors. More recently, a third subtype was found, namely the D$_3$ receptor which appears to mediate some effects of antipsychotics and antiparkinsonians (J. C. Schwartz et al., The Dopamine D$_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine D$_3$ Receptor as a Therapeutic Target for Antipsychotic and Antiparkinsonian Drugs").

Since then, the dopamine receptors have been divided into two families. On the one hand, there is the D$_2$ group, consisting of D$_2$, D$_3$ and D$_4$ receptors, and, on the other hand, the D$_1$ group, consisting of D$_1$ and D$_5$ receptors. Whereas D$_1$ and D$_2$ receptors are widely distributed, D$_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, D$_3$ receptors are regarded as being a target having few side-effects and it is assumed that while a selective D$_3$ ligand would have the properties of known antipsychotics, it would not have their dopamine D$_2$ receptor-mediated neurological side-effects (P. Sokoloff et al., Localization and Function of the D$_3$ Dopamine Receptor, Arzneim. Forsch./Drug Res. 4-2(1), 224 (1992); P. Sokoloff et al. Molecular Cloning and Characterization of a Novel Dopamine Receptor (D$_3$) as a Target for Neuroleptics, Nature, 347, 146 (1990)).

Pyrimidine compounds having an affinity for the dopamine D$_3$ receptor have been described in the prior art on various occasions, e.g. in WO 96/02519, WO 96/02520, WO 96/02249, WO 96/02246, WO 99/02503, WO 00/42036, WO 00/42037, WO 00/42038. Some of these compounds possess high affinities for the dopamine D$_3$ receptor. They have therefore been proposed as being suitable for treating diseases of the central nervous system. Unfortunately their selectivity towards the D$_3$ receptor or their pharmacological profile are not always satisfactory. Consequently there is an ongoing need to provide new compounds, which either have an improved selectivity or an improved pharmacological profile, e.g. a higher brain plasma ratio, a higher bioavailability or a decreased inhibition of the mitochondrial respiration.

SUMMARY OF THE INVENTION

The invention is based on the object of providing compounds which act as highly selective dopamine D$_3$ receptor ligands. This object is surprisingly achieved by means of 4-piperazinylpyrimidine compounds of the general formula I

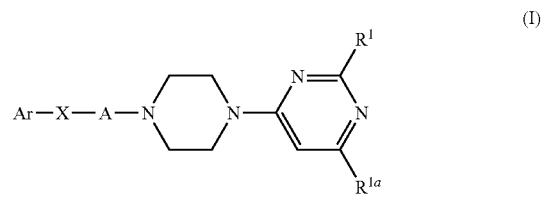

(I)

wherein

Ar is phenyl or an aromatic 5- or 6-membered C-bound heteroaromatic radical, comprising 1 nitrogen atom as ring member and 0, 1, 2 or 3 further heteroatoms, independently of each other, selected from O, S and N, as ring members, wherein Ar may carry 1, 2 or 3 radicals $R^a$ which are, independently of each other, selected from the group consisting of $C_1$-$C_6$ alkyl, $C_3$-$C_6$ cycloalkyl, $C_1$-$C_4$ alkoxy-$C_1$-$C_4$-alkyl, $C_1$-$C_4$ haloalkyl, CN, $NO_2$, halogen, $OR^2$, $NR^3R^4$, $C(O)NR^3R^4$, O—$C(O)NR^3R^4$, $SO_2NR^3R^4$, $COOR^5$, $SR^6$, $SOR^6$, $SO_2R^6$, O—$C(O)R^7$, $COR^7$ or $C_3$-$C_5$ cycloalkylmethyl, wherein Ar may also carry a phenyl group or an aromatic 5- or 6-membered C-bound heteroaromatic radical, comprising 1 nitrogen atom as ring member and 0, 1, 2 or 3 further heteroatoms, independently of each other, selected from O, S and N, wherein the last two mentioned radicals may carry 1, 2, 3 or 4 of the aforementioned radicals $R^a$;

X is a single bond, $CONR^8$, S, or O;

A is linear $C_3$-$C_4$ alkylene, which may carry 1 or 2 $C_1$-$C_4$-alkyl groups;

$R^1$, $R^{1a}$ are independently from each other selected from $C_3$-$C_6$ alkyl, $C_1$-$C_2$-fluoroalkyl, or $C_3$-$C_6$ cycloalkyl, which may carry 1 or 2 $C_1$-$C_4$ alkyl groups, provided that at least one of the radicals $R^1$, $R^{1a}$ is selected from $C_3$-$C_4$ cycloalkyl optionally substituted with a $C_1$-$C_4$ alkyl group;

$R^2$, $R^3$, $R^4$, $R^5$, $R^6$, and $R^7$ independent of each other are H, $C_1$-$C_6$ alkyl, optionally substituted with OH, $C_1$-$C_4$ alkoxy or phenyl, $C_1$-$C_4$ haloalkyl or phenyl, which may carry 1, 2 or 3 radicals selected from the group consisting of $C_1$-$C_6$ alkyl, $C_1$-$C_6$ alkoxy, $NR^3R^4$, CN, $C_1$-$C_2$ fluoroalkyl oder halogen, $R^4$ may also be a radical $COR^9$, wherein $R^9$ is hydrogen, $C_1$-$C_6$ alkyl, $C_1$-$C_6$ alkoxy or phenyl, which may carry 1, 2 or 3 radicals selected from the group consisting of $C_1$-$C_6$ alkyl, $C_1$-$C_6$ alkoxy, $NR^3R^4$, CN, $C_1$-$C_2$ fluoroalkyl oder halogen, $R^3$ and $R^4$ may together with the nitrogen atom to which they are bound form a N-bound 5 or 6 membered saturated heterocyle, which may comprise an oxygen atom or an additional nitrogen atom as a ring member and which may carry 1, 2, 3 or 4 $C_1$-$C_6$ alkyl groups; and $R^8$ is hydrogen or $C_1$-$C_4$ alkyl;

their tautomers and the physiologically tolerated acid addition salts of these compounds and of the tautomers.

The present invention therefore relates to 4-piperazinylpyrimidine compounds of the general formula I and to their physiologically tolerated acid addition salts.

The present invention also relates to a pharmaceutical composition which comprises at least one 4-piperazinylpyrimidine compound of the formula I and/or at least one physiologically tolerated acid addition salt of I, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one 4-piperazinylpyrimidine compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include, in particular, disorders and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the above mentioned indications. Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine.

$C_1$-$C_4$ Alkyl is a straight-chain or branched alkyl group having from 1 to 4 carbon atoms. Examples of an alkyl group are methyl, ethyl, n-propyl, isopropyl, n-butyl, 2-butyl, isobutyl or tert-butyl.

$C_1$-$C_6$ Alkyl is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Branched $C_3$-$C_6$ alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl 1-methyl-1-ethylpropyl.

$C_1$-$C_6$-Haloalkyl refers to a straight-chain or branched saturated alkyl group having 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

$C_1$-$C_2$ Fluoroalkyl is an alkyl group having 1 or 2 C atoms in which all or some, e.g. 1, 2, 3 or 4 of the hydrogen atoms, is/are replaced by fluorine atoms. Examples are $CF_3$, $CHF_2$, $CH_2F$ or $CH_2CF_3$.

$C_1$-$C_4$ Alkoxy is a straight-chain or branched alkyl group having from 1 to 4 carbon atoms, which is bound to the remainder of the molecule via an oxygen atom. Examples of $C_1$-$C_4$ alkoxy are methoxy, ethoxy, n-propoxy, isopropoxy, n-butoxy, 2-butoxy, iso-butoxy and tert.-butoxy.

$C_1$-$C_6$ Alkoxy is a straight-chain or branched alkyl group having from 1 to 6 carbon atoms, which is bound to the remainder of the molecule via an oxygen atom. Examples include $C_1$-$C_4$ alkoxy as mentioned above and also pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy;

$C_1$-$C_4$ Alkoxy-$C_1$-$C_4$-alkyl, is a $C_1$-$C_4$-alkyl group, as mentioned above, in particular a methyl or an ethyl group, which carries a $C_1$-$C_4$-alkoxy substituent, e.g. methoxymethyl, ethoxymethyl, n-propoxymethyl, isopropoxymethyl, n-butoxymethyl, (1-methyl-propoxy)methyl, (2-methylpropoxy)methyl, 1-methoxyethyl, 1-ethoxyethyl, 1-(n-propoxy)ethyl, 1-isopropoxyethyl, 1-(n-butoxy)ethyl, 1-(1-methylpropoxy)ethyl, 1-(2-methylpropoxy)methyl, 2-methoxyethyl, 2-ethoxyethyl, 2-(n-propoxy)ethyl, 2-isopropoxyethyl, 2-(n-butoxy)ethyl, 2-(1-methylpropoxy)ethyl or 2-(2-methylpropoxy)methyl.

$C_3$-$C_6$ Cycloalkyl is a cycloaliphatic radical having from 3 to 6 C atoms, such as cyclopropyl, cyclobutyl and cyclopentyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl.

Linear $C_3$-$C_4$-alkylene is 1,3-propandiyl or 1,4-butandiyl, which may carry 1 or 2 $C_1$-$C_4$-alkyl groups, especially 1 or 2 methyl groups such as in 2-methylbut-2-en-1,4-diyl, (R)- and (S)-2-methylpropan-1,3-diyl, (R)- and (S)-butan-1,3-diyl, (R)- and (S)-butan-2,4-diyl, (R)- and (S)-2-methylbutan-1,4-diyl, (R)- and (S)-pentan-1,4-diyl, (R)- and (S)-pentan-2,5-diyl, (R)- and (S)-pentan-1,3-diyl, pentan-2,4-diyl, (R)- and (S)-2-(R)-methylbutan-1,3-diyl, (R)- and (S)-2-(S)-methylbutan-1,3-diyl, etc.

Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furyl, 2- or 3-pyrrolyl, 2-, 3- or 5-oxazolyl, 3-, 4- or 5-isoxazolyl, 2-, 3- or 5-thiazolyl, 3-, 4- or 5-isothiazolyl, 1-thia-3,4-diazolyl, 1H-, 2H- or 3H-1,2,3-triazol-4-yl, 2H-triazol-3-yl, 1H-, 2H-, or 4H-1,2,4-triazolyl and 1H- or 2H-tetrazolyl, which may be unsubstituted or which may carry 1, 2 or 3 of the aforementioned radicals $R^a$.

Preferred heteroaromatic radicals Ar are of the following formulae a to k:

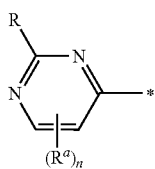

(a)

(b)

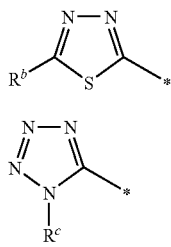

(c)

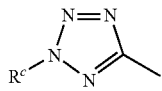

(d)

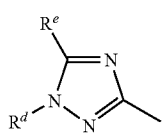

(e)

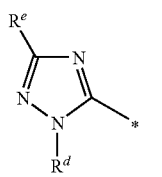

(f)

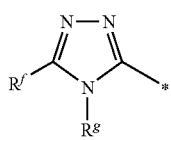

(g)

(h)

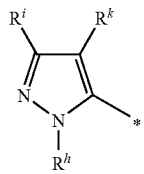

(i)

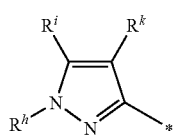

(k)

The * indicates in formulae a to k indicates the position at which Ar is connected with X. In formulae a and b the variable n is 0 or 1 and the radicals $R^a$ and R are as defined above for formula I. In formulae c to k the radicals $R^b$, $R^c$, $R^d$, $R^e$, $R^f$, $R^g$, $R^h$, $R^i$ and $R^k$ have the following meanings:

R is hydrogen, OH or halogen, especially fluorine, and preferably OH;

$R^b$, $R^e$, $R^f$, $R^i$, $R^k$ are each independently hydrogen or a radical $R^a$, as defined above or $R^e$ and $R^f$ may also be phenyl or a 5- or 6-membered heteroaromatic radical such as 2-, 3-, or 4-pyridyl, 2-, 4- or 5-pyrimidinyl, pyrazinyl, 3- or 4-pyridazinyl, 2- or 3-thienyl, 2- or 3-furyl, 2- or 3-pyrrolyl, 2-, 3- or 5-oxazolyl, 3-, 4- or 5-isoxazolyl, 2-, 3- or 5-thiazolyl, 3-, 4- or 5-isothiazolyl, 1-thia-3,4-diazolyl, 1H-, 2H- or 3H-1,2,3-triazol-4-yl, 2H-triazol-3-yl, 1H-, 2H-, or 4H-1,2,4-triazolyl and 1H- or 2H-tetrazolyl, which may be unsubstituted or which may carry 1, 2 or 3 of the aforementioned radicals $R^a$; in particular 1, 2 or 3 of the radicals selected from halogen, $C_1$-$C_4$ alkyl, especially methyl, $C_1$-$C_2$ fluoroalkyl, especially difluoromethyl or trifluoromethyl.

$R^c$, $R^d$, $R^g$, $R^h$ are each independently hydrogen, $C_1$-$C_4$ alkyl, especially methyl, $C_3$-$C_6$ cycloalkyl, especially cyclopropyl or cylobutyl, $C_1$-$C_4$-alkoxymethyl, $C_1$-$C_2$ fluoroalkyl, especially difluoromethyl or trifluoromethyl.

Preferred radicals $R^a$ are selected from the group consisting of halogen, especially, $NR^3R^4$, OH, SH, $C_1$-$C_4$ alkyl, $C_1$-$C_4$ alkoxy, $C_1$-$C_4$ thioalkyl, $C_3$-$C_5$ cycloalkyl, $C_1$-$C_4$ alkoxymethyl and $C_1$-$C_2$-fluoroalkyl.

In formula a the radical $R^a$ is more preferably hydrogen.

In formula b the radical $R^a$ is more preferably hydrogen, fluorine or methyl.

More preferably $R^c$, $R^d$, $R^g$ are each independently $C_1$-$C_4$ alkyl, especially methyl. $R^h$ is preferably $C_1$-$C_4$ alkyl, especially methyl, or cyclopropyl.

More preferably $R^b$, $R^e$, $R^f$, $R^i$, $R^k$ are each independently selected from the group consisting of $NR^3R^4$, OH, SH, $C_1$-$C_4$ alkyl, $C_3$-$C_5$ cycloalkyl, $C_1$-$C_4$ alkoxymethyl and $C_1$-$C_2$-fluoroalkyl, $R^e$ and $R^f$ may also be phenyl, 2- or 3-pyrrolyl, 2-, 3-, or 4-pyridyl, 2-, 4- or 5-pyrimidinyl, pyrazinyl, 3- or 4-pyridazinyl, which may be unsubstituted or which may carry 1, 2 or 3 of the aforementioned radicals $R^a$; in particular 1, 2 or 3 of the radicals selected from halogen, $C_1$-$C_4$ alkyl, especially methyl, $C_1$-$C_2$ fluoroalkyl, especially difluoromethyl or trifluoromethyl.

$R^b$ is most preferably hydrogen or $C_1$-$C_4$ alkyl, especially hydrogen or methyl.

$R^e$ is most preferably hydrogen or $C_1$-$C_4$ alkyl, especially hydrogen or methyl, phenyl or pyrazinyl.

$R^f$ is most preferably hydrogen, $C_1$-$C_4$ alkyl, especially methyl, $C_3$-$C_5$ cycloalkyl, especially cyclopropyl or cyclobutyl, $C_1$-$C_4$ alkoxymethyl, especially methoxymethyl or ethoxymethyl, trifluoromethyl, phenyl or pyrazinyl.

$R^i$ is most preferably hydrogen or $C_1$-$C_4$ alkyl, especially hydrogen or methyl.

$R^k$ is preferably hydrogen.

With a view to the use of the compounds according to the invention as dopamine $D_3$ receptor ligands, preference is given to those compounds of formula I in which the radical Ar is a radical of formulae a, b, or h.

With a view to the use of the compounds according to the invention as dopamine $D_3$ receptor ligands, preference is given to those compounds of formula I in which the radical $R^1$ is selected from tert.-butyl, trifluoromethyl, cyclopropyl, cyclobutyl or cyclopentyl. $R^1$ is most preferably tert. butyl. $R^{1a}$ is preferably selected from cyclopropyl, cyclobutyl and 1-methylcyclopropyl.

With a view to the use of the compounds according to the invention as dopamine $D_3$ receptor ligands, preference is also given to those compounds of formula I in which the radical $R^{1a}$ is selected from tert.-butyl, trifluoromethyl, cyclopropyl, cyclobutyl and cyclopentyl with most preference given to tert. butyl. $R^1$ is preferably selected from cyclopropyl, cyclobutyl and 1-methylcyclopropyl.

In a first embodiment of the invention X is a single bond, an oxygen atom or a sulfur atom. Amongst these compounds preference is given to those compounds of formula I in which X and A form a 4-membered chain, i.e. the group Ar is separated from the piperazin nitrogen to which A is bound by 4 atoms. In other words, when X is a single bond, A is preferably butan-1,4-diyl, which may carry 1 or 2 methyl groups, and especially butan-1,4-diyl. When X is O or S, A is preferably propan-1,3-diyl, (R)- or (S)-2-methylpropan-1,3-diyl, (R)- or (S)-butan-1,3-diyl, (R)- or (S)-butan-2,4-diyl.

In this first embodiment, preference is given to compounds of the formula I, wherein Ar is a C-bound heteroaromatic radical and more preferably a radical of the formulae a to m as defined above.

Amongst the compounds of the first embodiment more preference is given to those compounds of the formula I, wherein Ar is 2- or 4-pyrimidinyl, which may carry 1, 2 or 3, preferably 1 or 2 of the aforementioned radicals $R^a$. Amongst these compounds preference is given to those, which carry an OH group either in the 4-/6-position or in the 2-position of the pyrimidine radical. An especially preferred embodiment of the invention relates to compounds of the formula I, wherein Ar is 2-hydroxypyrimidin-4-yl or 4-hydroxypyrimidin-2-yl.

Amongst these compounds, those of the formulae Ia and Ib, the tautomers, enantiomers and diastereomers of Ia or Ib and the physiologically tolerated acid addition salts of these compounds and of the enantiomers, diastereomers and tautomers are especially preferred:

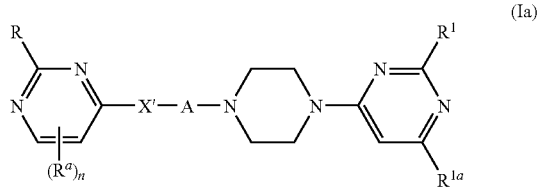

(Ia)

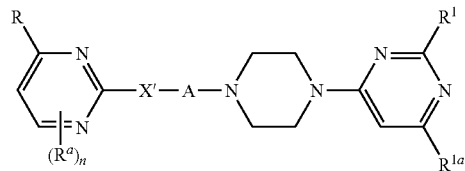

(Ib)

In formulae Ia and Ib n, R, $R^1$, $R^{1a}$ and $R^a$ are as defined above. The variables A and X have the following meanings:
A is propane-1,3-diyl or 2-methylpropane-1,3-diyl
X' is $CH_2$, O or S.

In formulae Ia R is preferably OH. Preferably n in formula Ia is 0 or 1 and especially 0.

If n=1, $R^a$ in formula Ib is preferably fluorine or methyl.

Preferred examples of compounds of the formula Ia comprise
2-tert-Butyl-4-cyclobutyl-6-{4-[3-(pyrimidin-4-yloxy)propyl]-piperazin-1-yl}pyrimidine;
4-{3-[4-(2-tert-Butyl-6-cyclobutylpyrimidin-4-yl)piperazin-1-yl]propoxy}pyrimidin-2-ol;
4-{3-[4-(2-tert-Butyl-6-cyclobutylpyrimidin-4-yl)piperazin-1-yl]butyl}pyrimidin-2-ol;
(R)-4-{3-[4-(2-tert-Butyl-6-cyclobutylpyrimidin-4-yl)piperazin-1-yl]-2-methylpropoxy}pyrimidin-2-ol;
(S)-4-{3-[4-(2-tert-Butyl-6-cyclobutylpyrimidin-4-yl)piperazin-1-yl]-2-methylpropoxy}pyrimidin-2-ol;
2-tert-Butyl-4-cyclopropyl-6-{4-[3-(pyrimidin-4-yloxy)propyl]-piperazin-1-yl}pyrimidine;
4-{3-[4-(2-tert-Butyl-6-cyclopropylpyrimidin-4-yl)piperazin-1-yl]propoxy}pyrimidin-2-ol;
4-{3-[4-(2-tert-Butyl-6-cyclopropylpyrimidin-4-yl)piperazin-1-yl]butyl}pyrimidin-2-ol;
(R)-4-{3-[4-(2-tert-Butyl-6-cyclopropylpyrimidin-4-yl)piperazin-1-yl]-2-methyl-propoxy}pyrimidin-2-ol;
(S)-4-{3-[4-(2-tert-Butyl-6-cyclopropylpyrimidin-4-yl)piperazin-1-yl]-2-methyl-propoxy}pyrimidin-2-ol;
their tautomers, enantiomers and diastereomers, and the physiologically tolerated acid addition salts of these compounds and the enantiomers, diastereomers and tautomers thereof.

Preferred examples of compounds of the formula Ib comprise
2-{3-[4-(2-tert-Butyl-6-cyclobutylpyrimidin-4-yl)piperazin-1-yl]propylsulfanyl}pyrimidin-4-ol fumarate,
2-tert-Butyl-4-cyclobutyl-6-{4-[3-(pyrimidin-2-ylsulfanyl)propyl]-piperazin-1-yl}pyrimidine,
2-tert-Butyl-4-cyclobutyl-6-{4-[3-(4-methylpyrimidin-2-ylsulfanyl)propyl]-piperazin-1-yl}pyrimidine,
2-{3-[4-(2-tert-Butyl-6-cyclobutylpyrimidin-4-yl)piperazin-1-yl]propoxy}pyrimidin-4-ol,
2-tert-Butyl-4-cyclobutyl-6-{4-[3-(pyrimidin-2-yloxy)propyl]-piperazin-1-yl}pyrimidine,
(R)-2-tert-Butyl-4-cyclobutyl-6-{4-[2-methyl-3-(pyrimidin-2-yloxy)propyl]-piperazin-1-yl}pyrimidine,
(S)-2-tert-Butyl-4-cyclobutyl-6-{4-[2-methyl-3-(pyrimidin-2-yloxy)propyl]-piperazin-1-yl}pyrimidine,
2-{4-[4-(2-tert-Butyl-6-cyclobutylpyrimidin-4-yl)piperazin-1-yl]butyl}pyrimidin-4-ol,
2-{3-[4-(2-tert-Butyl-6-cyclopropylpyrimidin-4-yl)piperazin-1-yl]propoxy}pyrimidin-4-ol,
2-{3-[4-(2-tert-Butyl-6-cyclopropylpyrimidin-4-yl)piperazin-1-yl]propylsulfanyl}pyrimidin-4-ol fumarate,
2-tert-Butyl-4-cyclopropyl-6-{4-[3-(pyrimidin-2-ylsulfanyl)propyl]-piperazin-1-yl}pyrimidine, 2-tert-Butyl-4-cyclopropyl-6-{4-[3-(4-methylpyrimidin-2-ylsulfanyl)propyl]-piperazin-1-yl}pyrimidine,
2-{3-[4-(2-tert-Butyl-6-cyclopropylpyrimidin-4-yl)piperazin-1-yl]propoxy}pyrimidin-4-ol,
2-tert-Butyl-4-cyclopropyl-6-{4-[3-(pyrimidin-2-yloxy)propyl]-piperazin-1-yl}pyrimidine,
(R)-2-tert-Butyl-4-cyclopropyl-6-{4-[2-methyl-3-(pyrimidin-2-yloxy)propyl]-piperazin-1-yl}pyrimidine,
(S)-2-tert-Butyl-4-cyclopropyl-6-{4-[2-methyl-3-(pyrimidin-2-yloxy)propyl]-piperazin-1-yl}pyrimidine,
2-{4-[4-(2-tert-Butyl-6-cyclopropylpyrimidin-4-yl)piperazin-1-yl]butyl}pyrimidin-4-ol,
2-{3-[4-(2-tert-Butyl-6-cyclopropylpyrimidin-4-yl)piperazin-1-yl]propoxy}pyrimidin-4-ol,
2-tert-Butyl-4-cyclopropyl-6-{4-[3-(pyrimidin-2-ylsulfanyl)propyl]-piperazin-1-yl}pyrimidine,
2-tert-Butyl-4-cyclobutyl-6-{4-[3-(5-fluoropydmidin-2-ylsulfanyl)propyl]-piperazin-1-yl}pyrimidine,
2-tert-Butyl-4-cyclobutyl-6-{4-[3-(5-fluoropyrimidin-2-yloxy)propyl]-piperazin-1-yl}pyrimidine,
(R)-2-tert-Butyl-4-cyclobutyl-6-{4-[2-methyl-3-(5-fluoropyrimidin-2-yloxy)propyl]-piperazin-1-yl}pyrimidine,
(S)-2-tert-Butyl-4-cyclobutyl-6-{4-[2-methyl-3-(5-fluoropyrimidin-2-yloxy)propyl]-piperazin-1-yl}pyrimidine,
2-tert-Butyl-4-cyclopropyl-6-{4-[3-(5-fluoropyrimidin-2-ylsulfanyl)propyl]-piperazin-1-yl}pyrimidine,
2-tert-Butyl-4-cyclopropyl-6-{4-[3-(5-fluoropyrimidin-2-yloxy)propyl]-piperazin-1-yl}pyrimidine,
(R)-2-tert-Butyl-4-cyclopropyl-6-{4-[2-methyl-3-(5-fluoropyrimidin-2-yloxy)propyl]-piperazin-1-yl}pyrimidine,
(S)-2-tert-Butyl-4-cyclopropyl-6-{4-[2-methyl-3-(5-fluoropyrimidin-2-yloxy)propyl]-piperazin-1-yl}pyrimidine,
their tautomers, enantiomers and diastereomers, and the physiologically tolerated acid addition salts of these compounds and the enantiomers, diastereomers and tautomers thereof.

Amongst these compounds, those of the formulae Ic, Id, Ie, If, Ig, Ii, Ih and Ik, their diastereomers, enantiomers and tautomers as well as the physiologically tolerated acid addition salts of these compounds are especially preferred:

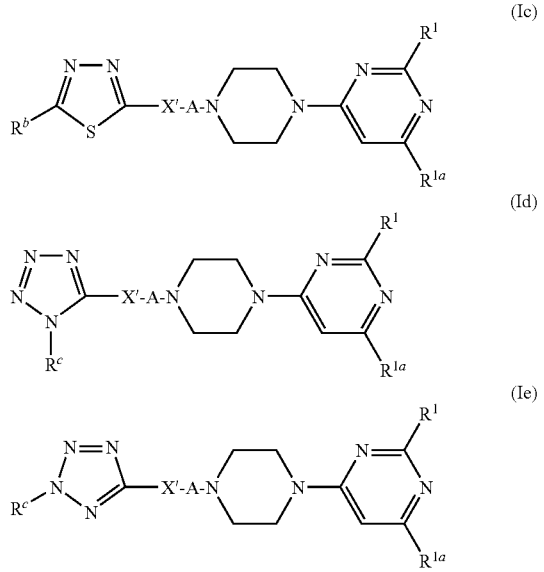

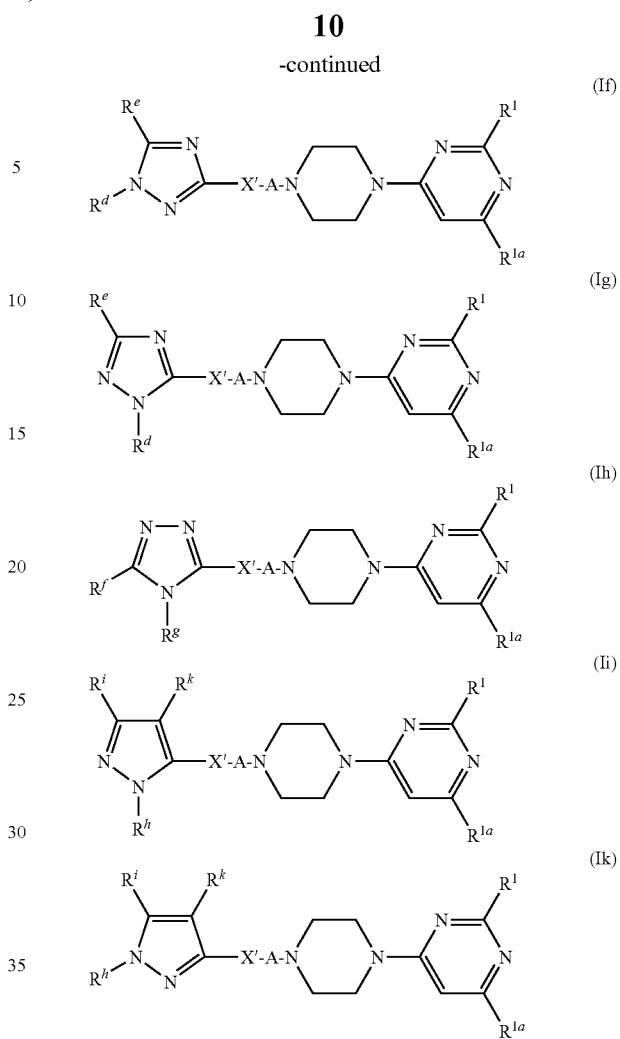

In formulae Ic, Id, Ie, If, Ig, Ih, Ii and Ik $R^1$ and $R^{1a}$ are as defined above. The variables $R^b$, $R^c$, $R^d$, $R^e$, $R^f$, $R^g$, $R^h$; $R^i$, $R^k$ have the meanings given for formulae a to k. A and X' have the following meanings:
A is propane-1,3-diyl or 2-methylpropane-1,3-diyl; and
X' is $CH_2$, O or S.

Preferred examples of compounds of the formula Ic comprise
2-tert-Butyl-4-{4-[3-(5-methyl-[1,3,4]-thiadiazol-2-ylsulfanyl)-propyl]-piperazin-1-yl}-6-cyclobutyl-pyrimidine,
2-tert-Butyl-4-{4-[3-(5-methyl-[1,3,4]-thiadiazol-2-ylsulfanyl)-propyl]-piperazin-1-yl}-6-cyclopropyl-pyrimidine,
2-tert-Butyl-4-{4-[3-(1,3,4-thiadiazol-2-ylsulfanyl)-propyl]-piperazin-1-yl}-6-cyclobutyl-pyrimidine,
2-tert-Butyl-4-{4-[3-(1,3,4-thiadiazol-2-ylsulfanyl)-propyl]-piperazin-1-yl}-6-cyclopropyl-pyrimidine,
2-tert-Butyl-4-{4-[3-(5-methyl-[1,3,4]-thiadiazol-2-yloxy)-propyl]-piperazin-1-yl}-6-cyclobutyl-pyrimidine,
2-tert-Butyl-4-{4-[3-(5-methyl-[1,3,4]-thiadiazol-2-yloxy)-propyl]-piperazin-1-yl}-6-cyclopropyl-pyrimidine,
2-tert-Butyl-4-{4-[3-(1,3,4-thiadiazol-2-yloxy)-propyl]-piperazin-1-yl}-6-cyclobutyl-pyrimidine,
2-tert-Butyl-4-{4-[3-(1,3,4-thiadiazol-2-yloxy)propyl]-piperazin-1-yl}-6-cyclopropyl-pyrimidine,
their tautomers, enantiomers and diastereomers, and the physiologically tolerated acid addition salts of these compounds and the enantiomers, diastereomers and tautomers thereof.

Preferred examples of compounds of the formula Id comprise 2-tert-Butyl-4-{4-[3-(1-methyl-1H-tetrazol-5-ylsulfanyl)-propyl]-piperazin-1-yl}-6-cyclobutyl-pyrimidine,
2-tert-Butyl-4-{4-[3-(1-methyl-1H-tetrazol-5-ylsulfanyl)-propyl]-piperazin-1-yl}-6-cyclopropyl-pyrimidine,
2-tert-Butyl-4-{4-[3-(1-methyl-1H-tetrazol-5-yloxy)-propyl]-piperazin-1-yl}-6-cyclobutyl-pyrimidine,
2-tert-Butyl-4-{4-[3-(1-methyl-1H-tetrazol-5-yloxy)-propyl]-piperazin-1-yl}-6-cyclopropyl-pyrimidine, their tautomers, enantiomers and diastereomers, and the physiologically tolerated acid addition salts of these compounds and the enantiomers, diastereomers and tautomers thereof.

Preferred examples of compounds of the formula Ie comprise 2-tert-Butyl-4-{4-[3-(2-methyl-2H-tetrazol-5-ylsulfanyl)-propyl]-piperazin-1-yl}-6-cyclobutyl-pyrimidine,
2-tert-Butyl-4-{4-[3-(2-methyl-2H-tetrazol-5-ylsulfanyl)-propyl]-piperazin-1-yl}-6-cyclopropyl-pyrimidine,
2-tert-Butyl-4-{4-[3-(2-methyl-2H-tetrazol-5-yloxy)-propyl]-piperazin-1-yl}-6-cyclobutyl-pyrimidine,
2-tert-Butyl-4-{4-[3-(2-methyl-2H-tetrazol-5-yloxy)-propyl]-piperazin-1-yl}-6-cyclopropyl-pyrimidine, their tautomers, enantiomers and diastereomers, and the physiologically tolerated acid addition salts of these compounds and the enantiomers, diastereomers and tautomers thereof.

Preferred examples of compounds of the formula If comprise 2-tert-Butyl-4-{4-[3-(1-methyl-1H-[1,2,4]triazol-3-ylsulfanyl)-propyl]-piperazin-1-yl}-6-cyclopropyl-pyrimidine,
2-tert-Butyl-4-{4-[3-(1-methyl-1H-[1,2,4]triazol-3-ylsulfanyl)-propyl]-piperazin-1-yl}-6-cyclobutyl-pyrimidine,
2-tert-Butyl-4-{4-[3-(1-methyl-1H-[1,2,4]triazol-3-yloxy)-propyl]-piperazin-1-yl}-6-cyclobutyl-pyrimidine,
2-tert-Butyl-4-{4-[3-(1-methyl-1H-[1,2,4]triazol-3-yloxy)-propyl]-piperazin-1-yl}-6-cyclopropyl-pyrimidine,
2-tert-Butyl-4-cyclobutyl-6-{4-[3-(1H-[1,2,4]triazol-3-ylsulfanyl)-propyl]-piperazin-1-yl}-pyrimidine, their tautomers, enantiomers and diastereomers, and the physiologically tolerated acid addition salts of these compounds and the enantiomers, diastereomers and tautomers thereof.

Preferred examples of compounds of the formula Ig comprise 2-tert-Butyl-4-{4-[3-(2-methyl-2H-[1,2,4]triazol-3-ylsulfanyl)-propyl]-piperazin-1-yl}-6-cyclopropyl-pyrimidine,
2-tert-Butyl-4-{4-[3-(2-methyl-2H-[1,2,4]triazol-3-ylsulfanyl)-propyl]-piperazin-1-yl}-6-cyclobutyl-pyrimidine,
2-tert-Butyl-4-{4-[3-(2-methyl-2H-[1,2,4]triazol-3-yloxy)-propyl]-piperazin-1-yl}-6-cyclobutyl-pyrimidine,
2-tert-Butyl-4-{4-[3-(2-methyl-2H-[1,2,4]triazol-3-yloxy)-propyl]-piperazin-1-yl}-6-cyclopropyl-pyrimidine, their tautomers, enantiomers and diastereomers, and the physiologically tolerated acid addition salts of these compounds and the enantiomers, diastereomers and tautomers thereof.

Preferred examples of compounds of the formula Ih comprise 2-tert-Butyl-4-{4-[3-(4-methyl-5-methyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-ethyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-propyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-tert-butyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-trifluoromethyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-methyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-ethyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-propyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-tert-butyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-trifluoromethyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-methyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-ethyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-propyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-tert-butyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-trifluoromethyl-4H-[1,2,4]triazol-3-ylsulfanyl)-propyl]-piperazin-1-yl}-6-cyclobutyl-pyrimidine,
2-tert-Butyl-4-{4-[3-(4-methyl-4H-[1,2,4]triazol-3-ylsulfanyl)-propyl]-piperazin-1-yl}-6-(1-methylcyclobutyl)-pyrimidine,
2-tert-Butyl-4-{4-[3-(4-methyl-5-methyl-4H-[1,2,4]triazol-3-ylsulfanyl)-propyl]-piperazin-1-yl}-6-(1-methylcyclobutyl)-pyrimidine,
2-tert-Butyl-4-{4-[3-(4-methyl-5-trifluoromethyl-4H-[1,2,4]triazol-3-ylsulfanyl)-propyl]-piperazin-1-yl}-6-(1-methylcyclobutyl)-pyrimidine,
2-tert-Butyl-4-{4-[3-(4-methyl-4H-[1,2,4]triazol-3-ylsulfanyl)-propyl]-piperazin-1-yl}-6-cyclobutyl-pyrimidine,
2-tert-Butyl-4-{4-[3-(4-methyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-cyclopropyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-cyclopropyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-cyclobutyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-methoxymethyl-4H-[1,2,4]triazol-3-ylsulfanyl)-propyl]-piperazin-1-yl}-6-cyclopropyl-pyrimidine, 2-tert-Butyl-4-{4-[3-(4-methyl-5-methoxymethyl-4H-[1,2,4]triazol-3-ylsulfanyl)-propyl]-piperazin-1-yl}-6-cyclobutyl-pyrimidine,
2-tert-Butyl-4-{4-[3-(4H-[1,2,4]triazol-3-ylsulfanyl)-propyl]-piperazin-1-yl}-6-cyclobutyl-pyrimidine,
2-tert-butyl-4-{4-[3-(4-methyl-4H-[1,2,4]triazol-3-yloxy)propyl]-piperazin-1-yl}-6-cyclobutyl-pyrimidine,
2-cyclopropyl-4-{4-[3-(4-methyl-4H-[1,2,4]triazol-3-ylsulfanyl)-propyl]-piperazin-1-yl}-6-tert-butyl-pyrimidine,
2-cyclopropyl-4-{4-[3-(4,5-dimethyl-4H-[1,2,4]triazol-3-ylsulfanyl)-propyl]-piperazin-1-yl}-6-tert-butyl-pyrimidine,
2-cyclobutyl-4-{4-[3-(4-methyl-4H-[1,2,4]triazol-3-ylsulfanyl)-propyl]-piperazin-1-yl}-6-tert-butyl-pyrimidine,
2-(1-methyl-cyclopropyl)-4-{4-[3-(4-methyl-4H-[1,2,4]triazol-3-ylsulfanyl)-propyl]-piperazin-1-yl}-6-tert-butyl-pyrimidine,
2-tert-butyl-4-{4-[3-(5-pyrazin-4-methyl-4H-[1,2,4]triazol-3-ylsulfanyl)-propyl]-piperazin-1-yl}-6-cyclopropyl-pyrimidine,
2-tert-butyl-4-{4-[3-(5-(1-methylpyrrol-2-yl)-4-methyl-4H-[1,2,4]triazol-3-ylsulfanyl)-propyl]-piperazin-1-yl}-6-cyclopropyl-pyrimidine,
2-tert-butyl-4-{4-[3-(5-(1-methylpyrrol-3-yl)-4-methyl-4H-[1,2,4]triazol-3-ylsulfanyl)-propyl]-piperazin-1-yl}-6-cyclopropyl-pyrimidine,
2-cyclopropyl-4-{4-[3-(5-pyrazin-4-methyl-4H-[1,2,4]triazol-3-ylsulfanyl)-propyl]-piperazin-1-yl}-6-tert-butyl-pyrimidine,
2-tert-butyl-4-{4-[3-(5-(pyrid-3-yl)-4-methyl-4H-[1,2,4]triazol-3-ylsulfanyl)-propyl]-piperazin-1-yl}-6-cyclopropyl-pyrimidine,
2-cyclopropyl-4-{4-[3-(5-(pyrid-3-yl)-4-methyl-4H-[1,2,4]triazol-3-ylsulfanyl)-propyl]-piperazin-1-yl}-6-tert-butyl-pyrimidine,
2-tert-butyl-4-{4-[3-(5-phenyl-4-methyl-4H-[1,2,4]triazol-3-yloxy)propyl]-piperazin-1-yl}-6-cyclopropyl-pyrimidine,
2-cyclopropyl-4-{4-[3-(5-phenyl-4-methyl-4H-[1,2,4]triazol-3-yloxy)-propyl]-piperazin-1-yl}-6-tert-butyl-pyrimidine,
2-tert-butyl-4-{4-[3-(5-(4-fluoro-phenyl)-4-methyl-4H-[1,2,4]triazol-3-yloxy)-propyl]-piperazin-1-yl}-6-cyclopropyl-pyrimidine,
2-tert-butyl-4-{4-[3-(5-pyrazin-4-methyl-4H-[1,2,4]triazol-3-yloxy)-propyl]-piperazin-1-yl}-6-cyclopropyl-pyrimidine,
2-cyclopropyl-4-{4-[3-(5-pyrazin-4-methyl-4H-[1,2,4]triazol-3-yloxy)propyl]-piperazin-1-yl}-6-tert-butyl-pyrimidine,
2-cyclopropyl-4-{4-[3-(5-(1-methylpyrrol-2-yl)-4-methyl-4H-[1,2,4]triazol-3-ylsulfanyl)-propyl]-piperazin-1-yl}-6-tert-butyl-pyrimidine,
2-cyclopropyl-4-{4-[3-(5-(1-methylpyrrol-3-yl)-4-methyl-4H-[1,2,4]triazol-3-ylsulfanyl)-propyl]-piperazin-1-yl}-6-tert-butyl-pyrimidine,
2-tert-butyl-4-(1-methyl-cyclopropyl)-6-{4-[3-(4-methyl-5-phenyl-4H-[1,2,4]triazol-3-yloxy)-propyl]-piperazin-1-yl}-pyrimidine,
2-tert-butyl-4-cyclobutyl-6-{4-[3-(4-methyl-5-phenyl-4H-[1,2,4]triazol-3-yloxy)-propyl]-piperazin-1-yl}-pyrimidine,
2-(1-methyl-cyclopropyl)-4-{4-[3-(4-methyl-4H-[1,2,4]triazol-3-ylsulfanyl)-propyl]-piperazin-1-yl}-6-trifluoromethyl-pyrimidine,
2-tert-butyl-4-cyclobutyl-6-(4-{3-[4-methyl-5-(1-methyl-1H-pyrrol-2-yl)-4H-[1,2,4]triazol-3-ylsulfanyl]-propyl}-piperazin-1-yl)-pyrimidine, their tautomers, enantiomers and diastereomers, and the physiologically tolerated acid addition salts of these compounds and the enantiomers, diastereomers and tautomers thereof.

Preferred examples of compounds of the formula Ii comprise
2-tert-Butyl-4-{4-[3-(1,3-dimethyl-1H-pyrazol-5-ylsulfanyl)-propyl]-piperazin-1-yl}-6-cyclopropyl-pyrimidine,
2-tert-Butyl-4-{4-[3-(1,3-dimethyl-1H-pyrazol-5-ylsulfanyl)-propyl]-piperazin-1-yl}-6-cyclobutyl-pyrimidine,
2-tert-Butyl-4-{4-[3-(1,3-dimethyl-1H-pyrazol-5-yloxy)-propyl]-piperazin-1-yl}-6-cyclobutyl-pyrimidine,
2-tert-Butyl-4-{4-[3-(1,3-dimethyl-1H-pyrazol-5oxy)-propyl]-piperazin-1-yl}-6-cyclopropyl-pyrimidine,
2-tert-Butyl-4-{4-[3-(1-methyl-1H-pyrazol-5-ylsulfanyl)-propyl]-piperazin-1-yl}-6-cyclopropyl-pyrimidine,
2-tert-Butyl-4-{4-[3-(1-methyl-1H-pyrazol-5-ylsulfanyl)-propyl]-piperazin-1-yl}-6-cyclobutyl-pyrimidine,
2-tert-Butyl-4-{4-[3-(1-methyl-1H-pyrazol-5-yloxy)-propyl]-piperazin-1-yl}-6-cyclobutyl-pyrimidine,
2-tert-Butyl-4-{4-[3-(1-methyl-1H-pyrazol-5-yloxy)-propyl]-piperazin-1-yl}-6-cyclopropyl-pyrimidine,
2-tert-Butyl-4-{4-[3-(1-cyclopropyl-1H-pyrazol-5-ylsulfanyl)-propyl]-piperazin-1-yl}-6-cyclopropyl-pyrimidine,
2-tert-Butyl-4-{4-[3-(1-cyclopropyl-1H-pyrazol-5-ylsulfanyl)-propyl]-piperazin-1-yl}-6-cyclobutyl-pyrimidine,
2-tert-Butyl-4-{4-[3-(1-cyclopropyl-1H-pyrazol-5-yloxy)-propyl]-piperazin-1-yl}-6-cyclobutyl-pyrimidine,
2-tert-Butyl-4-{4-[3-(1-cyclopropyl-1H-pyrazol-5-yloxy)-propyl]-piperazin-1-yl}-6-cyclopropyl-pyrimidine, their tautomers, enantiomers and diastereomers, and the physiologically tolerated acid addition salts of these compounds and the enantiomers, diastereomers and tautomers thereof.

Preferred examples of compounds of the formula Ik comprise
2-tert-Butyl-4-{4-[3-(1-methyl-1H-pyrazol-3-ylsulfanyl)-propyl]-piperazin-1-yl}-6-cyclopropyl-pyrimidine,
2-tert-Butyl-4-{4-[3-(1-methyl-1H-pyrazol-3-ylsulfanyl)-propyl]-piperazin-1-yl}-6-cyclobutyl-pyrimidine,
2-tert-Butyl-4-{4-[3-(1-methyl-1H-pyrazol-3-yloxy)-propyl]-piperazin-1-yl}-6-cyclobutyl-pyrimidine,
2-tert-Butyl-4-{4-[3-(1-methyl-1H-pyrazol-3-yloxy)-propyl]-piperazin-1-yl}-cyclopropyl-pyrimidine,
2-tert-Butyl-4-{4-[3-(1-cyclopropyl-1H-pyrazol-3-ylsulfanyl)-propyl]-piperazin-1-yl}-6-cyclopropyl-pyrimidine,
2-tert-Butyl-4-{4-[3-(1-cyclopropyl-1H-pyrazol-3-ylsulfanyl)-propyl]-piperazin-1-yl}-6-cyclobutyl-pyrimidine,
2-tert-Butyl-4-{4-[3-(1-cyclopropyl-1H-pyrazol-3-yloxy)-propyl]-piperazin-1-yl}-6-cyclobutyl-pyrimidine,
2-tert-Butyl-4-{4-[3-(1-cyclopropyl-1H-pyrazol-3-yloxy)-propyl]-piperazin-1-yl}-6-cyclopropyl-pyrimidine, their tautomers, enantiomers and diastereomers, and the physiologically tolerated acid addition salts of these compounds and the enantiomers, diastereomers and tautomers thereof.

In a second embodiment of the invention X is a group C(O)—NR$^8$. Preferably the carbonyl group is bound to Ar. In this embodiment preference is given to compounds I, wherein Ar is selected from the group consisting of phenyl, pyridyl, pyrazinyl, pyridazinyl and pyrimidinyl. In this embodiment, Ar may preferably carry 0, 1 or 2 of the aforementioned radicals R$^a$.

Preferred radicals R$^a$ are halogen, NO$_2$, CN, C$_1$-C$_2$-fluoroalkyl, especially CF$_3$ and C$_1$-C$_4$-alkoxy, especially methoxy or ethoxy.

In the second embodiment A is preferably butan-1,4-diyl, which may carry 1 or 2 methyl groups, and especially butan-1,4-diyl.

Amongst the compounds of the second embodiment, compounds of the formulae Im, the tautomers, enantiomers and diastereomers of Im and the physiologically tolerated acid addition salts of these compounds are especially preferred:

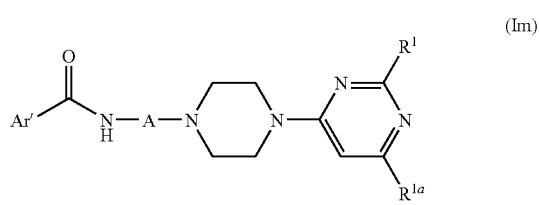

(Im)

wherein R$^1$, R$^{1a}$ and A are as defined above and Ar' is selected from phenyl, pyridyl, pyrimidinyl, pyrazinyl and pyridazinyl, wherein Ar' may carry 1, 2 or 3 of the aforementioned radicals R$^a$.

Preferred examples of compounds of the formula Im comprise

N-{4-[4-(2-tert-Butyl-6-cyclobutyl-pyrimidin-4-yl)-piperazin-1-yl]-butyl}-4-fluoro-benzamide N-{4-[4-(2-tert-Butyl-6-cyclobutyl-pyrimidin-4-yl)piperazin-1-yl]-butyl}-2-fluoro-benzamide N-{4-[4-(2-tert-Butyl-6-cyclobutyl-pyrimidin-4-yl)-piperazin-1-yl]-butyl}-3-fluoro-benzamide N-{4-[4-(2-tert-Butyl-6-cyclobutyl-pyrimidin-4-yl)-piperazin-1-yl]-butyl}-2,4-difluoro-benzamide N-{4-[4-(2-tert-Butyl-6-cyclobutyl-pyrimidin-4-yl)-piperazin-1-yl]-butyl}-isonicotinamide N-{4-[4-(2-tert-Butyl-6-cyclobutyl-pyrimidin-4-yl)-piperazin-1-yl]-butyl}-nicotinamide Pyridine-2-carboxylic acid {4-[4-(2-tert-butyl-6-cyclobutyl-pyrimidin-4-yl)-piperazin-1-yl]-butyl}-amide Pyrazine-2-carboxylic acid {4-[4-(2-tert-butyl-6-cyclobutyl-pyrimidin-4-yl)-piperazin-1-yl]-butyl}-amide Pyrimidine-5-carboxylic acid {4-[4-(2-tert-butyl-6-cyclobutyl-pyrimidin-4-yl)-piperazin-1-yl]-butyl}-amide N-{4-[4-(2-tert-Butyl-6-cyclobutyl-pyrimidin-4-yl)-piperazin-1-yl]-butyl}-4-nitro-benzamide Pyridazine-4-carboxylic acid {4-[4-(2-tert-butyl-6-cyclobutyl-pyrimidin-4-yl)-piperazin-1-yl]-butyl}-amide N-{4-[4-(2-tert-Butyl-6-cyclobutyl-pyrimidin-4-yl)-piperazin-1-yl]-butyl}-4-fluoro-N-methyl-benzamide their tautomers, enantiomers and diastereomers, and the physiologically tolerated acid addition salts of these compounds and the enantiomers, diastereomers and tautomers thereof.

The compounds of the formula I can be prepared in analogy to methods, which are well known in the art, e.g. from the international patent applications cited in the introductory part. Preferred method for the preparation of compounds I wherein X is S or O is outlined in scheme i):

Scheme i:

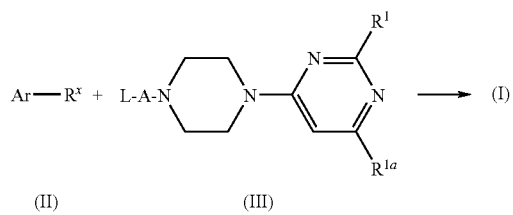

Reaction of an aromatic hydroxy or mercapto compound of the formula II with a piperazinylpyrimidine compound of the formula II, wherein R$^x$ is SH or OH and L is a conventional leaving group, which is susceptible to nucleophilic replacement, such as halogen, e.g. chlorine, bromine or iodine, alkylsulfonyloxy such as methanesulfonyloxy, arylsulfonyloxy, such as phenylsulfonyloxy or tolylsulfonyloxy (tosylate) etc. The reaction can be performed using the conditions as described herein or in the prior art cited in the introductory part. R$^x$ may also be chlorine or bromine. L is then SH. In this case the reaction can be performed using the reaction conditions as described by Hester, Jackson B., Jr.; Von Voigtlander, Philip. Journal of Medicinal Chemistry (1979), 22(11).

Another preferred method for the preparation of compounds I is outlined in scheme ii):

Scheme ii:

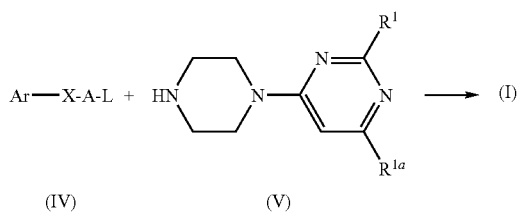

Reaction of a compound of the formula IV with a piperazinylpyrimidine compound of the formula V, wherein L is a conventional leaving group being susceptible to a nucleophilic replacement such as halogen, e.g. chlorine, bromine or iodine, alkylsulfonyloxy, arylsulfonyloxy etc.

A further method for the preparation of compounds I wherein X is a single bond and Ar is 4-hydroxypyrimidin-2-yl is outlined in scheme iii:

Scheme iii:

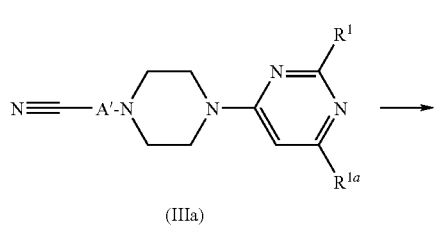

(IIIa)

-continued

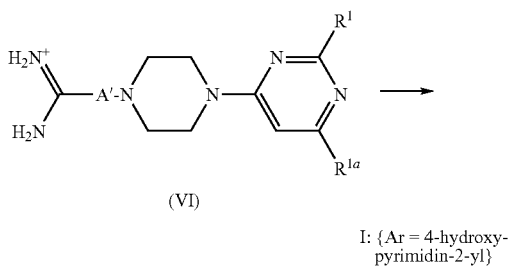

I: {Ar = 4-hydroxy-pyrimidin-2-yl}

In scheme iii $R^1$ and $R^{1a}$ are as defined above. A' has the meanings given for A. In a first step, the nitrile compound IIIa is converted into the amidinium compound VI by first reacting IIIa with hydrochloric acid in an alkanol, e.g. methanol or ethanol and subsequently reacting the thus obtained hydroxamic ester with ammonia according to conventional methods for preparing amidines (see e.g. J. Med. Chem. (2001), 44(8), 1217-1230, Synthetic Communications (1989), 19 (13-14), 223742, and J. Am. Chem. Soc. (1988), 110(7), 2192-2201). In a second step the amidino group is used as a building block for the pyrimidine hetorocycle Ar. I.e compound VI is reacted with an alkyl ester of 3-hydroxyacrylic acid, in particular the $C_1$-$C_4$-alkyl ester such as the methyl or ethyl ester, according to conventional methods for preparing pyrimidines, e.g. according to the method described in J. Med. Chem. (2001), 44(17), 2695-2700 or Heterocycles (1979), 12(3), 383-6.

A further method for the preparation of compounds I wherein X is O is outlined in scheme iv:

Scheme iv:

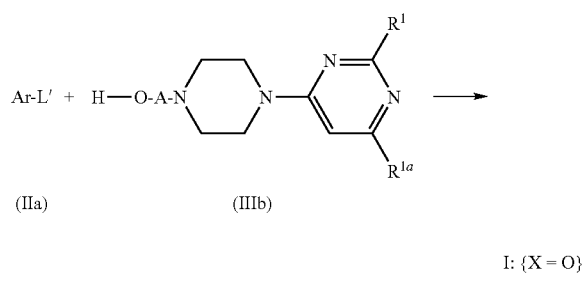

I: {X = O}

In scheme iv Ar, A and $R^1$ and $R^{1a}$ are as defined above. L' is a leaving group, which is prone to undergo an aromatic substitution. Examples for L' comprise halogen, especially chlorine, bromine or iodine, alkylsulfinyl, especially methylsulfinyl and alkylsulfonyl, especially methylsulfonyl. The reaction can be performed according to the method described in J. Org. Chem. (2001), 66(17), 5723-30, J. Am. Chem. Soc. (2001), 123(16), 3854-55, U.S. Pat. No. 5,811,540, Bulletin of the Korean Chemical Society (1995), 16(6), 489-92, Tetrahedron (1993), 49(11), 2169-84, Tetrahedron (1990), 46(2), 595-606, J. Chem. Soc. Chem. Comm. (1971), (6), 249-250, and Heterocycles (1977), (8), 299-305.

A method for the preparation of compounds I wherein X is C(O)NH is outlined in scheme v:

Scheme v:

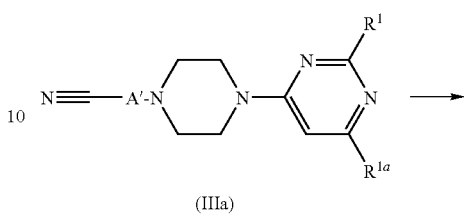

(IIIa)

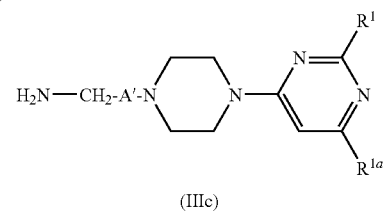

(IIIc)

(IIIc) + Ar—C(O)-Hal ⟶ (I)

In scheme v Ar and $R^1$ and $R^{1a}$ are as defined above. Hal is halogen, especially chlorine or bromine. A' is ethan-1,2-diyl or propan-1,3-diyl, which may carry 1, or 2 alkyl groups. In a first step, the nitrile is reduced to the corresponding amine IIIc. The reduction can be performed according to standard reduction procedures, which are known from standard organic textbooks such as J. March, *Advanced Organic Chemistry*, 3. ed. John Wiley, New York 1985, pp. 815 and 1095 and from the literature cited therein. Then, the amine is reacted with the acid halide Ar—C(O)Hal or the corresponding acid Ar—C(O)OH in an amidation reaction to obtain the compounds of formula I with X being C(O)NH. The amidation reaction can be performed according to the method described in Bioorg. Med. Chem. Letters (2003), 13(6), 1161-64, Synlett (2003), (4), 542-546, J. Organometallic Chemistry (2003), 668(1-2), 67-74. In analogy to the method outlined in scheme v compounds I wherein X is $C(O)NR^8$ can be prepared by starting from secondary amines IIId, which can be prepared form the primary amines IIIc by standard organic procedures, e.g. by Gabriels Synthesis and related reactions (see e.g. J. March, *Advanced Organic Chemistry*, 3. ed. John Wiley, New York 1985, pp. 377 ff) or by reductive amination.

Compounds of the formula IIIc can be also prepared from compounds V by reacting a compound of formula V with a N-(w-bromoalkyl)phthalimid and subsequent hydrolysis or hydrazinolylsis of the resulting intermediate compound.

A preferred route to compounds of the formula III, IIIa, IIIb is shown in scheme vi:

Scheme vi:

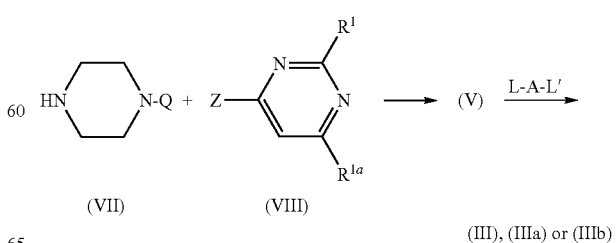

(III), (IIIa) or (IIIb)

In a first step a piperazine compound VII, wherein Q is H or an protecting group for secondary amines, is reacted with a pyrimidine compound VIII wherein Z is halogen to yield a compound of the formula V. This compound is then reacted with a bifunctional alkane compound L-A-L', wherein L' is a leaving group and L is either a leaving group of different reactivity which can be replaced by nucleophiles e.g. (L=Cl and L'=Br) or L is CN or O-Acetyl. This method is known from the prior art cited in the introductory part of the application, e.g. from WO 99/09015 and WO 03/002543. Compounds of the formula IIIb wherein L is OH can be obtained from compounds III with L=O-Acetyl by hydrolysis of the acetyl group. Compounds IIIb may also be prepared by the method disclosed in WO 03/002543.

The preparation of the pyrimidine compounds VIII is simply achieved by reaction of a suitable amidinium chloride X with a suitable β-ketoester IX to yield a 2/6-substituted-4-hydroxypyrimidine of the formula XI which can be transformed in the halo compound VIII by reacting it with halogenating agent such as thionyl chloride, phosphoryl chloride, phosphoryl bromide, phosphorous trichloride, phosphorous tribromide, phosphorous pentachloride etc (see scheme vii):

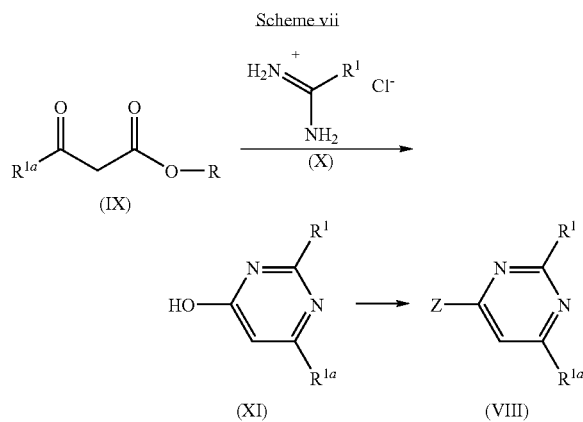

β-Ketoesters IX are known in the art or can be simply synthesized according to the methods described in this application from the corresponding acid chlorides $R^{1a}$—COCl by reaction with meldrum's acid (2,2-dimethyl-4,6-dioxo-1,3-dioxan) according to the process as described herein and in: (i) B. Trost et al., Journal of the American Chemical Society (2002), 124(35), 10396-10415, (ii) Paknikar, S. K. et al., Journal of the Indian Institute of Science (2001), 81(2), 175-179, (iii) Brummell, David G. et al., Journal of Medicinal Chemistry (2001), 44(1), 78-93. Likewise, amidinium chlorides such as Tert-butyl-amidinium chloride are commercially available from e.g. Maybridge Ltd, or can be prepared according to known procedures.

A simple method of producing the compounds of formula II, wherein Ar is a radical of the formula h and $R^x$ is SH, comprises the reaction of a carboxylic acid of the formula $R^f$—COOH with 4-substituted-3-thiosemicarbazide in the presence of 1,1' carbonyldiimidazole as shown in scheme viii:

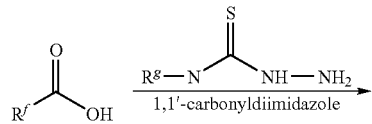

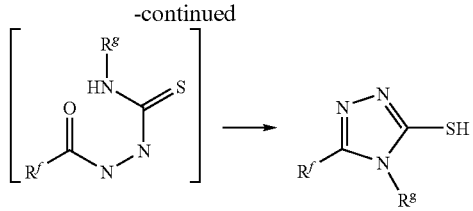

The reaction can be performed using the conditions as described herein and in (i) El-Deen, I. M.; Ibrahim, H. K., Phosphorus, Sulfur and Silicon and the Related Elements (2002), 177(3), 733-740. (ii) Faidallah, Hassan M.; Sharshira, Essam M.; Basaif, Salem A.; A-Ba-Oum, Abd El-Kader. Phosphorus, Sulfur and Silicon and the Related Elements (2002), 177(1), 67-79. (iii) Tumkevicius, Sigitas; Vainilavicius, Povilas. Journal of Chemical Research, Synopses (2002), (5), 213-215. (iv) Palaska, Erhan; Sahin, Gulay; Ekizoglu, Melike; Ozalp, Meral. FABAD Journal of Pharmaceutical Sciences (2001), 26(3), 113-117. (v) Li, Xin Zhi; Si, Zong Xing. Chinese Chemical Letters (2002), 13(2), 129-132, (vi) Suni, M. M.; Nair, V. A.; Joshua, C. P. Tetrahedron (2001), 57(10), 2003-2009.

The compounds of the formulae II, IIa and IV are known in the art or can be prepared according to methods described in the literature e.g. in Houben Weyl, "Handbuch der Organischen Chemie", 4th Ed., Thieme Verlag, Stuttgart 1994, Volume E8/d, pages 479 et seq.; in A. R. Katritzky, C. W. Rees (ed.) "Comprehensive Heterocyclic Chemistry", 1st Ed. Pergamon Press 1984 and literature cited therein; or "The Chemistry of Heterocyclic Compounds" J. Wiley & Sons Inc. NY and literature cited therein. The compounds of the formulae III, IIIa, V and VI can be prepared according to routine methods as described e.g. in J. A. Kiristy et al., *J. Med. Chem.* 1978, 21, 1303 or C. B. Pollard, *J. Am. Chem. Soc.* 1934, 56, 2199, Tagawa et al. Arch. Pharm. 2002 335 (2) S. 99-103.

If not otherwise indicated, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

Examples of solvents which can be used are ethers, such as diethyl ether, diisopropyl ether, methyl tertbutyl ether or tetrahydrofuran, aprotic polar solvent, such as dimethylformamide, dimethyl sulfoxide, dimethoxyethahe, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are surprisingly highly selective dopamine $D_3$ receptor ligands which, because of their low affinity for other receptors such as $D_i$ receptors, $D_4$ receptors, $\alpha$1-adrenergic and/or $\alpha$2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists. A compound of the invention can be a dopamine $D_3$ receptor agonist, including partial agonistic activity, or a dopamine $D_3$ receptor antagonist, including partial antagonistic activity.

The high affinity of the compounds according to the invention for $D_3$ receptors is reflected in very low in-vitro receptor binding constants ($K_i(D_3)$ values) of as a rule less than 50 nM (nmol/l), preferably of less than 10 nM and, in particular of less than 5 nM. The displacement of [$^{125}$I]-iodosulpride can, for example, be used in receptor binding studies for determining binding affinities for $D_3$ receptors.

The selectivity of the compounds according to the invention, i.e. the ratio $K_i(D_2)/K_i(D_3)$ of the receptor binding constants, is as a rule at least 50, preferably at least 100, even better at least 150. The displacement of [$^3$H]SCH23390, [$^{125}$I] iodosulpride or [$^{125}$I] spiperone can be used, for example, for carrying out receptor binding studies on $D_1$, $D_2$ and $D_4$ receptors.

Because of their binding profile, the compounds can be used for treating diseases which respond to dopamine $D_3$ receptor ligands (or which are susceptible to treatment with a dopamine $D_3$ receptor ligand, respectively), i.e. they are effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disorders which can be treated in accordance with the invention also include Parkinson's disease and epilepsy and, in particular, the affective disturbances connected thereto.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogeneously administered binding partners (ligands) to dopamine $D_3$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney function which are caused by diabetes mellitus (see WO 00/67847) and, especially, diabetic nephropathy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the invention without limiting it.

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts ($\delta$) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Intermediates a. Preparation of 4-[4-(3-chloro-propyl)-piperazin-1-yl]-pyrimidines a.1 2-tert-Butyl-4-[4-(3-chloro-propyl)-piperazin-1-yl]-6-cyclobutyl-pyrimidine a.1.1: Methyl-2-cyclobutanoyl-acetate 22 g of meldrum's acid (2,2-dimethyl-1,3-dioxane-4,6-dione) (152.7 mmol) and 36.9 ml of pyridine (457.2 mmol) were dissolved in 200 ml of dichloromethane. 18.1 g of cyclobutylcarbonic acid chloride were added at 0 to 10° C. The reaction mixture was stirred overnight at room temperature, washed with 1 N HCl and extracted with dichloromethane. The organic layer was washed with water, dried over magnesium sulfate, filtered, and then concentrated to dryness. The oily residue was dissolved in 300 ml of methanol and heated under reflux for 2 h. The reaction mixture was concentrated to dryness and the residue purified via silica gel chromatography with ethyl acetate as eluent. Yield: 21.2 g MS (ESI) m/z: 157.1 [M+H]$^+$
$^1$H-NMR (CDCl$_3$): δ [ppm] 3.7 (s, 3H), 3.4 (s, 2H), 3.3-3.4 (m, 1H), 2.2-2.4 (m, 2H), 2.1-2.25 (m, 2H), 1.9-2.1 (m, 1H), 1.8-1.9 (m, 1H).

a.1.2: 2-tert-Butyl-4-hydroxy-6-cyclobutyl-pyrimidine 9.2 g of tert-butyl amidinium chloride (67.3 mmol, Maybridge) and 12.6 g of methyl-2-cyclobutanoyl acetate (80.7 mmol) were dissolved/suspended in 100 ml of methanol. 14.5 g of sodium methanolate (268.4 mmol) were added in portions to the solution at 10° C. The suspension was then stirred at room temperature overnight. The reaction mixture was concentrated to roughly half the volume and filtered. The filtrate was extracted with water and dichloromethane. The organic phase was dried over magnesium sulfate, filtered, and then concentrated to dryness. The residue was stirred with acetone and the precipitate was collected by filtration. Yield: 11.9 g (85.7%).

MS (ESI) m/z: 207.2 [M+H]$^+$ a.1.3: 2-tert-Butyl-4-chloro-6-cyclobutyl-pyrimidine 9.9 g of 2-tert-butyl-4-hydroxy-6-cyclobutyl-pyrimidine (48 mmol) were dissolved in 80 ml of toluene and 1 ml of dimethylformamide. 10.7 ml of POCl$_3$ (114.8 mmol) were added dropwise at 10° C. Stirring was continued for 3 h at room temperature. The reaction mixture was poured into water, and the aqueous layer extracted with dichloromethane. The organic layer was dried over magnesium sulfate, filtered, and then concentrated to dryness to give 10.8 g of a yellowish oil (quant.).

a.1.4: 2-tert-Butyl-4-(piperazin-1-yl)-6-cyclobutyl-pyrimidine 24.8 g of piperazine (287.9 mmol) were dissolved in 350 ml of ethanol and heated to reflux. 24.9 g of 2-tert-butyl-4-chloro-6-cyclobutyl-pyrimidine (48.06 mmol), dissolved in 50 ml of ethanol, were added dropwise to the solution. The solution was refluxed for further 3 h, cooled to room temperature and then extracted with water and ethyl acetate. The organic layer was washed with 5% citric acid (aq.), and the aqueous layer was adjusted to alkaline pH with 2 N NaOH. The alkaline aqueous layer was reextracted with ethyl acetate, and the organic phase was dried over magnesium sulfate, filtered and concentrated to dryness to yield 8.6 g (65.2%) of the title compound.

MS (ESI) m/z: 275.2 [M+H]$^+$
$^1$H-NMR (CDCl$_3$): δ [ppm] 6.1 (s, 1H), 3.6 (m, 4H), 3.4 (m, 1H), 2.9 (m, 4H), 2.3 (m, 4H), 1.8-2.1 (m, 3H), 1.3 (s, 9H)

a.1.5: 2-tert-Butyl-4-[4-(3-chloro-propyl)-piperazin-1-yl]-6-cyclobutyl-pyrimidine 3.5 g of 2-tert-butyl-4-(piperazin-1-yl)-6-cyclobutyl-pyrimidine (12.75 mmol), 2.3 g of 1-bromo-3-chloro-propane (14.6 mmol) and 2.8 ml of triethylamine (20.1 mmol) were dissolved in 70 ml of dimethylformamide. The mixture was stirred at room temperature overnight and for further 3 h at 40° C. The reaction mixture was then extracted with water and ethyl acetate. The organic layer was dried over magnesium sulfate, filtered, and concentrated to dryness. The crude product was then purified by silica gel chromatography (dichloromethane as eluent) to yield 3.0 g (67%) of the title compound.

A larger batch was prepared by using the following modified procedure:

64 g of 2-tert-butyl-4-(piperazin-1-yl)-6-cyclobutyl-pyrimidine and 73 g of 1-bromo-3-chloro-propane (2 equivalents) were dissolved in 150 ml of toluene. 21.4 g of 50% aqueous sodium hydroxide (1.5 equivalents) were added followed by the addition of 3 g of tetrabutylammonium bromide (0.04 equivalents), dissolved in water. The mixture was kept at 50° C. for 5 h under vigorous stirring. The reaction mixture was extracted with water and ethyl acetate. The organic layer was dried over magnesium sulfate, filtered, and concentrated to dryness. The product was purified by chromatography on silica gel (ethyl acetate as eluent) to yield 74 g (91%) of the title compound.

MS (ESI) m/z: 351.1 [M+H]$^+$
$^1$H-NMR (DMSO): δ [ppm] 6.4 (s, 1H), 3.65 (m, 2H), 3.5-3.7 (m, broad, 4H), 3.4 (m, 1H), 2.3-2.55 (m, broad, 6H), 2.1-2.3 (m, 4H), 1.8-2.0 (m, 4H), 1.3 (s, 9H)

a.2 2-tert-Butyl-4-[4-(3-chloro-propyl)-piperazin-1-yl]-6-cyclopropyl-pyrimidine a.2.1: Methyl-2-cyclopropanoyl-acetate 48.6 g of meldrum's acid (337.4 mmol) were dissolved in 200 ml of dichloromethane at room temperature and the solution was cooled to 0° C. 40 g of pyridine (506.1 mmol) were added to said solution. 35.3 g of cyclopropyl carbonic acid chloride (337.4 mmol) were then added at 0° C. within 1 h. The reaction mixture was stirred overnight at room temperature, washed with 1 N HCl and extracted with dichloromethane. The organic layer was washed with water, dried over magnesium sulfate, filtered and then concentrated to dryness. The oily residue was dissolved in 300 ml of methanol and stirred under reflux for 2 h. The reaction mixture was concentrated to dryness and the oily residue was purified by destillation at 90° C. bath temperature to yield 42.7 g (71.1%) of the title compound.

MS (ESI) m/z: 143.1 [M+H]$^+$
$^1$H-NMR (CDCl$_3$): δ [ppm] 3.75 (s, 3H), 3.6 (s, 2H), 2.0 (m, 1H), 1.15 (m, 2H), 0.95 (m, 2H)

a.2.2: 2-tert-Butyl-4-hydroxy-6-cyclopropyl-pyrimidine 16.3 g tert-butyl amidinium chloride (119.6 mmol, Maybridge) were dissolved/suspended in 350 ml of methanol at room temperature. 30.4 g of sodium methanolate (562.8 mmol) were added in portions to the solution at 10° C., After stirring for 30 minutes, a solution of 20 g of methyl-2-cyclopropanoyl acetate (140.7 mmol) in 150 ml of methanol was added over 2 h. The suspension was then stirred at room temperature overnight, concentrated to roughly half the volume, and filtered. 200 ml of dichloromethane were added to the filtrate and the organic layer was washed 3 times with water. The aqueous phases were combined. The aqueous phase was adjusted to pH 3 with aq. HCl, whereby a white precipitate was formed. The precipitate was collected by filtration, redissolved in dichloromethane, dried over magnesium sulfate and filtered. The solvent was concentrated to dryness to yield 14.8 g (67.2%) of the title compound.

MS (ESI) m/z: 193.1 [M+H]$^+$ a.2.3: 2-tert-Butyl-4-chloro-6-cyclopropyl-pyrimidine 14.8 g 2-tert-butyl-4-hydroxy-6-cyclopropyl-pyrimidine (76.9 mmol) were dissolved in 100 ml of toluene and 3 ml of dimethylformamide. 23.6 ml of POCl$_3$ (153.7 mmol) were added dropwise at 10° C. After stirring overnight at room temperature most of the toluene was evaporated. The mixture was cooled with ice and 20 ml of water were added cautiously. Subsequently, an additional 200 ml of water were added and the aqueous phase was extracted four times with dichloromethane. The combined organic phases were dried over magnesium sulfate, filtered, and then concentrated to dryness to yield 17 g of a yellowish oil (quant.).

MS (ESI) m/z: 211.1 [M+H]$^+$
$^1$H-NMR (CDCl$_3$): δ (ppm) 6.95 (s, 1H), 1.85 (m, 1H), 1.35 (s, 9H), 1.2 (m, 2H), 1.1 (m, 2H)

a.2.4: 2-tert-Butyl-4-(piperazin-1-yl)-6-cyclopropyl-pyrimidine 25.1 g of piperazine (291.4 mmol) were dissolved in 100 ml of ethanol and heated to 50° C. 17 g of 2-tert-butyl-4-chloro-6-cyclopropyl-pyrimidine (81 mmol), dissolved in 100 ml of ethanol, were added dropwise within 2 h. After heating to reflux at 70° C. for 5 h the reaction mixture was stirred at room temperature overnight. The ethanol was evaporated and the residue suspended in 200 ml of water. The aqueous phase was extracted 4 times with 100 ml of dichloromethane each. Drying over magnesium sulfate, filtration, and evaporation to dryness gave 19.2 g (90.9%) of the title compound.

MS (ESI) m/z: 261.1 [M+H]$^+$ a.2.5: 2-tert-Butyl-4-[4-(3-chloro-propyl)-piperazin-1-yl]-6-cyclopropyl-pyrimidine 19.2 g of 2-tert-butyl-4-piperazin-1-yl-6-cyclopropyl-pyrimidine (73.7 mmol) were dissolved in 50 ml of toluene. 14.6 ml of 1-bromo-3-chloropropane (147.4 mmol) and 3.4 g of sodium hydroxide (84.7 mmol) were added, followed by dropwise addition of 0.95 g of tetrabutylammonium bromide (2.95 mmol, dissolved in water). After stirring for 5 h at 60° C. additional 1-bromo-3-chloropropane was added to drive the reaction to completion. The reaction mixture was cooled, water was added and the product extracted 3 times with ethyl acetate. The organic layers were dried over magnesium sulfate, filtered, and the solvent was evaporated. The crude product was purified by chromatography on silica gel using dichloromethane/ethyl acetate (9:1). Fractions containing the product were combined, the solvent was evaporated to yield 15.4 g of the title compound.

MS (ESI) m/z: 337.2 [M+H]$^+$
$^1$H-NMR (DMSO): δ [ppm] 6.5 (s, 1H), 4.0-4.3 (m, 1H), 3.7 (m, 2H), 3.55 (m, 4H), 2.4 (m, 5H), 1.9 (m, 3H), 1.25 (s, 9H), 0.9 (m, 2H), 0.8 (m, 2H)

a.3 2-tert-Butyl-4-[4-(3-chloro-propyl)-piperazin-1-yl]-6-(1-methylcyclopropyl)-pyrimidine 7 g of 2-tert-butyl-4-piperazin-1-yl-6-(1-methylcyclopropyl)-pyrimidine (25.5 mmol; prepared by analogy to steps a.2.1 to a.2.4 starting from 1-methylcyclopropyl carbonic acid chloride) were dissolved in 50 ml of dimethyl formamide. 2.58 of triethylamine (25.5 mmol), and 3.53 g of potassium carbonate were added, followed by dropwise addition of 4.62 g of 1-bromo-3-chloropropane. After stirring for 1.5 h at 50° C. the reaction mixture was stirred overnight at room temperature. The precipitate was filtered off and washed with dimethylformamide. The filtrate was partitioned between 150 ml of ethyl acetate and 50 ml of water. The organic layer was separated and the aqueous layer was extracted with 30 ml of ethyl acetate. The combined organic layers were dried over magnesium sulfate, filtered and evaporated to dryness. The residue was purified by chromatography on silica gel (ethyl acetate) to yield 4.6 g of the title compound.

MS (ESI) m/z: 351.2 [M+H]$^+$ a.4 2-cyclobutyl-4-[4-(3-chloro-propyl)-piperazin-1-yl]-6-(1-methylcyclopropyl)-pyrimidine 2-Cyclobutyl-4-{4-[3-chloro-propyl)-piperazin-1-yl}-6-tert-butyl-pyrimidine was prepared by the same methods as described for the other 4-[4-(3-chloro-propyl)-piperazin-1-yl]-pyrimidines, starting from cyclobutyl-carboxamidine respectively.

a.4.2.: 2-cyclobutyl-4-hydroxy-6-tert-butyl-pyrimidine

MS (ESI) m/z: 207.1 [M+H]$^+$ a.4.3.: 2-cyclobutyl-4-chloro-6-tert-butyl-pyrimidine

MS (ESI) m/z: 225.1 [M+H]$^+$ a.4.4.: 2-cyclobutyl-4-(piperazin-1-yl)-6-tert-butyl-pyrimidine

MS (ESI) m/z: 275.4[M+H]$^+$ a.4.5.: 2-cyclobutyl-4-{4-[3-chloro-propyl)-piperazin-1-yl}-6-tert-butyl-pyrimidine MS (ESI) m/z: 351.1 [M+H]$^+$ a.5 2-cyclopropyl-4-[4-(3-chloro-propyl)-piperazin-1-yl]-6-(1-methylcyclopropyl)-pyrimidine 2-Cyclopropyl-4-{4-[3-chloro-propyl)-piperazin-1-yl}-6-tert-butyl-pyrimidine was prepared by the same methods as described for the other 4-[4-(3-chloro-propyl)-piperazin-1-yl]-pyrimidines, starting from cyclopropylcarboxamidine respectively.

b. Preparation of 4-[4-(2/6-substituted-pyrimidin-4-yl)-piperazin-1-yl]-butylamines b.1 4-[4-(2-tert-Butyl-6-cyclobutyl-pyrimidin-4-yl)-piperazin-1-yl]-butylamine b.1.1: 2-{4-[4-(2-tert-Butyl-6-cyclobutyl-pyrimidin-4-yl)-piperazin-1-yl]-butyl}-isoindole-1,3-dione 1.45 g of 2-tert-butyl-4-(piperazin-1-yl)-6-cyclobutyl-pyrimidine (5.28 mmol), 1.5 g of N-(4-bromobutyl)phthalimid (5.28 mmol) and 0.8 g of triethylamine (7.9 mmol) were dissolved in 20 ml of dimethylformamide and stirred for 16 h at room temperature. The reaction mixture was extracted with water and ethyl acetate. The organic layer was dried over magnesium sulfate, filtered, and concentrated to dryness. The oily residue began to crystallise upon standing, was stirred with acetonitrile, and finally filtered to yield 0.55 g of the title compound.

MS (ESI) m/z: 476.4 [M+H]$^+$
$^1$H-NMR (DMSO): δ [ppm] 13.9 (m, broad, 1H), 11.9 (m, broad, 1H), 7.85 (m, 4H), 7.1 (m, 1H), 5.0 (m, broad, 1H), 4.65 (m, broad, 1H), 4.1 (m, broad, 1H), 3.8 (m, 1H), 3.6 (m, broad, 4H), 3.1 (m, broad, 4H), 2.3 (m, broad, 4H), 2.0 (m, 1H), 1.8 (m, 3H), 1.65 (m, 2H), 1.4 (s, 9H).

b.1.2: 4-[4-(2-tert-Butyl-6-cyclobutyl-pyrimidin-4-yl)-piperazin-1-yl]-butylamine 2.4 g of 2-{4-[4-(2-tert-butyl-6-cyclobutyl-pyrimidin-4-yl)-piperazin-1-yl]-butyl}-isoindole-1,3-dione (5.05 mmol) and 1.0 g of hydrazine hydrate (20.2 mmol) were dissolved in 20 ml of ethanol and heated to reflux for 1 h. The precipitate was filtered and the filtrate extracted with water and ethyl acetate. The organic layer was dried over magnesium sulfate, filtered, and concentrated to dryness to yield 1.2 g of the title compound.

MS (ESI) m/z: 346.3 [M+H]$^+$ b.2 {4-[4-(2-tert-Butyl-6-cyclobutyl-pyrimidin-4-yl)-piperazin-1-yl]-butyl}-methyl-amine hydrochloride b.2.1: {4-[4-(2-tert-Butyl-6-cyclobutyl-pyrimidin-4-yl)-piperazin-1-yl]-4-oxo-butyl}-methyl-carbamic acid tert-butyl ester 6 g of 4-(tert-butoxycarbonyl-methyl-amino)-butyric acid (27.6 mmol) and 5.53 g of triethylamine (54.6 mmol) were dissolved in 100 ml of dimethylformamide. 4.1 g of hydroxybenzotriazole (HOBt, 30.35 mmol), 7.6 g of 2-tert-butyl-4-(piperazin-1-yl)-6-cyclobutyl-pyrimidine (27.7 mmol), and 5.8 g of N-ethyl-N'-(3-dimethylaminopropyl)-carbodimide hydrochloride (EDCl, 30.26 mmol) were added at room temperature, and the reaction mixture was stirred for 16 h. The reaction mixture was partitioned between water and ethyl acetate, the organic phase dried over magnesium sulfate, filtered, and concentrated to dryness. The crude product was purified by chromatography on silica gel using dichloromethane. Fractions containing the product were combined and the solvent evaporated to yield 13.1 g of the title compound.

MS (ESI) m/z: 474.4 [M+H]$^+$
$^1$H-NMR (CDCl$_3$): δ [ppm] 6.1 (s, 1H), 3.7 (m, 4H), 3.5-3.6 (m, 4H), 3.45 (m, 1H), 3.3 (m, 2H), 2.95 and 2.9 (d, 3H, Me), 2.2-2.4 (m, 6H), 2.0 (m, 1H), 1.9 (m, 3H), 1.45 (s, 9H), 1.35 (s, 9H).

b.2.2: {4-[4-(2-tert-Butyl-6-cyclobutyl-pyrimidin-4-yl)-piperazin-1-yl]-butyl}methyl-carbamic acid tert-butyl ester 13.1 g of {4-[4-(2-tert-butyl-6-cyclobutyl-pyrimidin-4-yl)-piperazin-1-yl]-4-oxo-butyl}-methyl-carbamic acid tert-butyl ester (27.66 mmol) were dissolved in 250 ml of tetrahydrofuran. 44.9 g of borane in tetrahydrofuran (522.44 mmol) were added dropwise within 25 min. and then the reaction mixture was heated to reflux for 1.5 h. The reaction mixture was poured onto water and extracted with ethyl acetate. The organic layer was dried over magnesium sulfate, filtered, and concentrated to dryness. The crude product was purified by chromatography on silica gel using dichloromethane-methanol (0-5%) as eluent. Fractions containing the product were combined and the solvent evaporated to yield 8.2 g of the title compound.

MS (ESI) m/z: 460.4 [M+H]$^+$
$^1$H-NMR (CDCl$_3$): δ [ppm] 6.1 (s, 1H), 3.65 (m, 4H), 3.45 (m, 1H), 3.25 (m, 2H), 2.8 (s, 3H), 2.5 (m, 4H), 2.4 (m, 2H), 2.25 (m, 4H), 2.0 (m, 1H), 1.85 (m, 1H), 1.5 (m, 4H), 1.45 (s, 9H), 1.3 (s, 9H).

b.2.3: {4-[4-(2-tert-Butyl-6-cyclobutyl-pyrimidin-4-yl)-piperazin-1-yl]-butyl}-methyl-amine hydrochloride 0.5 g of {4-[4-(2-tert-butyl-6-cyclobutyl-pyrimidin-4-yl)-piperazin-1-yl]-butyl}-methyl-carbamic acid tert-butyl ester (1.06 mmol) were treated with 10 ml of a 4 N solution of hydrochloric acid in dioxane for 16 h. The solvent was evaporated to yield 0.6 g of the deprotected amine as its hydrochloride salt.

MS (ESI) m/z: 360.3 [M+H]$^+$
$^1$H-NMR (DMSO): δ [ppm] 14.0 (s, broad, 1H), 12.0 (s, broad, 1H), 9.3 (m, broad, 2H), 7.2 (s, 1H), 5.0 (m, 1H), 4.7 (m, 1H), 4.1 (m, 1H), 3.85 (m, 1H), 3.65 (m, 4H), 2.9 (m, 2H), 2.5 (s, 3H), 2.3 (m, 4H), 2.0 (m, 1H), 1.85 (m, 3H), 1.7 (m, 2H), 1.4 (s, 9H).

c. Preparation of 3-[4-(2/6-substituted-butyl-pyrimidin-4-yl)-piperazin-1-yl]-propan-1-ols c.1 3-[4-(2-tert-Butyl-6-cyclobutyl-pyrimidin-4-yl)-piperazin-1-yl]-propan-1-ol c.1.1: Acetic acid 3-[4-(2-tert-butyl-6-cyclobutyl-pyrimidin-4-yl)-piperazin-1-yl]-propyl ester 5.5 g of 2-tert-butyl-4-piperazin-1-yl-6-cyclobutyl-pyrimidine (20.0 mmol), 3.15 g of acetic acid 3-chloro-propyl ester (23.1 mmol) and 2.76 g of triethylamine (27.3 mmol) were dissolved in 70 ml of dimethylformamide and stirred for 12 h at 80° C. After cooling, the dimethylformamide was evaporated, and the reaction mixture was partitioned between water and ethyl acetate. The organic layer was dried over magnesium sulfate, filtered, and the solvent was evaporated. The crude product (7 g) was directly used in the subsequent reaction step.

c.1.2: 3-[4-(2-tert-Butyl-6-cyclobutyl-pyrimidin-4-yl)-piperazin-1-yl]-propan-1-ol 7 g of acetic acid 3-[4-(2-tert-butyl-6-cyclobutyl-pyrimidin-4-yl)-piperazin-1-yl]-propyl ester (18.7 mmol) and 0.67 g of lithium hydroxide (28.0 mmol) were stirred overnight in a mixture of 40 ml of tetrahydrofuran and 40 ml of water. The reaction mixture was partitioned between water and ethyl acetate. The organic layer was dried over magnesium sulfate, filtered, and the solvent was evaporated. The crude product was purified by chromatography on silica gel using dichloromethane-methanol (2%) as eluent to yield 2.5 g of the title compound as an oil that crystallized upon standing.

c.2 (R)-3-[4-(2-tert-Butyl-6-cyclobutyl-pyrimidin-4-yl)-piperazin-1-yl]-2-methyl-propan-1-ol c.2.1: (S)-(+)-1-Acetoxy-3-bromo-2-methyl-propane 5 g of (S)-(+)-3-bromo-2-methyl-1-propanol (32.6 mmol) were stirred in 5 ml of pyridine at room temperature. 3.67 g of acetic anhydride (35.9 mmol) were added and the reaction mixture was stirred for 3 h at 70° C. Stirring was continued for 16 h at room temperature. 30 ml of water and 40 ml of ethyl acetate were added. The organic layer was separated and washed with a further portion of water, then dried over magnesium sulfate, filtered, and evaporated under reduced pressure, whereby 4.34 g of the title compound were obtained.

$^1$H-NMR (CDCl$_3$): δ [ppm] 3.95-4.15 (m, 2H), 3.4 (m, 2H), 2.2 (m, 1H), 2.05 (s, 3H), 1.05 (d, 3H).

c.2.2: (R)-Acetic acid 3-[4-(2-tert-butyl-6-cyclobutyl-pyrimidin-4-yl)-piperazin-1-yl]-2-methyl-propyl ester 3.87 g of 2-tert-butyl-4-cyclobutyl-6-piperazin-1-yl-pyrimidine (14.1 mmol) were stirred in 30 ml of dimethylformamide at room temperature. 3.18 g of triethylamine (63.1 mmol), 0.235 g of sodium iodide (1.57 mmol), 3.01 g of (S)-(+)-1-acetoxy-3-bromo-2-methyl-propane (15.7 mmol) were added. The reaction mixture was stirred for 16 h at room temperature. Stirring was continued for 2 h at 95-105° C. The dimethylformamide was removed by evaporation under reduce pressure. The residue was partitioned between 100 ml of dichloromethane and 100 ml of water. The organic layer was separated, dried over magnesium sulfate and evaporated under reduced pressure to give the crude product as a brownish oil (5.81 g).

MS (ESI) m/z: 389.2 [M+H]$^+$ c.2.3: (R)-3-[4-(2-tert-Butyl-6-cyclobutyl-pyrimidin-4-yl)-piperazin-1-yl]-2-methyl-propan-1-ol 5.81 g of crude (R)-acetic acid 3-[4-(2-tert-butyl-6-cyclobutyl-pyrimidin-4-yl)-piperazin-1-yl]-2-methyl-propyl ester (asserted 14.1 mmol)) were stirred in 26.6 ml of ethanol. A solution of 2.83 g of sodium hydroxide in 6 ml of water was added and the reaction mixture was heated at 60-70° C. for 5 h. After cooling to room temperature, 50 ml of water and 50 ml of dichloromethane were added. The dichloromethane layer was separated and the aqueous was extracted with a further portion of dichloromethane. The combined dichloromethane extracts were washed with water, dried over magnesium sulfate, filtered and evaporated under vacuum to give an orange oil (4.0 g).

MS (ESI) m/z: 347.2 [M+H]$^+$ $^1$H-NMR (CDCl$_3$): δ [ppm] 6.1 (s, 1H), 5.8 (s, broad, 1H), 3.35-3.7 (several m, 7H), 2.75 (m, 2H), 2.45 (m, 4H), 2.15-2.35 (m, 5H), 2.0 (m, 1H), 1.9 (m, 1H), 1.35 (s, 9H), 0.75 (d, 3H).

c.3: (S)-3-[4-(2-tert-Butyl-6-cyclobutyl-pyrimidin-4-yl)-piperazin-1-yl]-2-methyl-propan-1-ol c.3.1: (R)-(−)-1-acetoxy-3-bromo-2-methyl-propane 6 g of (R)-(−)-3-bromo-2-methyl-1-propanol (39.2 mmol) were stirred in 6 ml of pyridine at room temperature. 4.08 g of acetic anhydride (43.1 mmol) were added and the reaction mixture was stirred for 4 h at 70° C. Stirring was continued for 16 h at room temperature. 40 ml of water and 60 ml of ethyl acetate were added to the reaction mixture. The organic layer was separated and washed with a further portion of water, then dried over magnesium sulfate, filtered, and evaporated under vacuum, whereby 6.03 g of the title compound were obtained.

$^1$H-NMR (CDCl$_3$): δ [ppm] 3.95-4.15 (m, 2H), 3.4 (m, 2H), 2.2 (m, 1H), 2.05 (s, 3H), 1.05 (d, 3H).

c.3.2: (S)-Acetic acid 3-[4-(2-tert-butyl-6-cyclobutyl-pyrimidin-4-yl)-piperazin-1-yl]-2-methyl-propyl ester 3.87 g of 2-tert-butyl-4-cyclobutyl-6-piperazin-1-yl-pyrimidine (14.1 mmol) were stirred in 30 ml of dimethylformamide at room temperature. 3.18 g of triethylamine (63.1 mmol), 0.235 g of sodium iodide (1.57 mmol), 2.96 g of (R)-(−)-1-acetoxy-3-bromo-2-methyl-propane (15.2 mmol) were added and the reaction mixture was stirred for 5 h at 95° C. The dimethylformamide was evaporated under reduced pressure. The residue was partitioned between 100 ml of dichloromethane and 100 ml of water. The organic layer was separated, dried over magnesium sulfate and evaporated under reduced pressure to give a brownish oil (5.64 g).

MS (ESI) m/z: 389.4 [M+H]$^+$ c.3.3: (S)-3-[4-(2-tert-Butyl-6-cyclobutyl-pyrimidin-4-yl)piperazin-1-yl]-2-methyl-propan-1-ol 5.64 g of crude (S)-acetic acid 3-[4-(2-tert-butyl-6-cyclobutyl-pyrimidin-4-yl)-piperazin-1-yl]-2-methyl-propyl ester (asserted 14.1 mmol) were stirred in 26.6 ml of ethanol. A solution of 2.83 g of sodium hydroxide in 6 ml of water was added and the reaction was heated at 60-70° C. for 5 h. After cooling to room temperature, 50 ml of water and 50 ml of dichloromethane were added. The dichloromethane layer was separated and the aqueous phase was extracted with a further portion dichloromethane. The combined dichloromethane extracts were washed with water, dried over magnesium sulfate, filtered and evaporated under vacuum to give an orange oil. The crude product was purified by flash column chromatography eluting with dichloromethane-methanol (9:1). The fractions containing the product were combined and evaporated to give an orange oil (2.76 g).

MS (ESI) m/z: 347.2 [M+H]$^+$ $^1$H-NMR (CDCl$_3$): δ [ppm] 6.1 (s, 1H), 5.8 (s, broad, 1H), 3.6-3.75 (m, 5H), 3.5 (m, 1H); 3.4 (m, 1H), 2.75 (m, 2H), 2.45 (m, 4H), 2.15-2.35 (m, 5H), 2.0 (m, 1H), 1.9 (m, 1H), 1.35 (s, 9H), 0.75 (d, 3H).

c.4 3-[4-(2-tert-Butyl-6-cyclopropyl-pyrimidin-4-yl)-piperazin-1-yl]-propan-1-ol c.4.1: Acetic acid 3-[4-(2-tert-butyl-6-cyclopropyl-pyrimidin-4-yl)-piperazin-1-yl]-propyl ester 2.9 g of 2-tert-Butyl-4-piperazin-1-yl-6-cyclopropyl-pyrimidine (11.1 mmol), 1.8 g acetic acid 3-chloro-propyl ester (13.2 mmol), 1.38 g of triethylamine (13.7 mmol), and a spatula tip of sodium iodide were dissolved in 50 ml of dimethylformamide and stirred for 8 h at 80° C. After cooling to room temperature, the dimethylformamide was evaporated. The reaction mixture was partitioned between water and ethyl acetate. The organic layer was dried over magnesium sulfate, filtered, and the solvent was evaporated. The crude product (3.7 g) was directly used in the subsequent reaction step.

c.4.2: 3-[4-(2-tert-Butyl-6-cyclopropyl-pyrimidin-4-yl)-piperazin-1-yl]-propan-1-ol 3.7 g of acetic acid 3-[4-(2-tert-butyl-6-cyclopropyl-pyrimidin-4-yl)-piperazin-1-yl]-propyl ester (10.2 mmol) and 0.4 g of lithium hydroxide (16.7 mmol) were stirred overnight in 20 ml of tetrahydrofuran and 20 ml of water. The reaction mixture was partitioned between water and ethyl acetate. The organic layer was dried over magnesium sulfate, filtered, and the solvent was evaporated. The crude product was purified by chromatography on silica gel using dichloromethane-methanol (0-8%) as eluent to yield 1.0 g of the title compound.

3-{4-[2-cyclopropyl-6-tert-butyl-pyrimidin-4-yl]-piperazin-1-yl}-propan-1-ol and 3-{4-[2-cyclobutyl-6-tert-butyl-pyrimidin-4-yl]-piperazin-1-yl}-propan-1-ol were prepared according the same methods as described for the other 3-[4-(2/6-substituted-butyl-pyrimidin-4-yl)-piperazin-1-yl]-propan-1-ols, starting from the corresponding pyrimidyl-piperazine intermediates.

d. Preparation of 5-[4-(2-tert-Butyl-6-cyclobutyl-pyrimidin-4-yl)-piperazin-1-yl]-pentan amidine hydrochloride d.1: 5-[4-(2-tert-Butyl-6-cyclobutyl-pyrimidin-4-yl)-piperazin-1-yl]-pentanimidic acid ethyl ester hydrochloride 1.5 g of 5-[4-(2-tert-butyl-6-cyclobutyl-pyrimidin-4-yl)-piperazin-1-yl]-pentanenitrile (4.22 mmol) were dissolved in 40 ml of dichloromethane and 0.4 g of dry ethanol (8.7 mmol). Gaseous hydrochloric acid was introduced into the solution until saturation at 0° C. The reaction was stirred for 15 h at room temperature and concentrated to dryness. The resulting crude product (2.18 g) was directly used in the next reaction step.

d.2: 5-[4-(2-tert-Butyl-6-cyclobutyl-pyrimidin-4-yl)-piperazin-1-yl]-pentan amidine hydrochloride 2.8 g of 5-[4-(2-tert-Butyl-6-cyclobutyl-pyrimidin-4-yl)-piperazin-1-yl]-pentanimidic acid ethyl ester hydrochloride (4.27 mmol) were dissolved in 60 ml of ethanol. Gaseous ammonia was introduced into the solution at room temperature. The resulting suspension was stirred for 15 h at room temperature, filtered, and the filtrate concentrated to dryness under reduced pressure. The remaining residue was treated with isopropanol, filtered, and the filtrate was concentrated to dryness. The oily residue crystallized upon standing and was further treated with diisopropyl ether and ethyl acetate and filtered to yield the product in 0.9 g yield.

MS (ESI) m/z: 373.5 [M+H]$^+$ e. Preparation of 3-Hydroxy-acrylic acid ethyl ester 5.4 g of sodium hydride (135 mmol; 60% in mineral oil) were washed oil-free with pentane. 60 ml of diethyl ether were added followed by addition of a mixture of 10 g of ethyl acetate (113.5 mmol) and 10.1 g of ethyl formate (136.3 mmol) in 20 ml of diethyl ether. Stirring was continued for 4 h at room temperature and then the reaction mixture was filtered. The precipitate was washed with diethyl ether and dried to yield 11.7 g of the title compound as a white solid.

f. Synthesis of 3-mercapto-4-methyl-triazoles f.1 4-Methyl-5-methoxymethyl-4H-[1,2,4]triazole-3-thiol 5 g of methoxy-acetic acid (55.5 mmol) were dissolved in 70 ml of dimethylformamide. 11.73 g of 1,1'-carbonyldiimidazol (72.3 mmol) were added in portions within 10 min. After 30 min. at room temperature 23 ml of pyridin were added. Then 5.84 g of 4-methyl-3-thiosemicarbazide (55.5 mmol) were added and the obtained solution was stirred at room temperature overnight, and for an additional 3 h at 100° C. The solvent was evaporated, the residue dissolved in 70 ml of saturated aqueous sodium chloride solution and 30 ml of water. The aqueous layer was extracted six times with 100 ml of ethyl acetate each, and the combined organic layers were dried over magnesium sulfate, filtered, and the solvent was evaporated to dryness to yield 17 g of the crude title compound, which was further purified by silica gel chromatography with ethyl acetate, thereby obtaining 7.1 g of the purified title compound.

MS (ESI) m/z: 160.1 [M+H]$^+$ f.2 4-Methyl-5-methyl-4H-[1,2,4]triazole-3-thiol 62.4 g of N,N'-carbonyldiimidazol (0.385 mol) were added in portions within 10 min. to a mixture of 22 g of acetic acid (0.366 mol) and 300 ml of dimethylformamide. The temperature rose from 22° C. to about 26° C. After the addition was completed, stirring was continued for 30 min. Then 38.5 g of 4-methyl-3-thiosemicarbazid (0.366 mol) and 100 ml pyridine were added. The reaction mixture was heated to 10° C. and stirred for 4 h at this temperature. Stirring was continued for 14 h at room temperature. The solvent was evaporated under reduced pressure. The residue was treated with 200 ml of isopropanol and 150 ml of ethyl acetate, and re-dissolved at 80° C. Crystallization of the product started during cooling to room temperature. 300 ml of isopropanol were added and the obtained suspension was stirred for 1 h at room temperature. The precipitate was collected by filtration, washed twice with 75 ml of isopropanol each and dried under vacuum at 40° C. to yield 20.4 g of the title compound.

MS (ESI) m/z: 130.1 [M+H]$^+$
$^1$H-NMR (DMSO): δ [ppm] 13.4 (s, broad, 1H), 3.4 (s, 3H), 2.3 (s, 3H)

f.3 4-Methyl-5-ethyl-4H-[1,2,4]triazole-3-thiol

The reaction was performed similar to the method described for the preparation 4-Methyl-5-methoxymethyl-4H-[1,2,4]triazole-3-thiol by reacting 16.4 g of N,N'-carbonyldiimidazol (0.101 mol) with 5 g of propionic acid (0.067 mol) and 14.2 g of 4-methyl-3-thiosemicarbazid (0.135 mol). Yield: 3.8 g MS (ESI) m/z: 144.1 [M+H]$^+$ f.4 4-Methyl-5-cyclobutyl-4H-[1,2,4]triazole-3-thiol 5 g of cyclobutyl carboxylic acid (49.9 mmol) were dissolved in 50 ml of dimethylformamide. Within 10 min. 12.15 g of 1,1'-carbonyldiimidazol (74.91 mmol) were added in portions. After stirring for 1 h at room temperature 23 ml of pyridin were added followed by the addition of 10.5 g of 4-methyl-3-thiosemicarbazide (99.88 mmol). The solution was stirred at room temperature for 72 h and then poured into 600 ml of ice water. Stirring was continued for 30 min. before the aqueous layer was extracted three times with 50 ml dichloromethane and three times with 50 ml ethyl acetate each. The combined organic layers were dried over magnesium sulfate, filtered, and the solvent was evaporated, thereby yielding 5.2 g of the crude title product which was used without further purification.

MS (ESI) m/z: 170.1 [M+H]$^+$

4-Methyl-5-propyl-4H-[1,2,4]triazole-3-thiol, 4-Methyl-5-isopropyl-4H-[1,2,4]triazole-3-thiol, 4-Methyl-5-butyl-4H-[1,2,4]triazole-3-thiol, 4-Methyl-5-tert-butyl-4H-[1,2,4] triazole-3-thiol, and 4-Methyl-5-cyclopropyl-4H-[1,2,4] triazole-3-thiol were prepared according to the procedures as described for compounds a.1 to a.4 above.

4-Methyl-4H-[1,2,4]triazole-3-thiol was purchased from Aldrich.

4-Methyl-5-trifluoromethyl-4H-[1,2,4]triazole-3-thiol was purchased from Acros.

II. Preparation of the Compounds I

Example 1

2-tert-Butyl-4-cyclobutyl-6-{4-[3-([1,3,4]thiadiazol-2-ylsulfanyl)-pronyl]-piperazin-1-yl}-pyrimidine 1.0 g of 2-tert-Butyl-4-[4-(3-chloro-propyl)-piperazin-1-yl]-6-cyclobutyl-pyrimidine (2.85 mmol), 0.37 g of [1,3,4] thiadiazol-2-thiol (3.1 mmol), 0.17 g of lithium hydroxide and a spatula tip of potassium iodide were dissolved in 30 ml of dimethylformamide. The mixture was stirred for 56 h at room temperature and then extracted with water and ethyl acetate. The organic layer was dried over magnesium sulfate, filtered, and concentrated to dryness. The residue was purified by chromatography on silica gel (dichloromethane as eluent) to yield 2.6 g of the title compound as an oily residue.

MS (ESI) m/z: 433.4 [M+H]$^+$ $^1$H-NMR (DMSO): δ [ppm] 9.5 (s, 1H), 6.4 (s, 1H), 3.6 (m, 4H), 3.35 (m, 3H), 2.4 (m, 6H), 2.25 (m, 2H), 2.15 (m, 2H), 1.95 (m, 3H), 1.85 (m, 1H), 1.25 (s, 9H).

Example 2

2-tert-Butyl-4-cyclobutyl-6-{4-[3-(5-methyl-[1,3,4] thiadiazol-2-ylsulfanyl)-propyl]-piperazin-1-yl}-pyrimidine hydrochloride Using the method of example 1, the title compound was prepared by reacting of 5-methyl-[1,3,4]thiadiazol-2-thiol with 2-tert-butyl-4-[4-(3-chloro-propyl)-piperazin-1-yl]-6-cyclobutyl-pyrimidine and converting the isolated compound into its hydrochloride salt.

MS (ESI) m/z: 447.4 [M+H]$^+$ $^1$H-NMR (DMSO): δ [ppm] 14.0 (s, br, 1H), 12.0 (s, br, 1H), 7.15 (s, 1H), 5.0 (m, br, 1H), 4.7 (m, br, 1H), 4.1 (m, br, 1H), 3.7 (s, br, 1H), 3.65 (m, 2H), 3.4 (m, 4H), 3.25 (m, 2H), 3.15 (m, 1H), 2.7 (s, 3H), 2.2-2.4 (m, 6H), 2.0 (m, 1H), 1.85 (m, 1H), 1.4 (s, 9H).

Example 3

2-{3-[4-(2-tert-Butyl-6-cyclobutyl-pyrimidin-4-yl)-piperazin-1-yl]-propylsulfanyl}-pyrimidin-4-ol fumarate 1.0 g of 2-tert-Butyl-4-[4-(3-chloro-propyl)-piperazin-1-yl]-6-cyclobutyl-pyrimidine (2.85 mmol), 0.38 g of 2-mercapto-pyrimidine-4-ol (2.97 mmol), 0.1 g of lithium hydroxide (4.18 mmol) and a spatula tip of potassium iodide were dissolved in 20 ml of dimethylformamide. The mixture was stirred at room temperature for 16 h and at 50° C. for 5 h. The reaction mixture was cooled to room temperature and extracted with ethyl acetate. The organic layer was dried over magnesium sulfate, filtered, and concentrated to dryness. The crude product was purified by chromatography on silica gel with dichloromethane/methanol (2-5%). Fractions containing the product were combined and the solvent was evaporated. The residue was dissolved in isopropanol. 144 mg of fumaric acid in isopropanol were added to precipitate the title compound as the fumarate salt. The precipitate was collected by filtration and dried to yield 0.3 g of the title product as a white solid.

MS (ESI) m/z: 443.2 [M+H]$^+$ $^1$H-NMR (DMSO): δ [ppm] 11.2 (s, broad, 1H), 7.85 (d, 1H), 6.6 (s, 2H, fumarate), 6.4 (s, 1H), 6.1 (d, 1H), 3.6 (m, 4H), 3.4 (m, 1H), 3.15 (m, 2H), 2.4-2.6 (m, 6H), 2.1-2.3 (m, 4H), 1.8-2.0 (m, 4H), 1.25 (s, 9H).

Example 4

2-tert-Butyl-4-cyclobutyl-6-{4-[3-(pyrimidin-2-yl-sulfanyl)-propyl]-piperazin-1-yl}-pyrimidine hydrochloride 0.4 g of 2-mercapto-pyrimidine (3.57 mmol) were dissolved in 20 ml of dimethylformamide. After addition of 0.09 g of lithium hydroxide (3.57 mmol) and 0.27 g of sodium iodide (1.78 mmol), the reaction mixture was stirred at 60° C. and 1.25 g of 2-tert-butyl-4-[4-(3-chloro-propyl)-piperazin-1-yl]-6-cyclobutyl-pyrimidine (3.57 mmol) were added in portions. The mixture was stirred at 60° C. for 1 h. After cooling, the dimethylformamide was evaporated and the residue was partitioned between 30 ml of ethyl acetate and half-saturated sodium chloride solution (15 ml of saturated aqueous sodium chloride solution and 15 ml of water). The aqueous phase was reextracted twice with ethyl acetate. The combined organic layers were dried over magnesium sulfate, filtered, and concentrated to dryness. The crude product was redissolved in 30 ml of ethyl acetate. The hydrochloride was formed by addition of 4 N hydrochloric acid in dioxane to yield 1.8 g of the title compound as a crystallized hydrochloride salt.

MS (ESI) m/z: 427.2 [M+H]$^+$

Example 5

2-tert-Butyl-4-cyclobutyl-6-{4-[3-(pyridin-4-ylsulfanyl)-propyl]-piperazin-1-yl}-pyrimidine hydrochloride 0.21 g of 4-mercapto-pyridine (1.8 mmol) were dissolved in 15 ml of dimethylformamide. After addition of 0.04 g of lithium hydroxide (1.8 mmol) and 0.13 g of sodium iodide (0.9 mmol), the reaction mixture was stirred at 70° C. and 0.63 g of 2-tert-butyl-4-[4-(3-chloro-propyl)-piperazin-1-yl]-6-cyclobutyl-pyrimidine (0.9 mmol) were added in portions. The mixture was stirred at 80° C. for 2 h, and after evaporation of dimethylformamide, partitioned between 20 ml of ethyl acetate and 15 ml of saturated aqueous sodium chloride solution and 15 ml of water. The aqueous phase was reextracted twice with ethyl acetate. The combined organic layers were dried over magnesium sulfate, filtered, and concentrated to dryness. The crude product was purified by chromatography on silica gel with ethyl acetate and ethyl acetate-methanol (9:1). Fractions containing the product were combined. After evaporation of the solvent, the residue was re-dissolved in 15 ml of ethyl acetate and 1 N solution of hydrochloric acid in diethyl ether was added. The precipitated hydrochloride salt was collected by filtration and dried to give 0.54 g of the title product.

MS (ESI) m/z: 426.2 [M+H]$^+$ $^1$H-NMR (DMSO): δ [ppm] 14.1 (s, br, 1H), 12.3 (s, br, 1H), 8.65 (d, 2H), 8.0 (d, 2H), 7.15 (s, 1H), 4.6-5.1 (m, br, 2H), 4.2 (m, 1H), 3.6-3.9 (m, br, 4H), 3.45 (m, 2H), 3.3 (m, 2H), 3.2 (m, br, 2H), 2.3 (m, br, 4H), 2.25 (m, 2H), 2.0 (m, 1H), 1.85 (m, 1H), 1.4 (s, 9H).

Example 6

2-tert-Butyl-4-cyclobutyl-6-{4-[3-(pyridin-2-ylsulfanyl)-propyl]-piperazine-1-yl}-pyrimidine hydrochloride 0.2 g of 2-mercapto-pyridine (1.8 mmol) were dissolved in 15 ml of dimethylformamide. After addition of 0.04 g of lithium hydroxide (1.8 mmol) and 0.13 g of sodium iodide (0.9 mmol), the reaction mixture was stirred at 70° C. and 0.63 g of 2-tert-butyl-4-[4-(3-chloro-propyl)-piperazin-1-yl]-6-cyclobutyl-pyrimidine (0.9 mmol) were added in portions. The mixture was stirred at 80° C. for 5 h, and, after evaporation of dimethylformamide, the residue was partitioned between 20 ml of ethyl acetate and 15 ml of saturated aqueous sodium chloride solution and 15 ml of water. The aqueous phase was re-extracted twice with ethyl acetate. The combined organic layers were dried over magnesium sulfate, filtered, and concentrated to dryness. The crude product was purified by chromatography on silica gel using dichloromethane, dichloromethane-ethyl acetate (7:3-1:1). Fractions containing the product were combined. After evaporation of the solvent, the residue was re-dissolved in 20 ml of ethyl acetate and a 1 N solution of hydrochloric acid in diethyl ether was added. The precipitated hydrochloride salt was collected by filtration and dried to give 0.47 g of the title compound.

MS (ESI) m/z: 427.4 [M+H]$^+$ $^1$H-NMR (DMSO): δ [ppm] 14.1 (s, br, 1H), 12.1 (s, br, 1H), 8.5 (m, 1H), 7.75 (m, 1H), 7.4 (m, 1H), 7.2 (m, 1H), 7.15 (s, 1H), 7.1-7.4 (s, br, 1H), 5.0 (m, br, 1H), 4.7 (m, br, 1H), 4.15 (m, 1H), 3.5-3.9 (m, br, 3H), 3.05-3.3 (m, br, 6H), 2.3 (m, br, 4H), 2.2 (m, 2H), 2.0 (m, 1H), 1.85 (m, 1H), 1.4 (s, 9H).

Example 7

2-tert-Butyl-4-cyclobutyl-6-{4-[3-(pyrimidin-4-yloxy)-propyl]-piperazin-1-yl}-pyrimidine 0.2 g of 4-hydroxy-pyrimidine (2.08 mmol) were dissolved in 15 ml of dimethylformamide. After addition of 0.58 g of potassium carbonate (4.16 mmol) and 0.73 g of 2-tert-butyl-4-[4-(3-chloro-propyl)-piperazin-1-yl]-6-cyclobutyl-pyrimidine (2.08 mmol), the mixture was stirred at 90° C. for 3 h. The dimethylformamide was removed under reduced pressure and the resulting residue was partitioned between 40 ml of ethyl acetate and 20 ml of water. The aqueous phase was re-extracted with ethyl acetate, the organic layers were combined, dried over magnesium sulfate, filtered, and concentrated to dryness. The crude product was purified by chromatography on silica gel with ethyl acetate-methanol (2-10%). Fractions containing the product were combined. The solvent was evaporated. The product crystallized upon standing (yield: 0.2 g).

MS (ESI) m/z: 411.5 [M+H]$^+$ $^1$H-NMR (DMSO): δ [ppm] 8.8 (s, 1H), 8.5 (d, 1H), 6.9 (d, 1H), 6.4 (s, 1H), 4.4 (m, 2H), 3.6 (m, br, 4H), 3.3-3.45 (m, 2H), 2.4 (m, 5H), 2.1-2.3 (m, 4H), 1.95 (m, 3H), 1.85 (m, 1H), 1.3 (s, 9H).

Example 8

2-tert-Butyl-4-cyclobutyl-6-{4-[3-(4-methyl-pyrimidin-2-ylsulfanyl)-propyl]-piperazin-yl-yl}-pyrimidine hydrochloride 0.4 g of 2-mercapto-4-methyl-pyrimidine hydrochloride (2.46 mmol) were dissolved in 20 ml of dimethylformamide. After addition of 0.12 g of lithium hydroxide (4.92 mmol) and 0.18 g of sodium iodide (1.23 mmol), the reaction mixture was stirred at 70° C. and 0.86 g of 2-tert-butyl-4-[4-(3-chloro-propyl)-piperazin-1-yl]-6-cyclobutyl-pyrimidine (2.46 mmol) were added in portions. The mixture was stirred at 70° C. for 1 h, and, after evaporation of dimethylformamide, the residue was partitioned between 20 ml of ethyl acetate and 15 ml of saturated aqueous sodium chloride solution and 15 ml of water. The aqueous phase was re-extracted twice with ethyl acetate. The combined organic layers were dried over magnesium sulfate, filtered, and concentrated to dryness. The crude product was purified by chromatography on silica gel using ethyl acetate as eluent. Fractions containing the product were combined. The solvent was evaporated, and the resulting residue re-dissolved in 20 ml of ethyl acetate. The hydrochloride salt was precipitated by addition of 1 N hydrochloric acid in diethyl ether. The precipitate was collected by filtration and dried to yield 1.02 g of the title compound.

MS (ESI) m/z: 441.6 [M+H]$^+$ $^1$H-NMR (DMSO): δ [ppm] 14.1 (s, br, 1H), 12.1 (s, br, 1H), 8.5 (d, 1H), 7.15 (s, 1H), 7.1 (d, 1H), 5.0 (m, 1H), 4.7 (m, 1H), 4.3-4.6 (m, br, 2H), 4.2 (m, 1H), 3.9 (m, 1H), 3.7 (m, 3H), 3.1-3.3 (m, br, 4H), 2.45 (s, 3H), 2.3 (m, br, 4H), 2.2 (m, br, 2H), 2.0 (m, 1H), 1.85 (m, 1H), 1.4 (s, 9H).

Example 9

2-tert-Butyl-4-cyclobutyl-6-{4-[3-(1-methyl-1H-tetrazol-5-ylsulfanyl)-propyl]-piperazin-1-yl}-pyrimidine 0.5 g of 2-tert-Butyl-4-[4-(3-chloro-propyl)-piperazin-1-yl]-6-cyclobutyl-pyrimidine (1.42 mmol) were dissolved in 15 ml of dimethylformamide. 0.18 g of 1-methyl-1H-tetrazole-5-thiol (1.56 mmol), 0.09 g of lithium hydroxide (3.76 mmol) and a spatula tip of potassium iodide were added. The mixture was stirred for 2 h at 60° C. After cooling to room temperature, the reaction mixture was partitioned between water and ethyl acetate. The ethyl acetate layer was dried over magnesium sulfate, filtered, and the solvent evaporated under vacuum. The resulting crude product was purified by column chromatography on silica gel using dichloromethane-methanol (1-5%). Fractions containing the product were combined and the solvent was evaporated under vacuum. The residue was treated with acetonitril, the solvent evaporated, whereby 0.3 g of the title compound were obtained as an oily residue.
MS (ESI) m/z: 430.2 [M+H]$^+$
$^1$H-NMR (DMSO): δ [ppm] 7.9 (s, 1H), 6.4 (s, 1H), 3.7 (s, 3H), 3.55 (m, 4H), 3.4 (m, 1H), 3.2 (m, 2H), 2.4 (m, 5H), 2.25 (m, 2H), 2.15 (m, 2H), 1.95 (m, 1H), 1.8-1.9 (m, 3H), 1.3 (s, 9H).

Example 10

N-{4-[4-(2-tert-Butyl-6-cyclobutyl-pyrimidin-4-yl)-piperazin-1-yl]-butyl}-4-fluoro-benzamide hydrochloride 0.45 g of 4-fluorobenzoic acid (3.21 mmol) and 0.98 g of triethylamine (9.7 mmol) were dissolved in 30 ml of dimethylformamide. At room temperature, 0.5 g of hydroxybenzotriazole (HOBt, 3.7 mmol), 1.2 g of 4-[4-(2-tert-butyl-6-cyclobutyl-pyrimidin-4-yl)-piperazin-1-yl]-butylamine (3.47 mmol), and 0.7 g of N-ethyl-N'-(3-dimethylaminopropyl)-carbodiimide hydrochloride (EDCl, 3.65 mmol) were added and the mixture was stirred for 68 h. The reaction mixture was partitioned between water and ethyl acetate. The organic phase was dried over magnesium sulfate, filtered, and concentrated to dryness. The crude product was purified by chromatography on silica gel using dichloromethane-methanol (2%). The oily residue was re-dissolved in isopropanol and 1 N hydrochloric acid in diisopropyl ether was added. The resulting precipitate was filtered and dried to yield 1.2 g of the title compound.
MS (ESI) m/z: 468.4 [M+H]$^+$
$^1$H-NMR (CDCl$_3$): δ [ppm] 8.0 (m, 2H), 7.65 (m, broad, 1H), 7.05 (m, 2H), 6.2 (s, 1H), 4.0 (m, broad, 4H), 3.7 (m, broad, 1H), 3.5 (m, 2H), 3.05 (m, broad, 4H), 2.95 (m, broad, 2H), 2.2-2.4 (m, 4H), 2.0 (m, 1H), 1.8-1.95 (m, 3H), 1.75 (m, 2H), 1.4 (s, 9H).

Example 11

N-{4-[4-(2-tert-Butyl-6-cyclobutyl-pyrimidin-4-yl)-piperazin-1-yl]-butyl}-isonicotinamide hydrochloride 0.35 g of isonicotinic acid (2.84 mmol) and 0.87 g of triethylamine (8.62 mmol) were dissolved in 30 ml of dimethylformamide. 0.45 g of hydroxybenzotriazole (HOBt, 3.33 mmol), 1.1 g of 4-[4-(2-tert-butyl-6-cyclobutyl-pyrimidin-4-yl)-piperazin-1-yl]-butylamine (3.18 mmol), and 0.6 g of N-ethyl-N'-(3-dimethylaminopropyl)-carbodiimide hydrochloride (EDCl, 3.13 mmol) were added at room temperature, and the reaction mixture was stirred for 16 h. The reaction mixture was then partitioned between water and ethyl acetate. The organic phase was dried over magnesium sulfate, filtered, and concentrated to dryness. The crude product was purified by chromatography on silica gel using dichloromethane-methanol (2-10%). The oily residue was re-dissolved in isopropanol, and 1 N hydrochloric acid in diisopropyl ether was added. The mixture was slowly evaporated to yield 1.0 g of the title compound as a yellowish foam.
MS (ESI) m/z: 451.5 [M+H]$^+$
$^1$H-NMR (DMSO): δ [ppm] 13.8 (s, broad, 1H), 11.85 (s, broad, 1H), 9.45 (m, 1H), 8.95 (m, 2H), 8.25 (m, 2H), 7.1 (s, 1H), 4.5-5.1 (m, broad, 2H), 4.05 (m, 1H), 3.55-3.9 (m, broad, 4H), 3.35 (m, 2H), 3.1-3.25 (m, 3H), 2.25-2.4 (m, 4H), 2.0 (m, 1H), 1.85 (m, 3H), 1.65 (m, 2H), 1.4 (s, 9H).

Example 12

N-{4-[4-(2-tert-Butyl-6-cyclobutyl-pyrimidin-4-yl)-piperazin-1-yl]-butyl}-nicotinamide 0.35 g of nicotinic acid (2.84 mmol) and 0.87 g of triethylamine (8.62 mmol) were dissolved in 30 ml of dimethylformamide. 0.45 g of hydroxybenzotriazole (HOBt, 3.33 mmol), 1.1 g of 4-[4-(2-tert-butyl-6-cyclobutyl-pyrimidin-4-yl)-piperazin-1-yl]-butylamine (3.18 mmol), and 0.6 g of N-ethyl-N'-(3-dimethylaminopropyl)-carbodiimide hydrochloride (EDCl, 3.13 mmol) were added at room temperature, and the reaction mixture was stirred for 16 h. The reaction mixture was partitioned between water and ethyl acetate. The organic phase was dried over magnesium sulfate, filtered, and concentrated to dryness. The crude product was purified by chromatography on silica gel using dichloromethane-methanol (2-10%). The residue was treated with acetonitrile, filtered and dried to yield 0.75 g of the title compound as a white solid.
MS (ESI) m/z: 451.5 [M+H]$^+$
$^1$H-NMR (DMSO): δ [ppm] 9.0 (m, 1H), 8.7 (m, 1H), 8.65 (t, 1H), 8.15 (m, 1H), 7.5 (m, 1H), 6.4 (s, 1H), 3.6 (m, 4H), 3.4 (m, 1H), 3.3 (m, 4H), 2.4 (m, 3H), 2.35 (m, 1H), 2.25 (m, 1H), 2.15 (m, 2H), 1.95 (m, 1H), 1.85 (m, 1H), 1.5-1.6 (m, 4H), 1.3 (s, 9H).

Example 13

Pyridine-2-carboxylic acid {4-[4-(2-tert-butyl-6-cyclobutyl-pyrimidin-4-yl)-piperazin-1-yl]-butyl}-amide hydrochloride 0.28 g of picolic acid (2.32 mmol) and 0.8 g of 4-[4-(2-tert-butyl-6-cyclobutyl-pyrimidin-4-yl)-piperazin-1-yl]-butylamine (2.32 mmol) were dissolved in 30 ml of dichloromethane. After addition of 1.19 g of diisopropylethylamine (9.26 mmol), 0.155 g of hydroxybenzotriazole (HOBt, 1.15 mmol), and 0.487 g of N-ethyl-N'-(3-dimethylaminopropyl)-carbodiimide hydrochloride (EDCl, 2.54 mmol) at 0° C., the reaction mixture was stirred for 16 h at room temperature. 0.24 g of N-Ethyl-N'-(3-dimethylaminopropyl)-carbodiimide hydrochloride were added and the reaction mixture was stirred for 5 h. 100 ml of dichloromethane were added. The organic layer was washed twice with water. The dichlormethane phase was dried over magnesium sulfate, filtered, and concentrated to dryness. The crude product was purified by chromatography on silica gel using ethyl acetate as eluent. The residue was re-dissolved in 15 ml of diethylether and treated with 1 N hydrochloric acid in diethyl ether. The precipitate was collected by filtration to yield 0.95 g of the title compound as a hydrochloride salt.
MS (ESI) m/z: 451.2 [M+H]$^+$
$^1$H-NMR (DMSO): δ [ppm] 14.1 (s, br, 1H), 12.0 (s, br. 1H), 8.9 (m, 1H), 8.65 (m, 1H), 8.8 (m, 2H), 7.6 (m, 1H), 7.15 (s, 1H), 5.0 (m, 1H), 4.7 (m, 1H), 4.15 (m, 2H), 3.85 (m, 1H), 3.55-3.8 (m, 3H), 3.35 (m, 2H), 3.05-3.25 (m, br, 3H), 2.2-2.4 (m, br, 4H), 2.0 (m, 1H), 1.8 (m, br, 3H), 1.6 (m, 2H), 1.4 (s, 9H).

Example 14

Pyrazine-2-carboxylic acid {4-[4-(2-tert-butyl-6-cyclobutyl-pyrimidin-4-yl)-piperazin-1-yl]-butyl}-amide 0.28 g of 2-pyrazinecarboxylic acid (2.26 mmol) and 0.78 g of 4-[4-(2-tert-butyl-6-cyclobutyl-pyrimidin-4-yl)-piperazin-1-yl]-butylamine (2.27 mmol) were dissolved in 30 ml of dichloromethane. Addition of 1.19 g of diisopropylethylamine (9.26 mmol), 0.155 g of hydroxybenzotriazole (HOBt, 1.15 mmol), and 0.487 g of N-ethyl-N'-(3-dimethylaminopropyl)-carbodiimide hydrochloride (EDCl, 2.54 mmol) at 0° C. was followed by stirring for 16 h at room temperature. After the addition of 0.24 g of N-ethyl-N'-(3-dimethylaminopropyl)-carbodiimide hydrochloride the mixture was stirred for further 4 h. 50 ml of dichloromethane were added. The organic layer was washed with water and saturated aqueous sodium chloride. The dichloromethane phase was dried over magnesium sulfate, filtered, and concentrated to dryness. The crude product was purified by chromatography on silica gel using ethyl acetate and ethyl acetate-methanol (5%). Evaporation of the solvent yielded 0.568 g of the title compound as a white solid.

MS (ESI) m/z: 452.2 [M+H]$^+$ $^1$H-NMR (DMSO): δ [ppm] 9.2 (s, 1H), 8.95 (t, 1H), 8.85 (s, 1H), 8.7 (s, 1H), 6.4 (s, 1H), 3.6 (m, br, 4H), 3.3-3.45 (m, 3H), 2.4 (m, 3H), 2.3 (m, 2H), 2.25 (m, 2H), 2.15 (m, 2H), 1.95 (m, 1H), 1.85 (m, 1H), 1.55 (m, 2H), 1.45 (m, 2H), 1.25 (s, 9H).

Example 15

Pyrimidine-5-carboxylic acid {4-[4-(2-tert-butyl-6-cyclobutyl-pyrimidin-4-yl)-piperazin-1-yl]-butyl}-amide 0.1 g of pyrimidine-5-carboxylic acid (0.805 mmol) and 0.28 g of 4-[4-(2-tert-butyl-6-cyclobutyl-pyrimidin-4-yl)-piperazin-1-yl]-butylamine (0.805 mmol) were dissolved in 10 ml of dichloromethane. 0.46 g of diisopropylethylamine (3.17 mmol), 0.054 g of hydroxybenzotriazole (HOBt, 0.4 mmol), and 0.17 g of N-ethyl-N'-(3-dimethylamino-propyl)-carbodiimide hydrochloride (EDCl, 0.88 mmol) were added at 0° C. The reaction mixture was stirred for 16 h at room temperature. Then, 0.085 g of N-ethyl-N'-(3-dimethylamino-propyl)-carbodiimide hydrochloride were added and the reaction mixture was stirred for 4 h. The solvent was evaporated and the residue partitioned between and ethyl acetate and saturated aqueous sodium chloride. 4 ml of acetone were added to improve phase separation. The organic phase was dried over magnesium sulfate, filtered, and concentrated to dryness. The crude product was purified by chromatography on silica gel using ethyl acetate and ethyl acetate-methanol (5-10%). Evaporation of the solvent yielded 0.16 g of the title compound as a white solid.

MS (ESI) m/z: 452.2 [M+H]$^+$ $^1$H-NMR (DMSO): δ [ppm] 9.3 (s, 1H), 9.2 (s, 2H), 8.7 (t, 1H), 6.4 (s, 1H), 3.5-3.65 (m, br, 4H), 3.25-3.45 (m, 4H), 2.4 (m, 3H), 2.35 (m, 2H), 2.1-2.3 (m, 3H), 1.95 (m, 1H), 1.85 (m, 1H), 1.5-1.65 (m, 4H), 1.3 (s, 9H).

Example 16

N-{4-[4-(2-tert-Butyl-6-cyclobutyl-pyrimidin-4-yl)-piperazin-1-yl]-butyl}-4-nitro-benzamide 0.91 g of 4-[4-(2-tert-Butyl-6-cyclobutyl-pyrimidin-4-yl)piperazin-1-yl]-butylamine (2.64 mmol) and 0.53 g of triethylamine (5.28 mmol) were dissolved in 20 ml of tetrahydrofuran. 0.49 g of 4-nitro-benzoyl-chloride (2.64 mmol) were added at 0-5° C. After stirring for 2 h at 0-5° C., the solvent was evaporated and the residue partitioned between ethyl acetate and water. The aqueous phase was re-extracted with ethyl acetate, and the combined organic layers were dried over magnesium sulfate, filtered, and concentrated to dryness. The crude product was purified by chromatography on silica gel using ethyl acetate and ethyl acetate-methanol (2%). Fractions containing the product were combined. The solvent was evaporated to yield 0.51 g of the title compound as a solid.

MS (ESI) m/z: 495.4 [M+H]$^+$ $^1$H-NMR (DMSO): δ [ppm] 8.7 (t, 1H, NH), 8.3 (d, 2H), 8.1 (d, 2H), 6.4 (s, 1H), 3.5-3.65 (br, 4H), 3.4 (m, 1H), 3.2-3.35 (m, br, 2H), 2.4 (m, br, 4H), 2.1-2.4 (several m, 6H), 1.95 (m, 1H), 1.85 (m, 1H), 1.4-1.6 (m, 4H), 1.35 (s, 9H).

Example 17

Pyridazine-4-carboxylic acid {4-[4-(2-tert-butyl-6-cyclobutyl-pyrimidin-4-yl)-piperazin-1-yl]-butyl}-amide hydrochloride 0.25 g of 4-pyridazine-carboxylic acid (2.01 mmol) and 0.7 g of 4-[4-(2-tert-butyl-6-cyclobutyl-pyrimidin-4-yl)-piperazin-1-yl]-butylamine (2.01 mmol) were dissolved in 25 ml of dichloromethane. 1.04 g of diisopropylethylamine (8.04 mmol), 0.19 g of hydroxybenzotriazole (HOBt, 1.4 mmol), and 0.46 g of N-ethyl-N'-(3-dimethylaminopropyl)-carbodiimide hydrochloride (EDCl, 2.4 mmol) were added at 0° C. and the reaction mixture was stirred for 16 h at room temperature. 0.09 g of hydroxybenzotriazole and 0.23 g of N-ethyl-N'-(3-dimethylaminopropyl)-carbodiimide hydrochloride were added and the reaction mixture was stirred 5 h. 25 ml of dichloromethane were added, the organic layer was washed with aqueous saturated sodium chloride, the aqueous phase re-extracted once with dichloromethane. The combined organic phases were dried over magnesium sulfate, filtered, and concentrated to dryness. The crude product was purified by chromatography on silica gel using ethyl acetate and ethyl acetate-methanol (10%). Fractions containing the product were combined, the solvent evaporated, and the residue re-dissolved in 20 ml of ethyl acetate. Treatment with 3.3 ml of 1 N hydrochloride acid in diethyl ether yielded 0.69 g of the title compound as a white solid.

MS (ESI) m/z: 452.4 [M+H]$^+$ $^1$H-NMR (DMSO): δ [ppm] 13.9 (s, broad, 1H), 11.85 (s, broad, 1H), 9.65 (s, 1H), 9.45 (m, 2H), 8.2 (m, 1H), 7.15 (s, 1H), 5.0 (m, broad, 1H), 4.7 (m, broad, 1H), 4.1 (m, 1H), 3.85 (m, 1H), 3.65 (m, 3H), 3.35 (m, 2H), 3.2 (m, broad, 4H), 2.35 (m, broad, 4H), 1.85 (m, broad, 3H), 1.65 (m, 2H), 1.4 (s, 9H).

Example 18

N-{4-[4-(2-tert-Butyl-6-cyclobutyl-pyrimidin-4-yl)-piperazin-1-yl]-butyl}-2-fluoro-benzamide 0.29 g of 2-fluoro-benzoic acid (2.03 mmol) and 0.7 g of 4-[4-(2-tert-butyl-6-cyclobutyl-pyrimidin-4-yl)-piperazin-1-yl]-butylamine (2.03 mmol) were dissolved in 25 ml of dichloromethane. 1.04 g of diisopropylethylamine (8.04 mmol), 0.19 g of hydroxybenzotriazole (HOBt, 1.4 mmol), and 0.46 g of N-ethyl-N'-(3-dimethylaminopropyl)-carbodiimide hydrochloride (EDCl, 2.4 mmol) were added at 0° C. and the reaction mixture was stirred for 16 h at room temperature. 25 ml of dichloromethane were added, the organic layer washed with aqueous saturated sodium chloride, the aqueous phase re-extracted once with dichloromethane, and the combined organic phases were dried over magnesium sulfate, filtered, and concentrated to dryness. The crude product was purified by chromatography on silica gel using ethyl acetate and ethyl acetate-methanol (5%). Fractions containing the product were combined. The solvent was evaporated to yield 0.84 g of the title compound as a white solid.

MS (ESI) m/z: 468.4 [M+H]$^+$ $^1$H-NMR (DMSO): δ [ppm] 8.3 (t, 1H, NH), 7.6 (m, 1H), 7.5 (m, 1H), 7.25 (m, 2H), 6.4 (s, 1H), 3.6 (m, br, 4H), 3.4 (m, 1H), 3.3 (m, 2H), 2.4 (m, br, 4H), 2.3 (m, 2H), 2.25 (m, 2H), 2.15 (m, 2H), 1.95 (m, 1H), 1.8 (m, 1H), 1.45-1.6 (m, 4H), 1.3 (s, 9H).

Example 19

N-{4-[4-(2-tert-Butyl-6-cyclobutyl-pyrimidin-4-yl)-piperazin-1-yl]-butyl}-3-fluoro-benzamide 0.29 g of 3-fluoro-benzoic acid (2.03 mmol) and 0.7 g of 4-[4-(2-tert-Butyl-6-cyclobutyl-pyrimidin-4-yl)-piperazin-1-yl]-butylamine (2.03 mmol) were dissolved in 25 ml of dichloromethane. Addition of 1.04 g of diisopropylethylamine (8.04 mmol), 0.19 g of hydroxybenzotriazole (HOBt, 1.4 mmol), and 0.46 g of N-ethyl-N'-(3-dimethylaminopropyl)-carbodiimide hydrochloride (EDCl, 2.4 mmol) at 0° C. was followed by stirring the reaction mixture for 16 h at room temperature. 30 ml of dichloromethane were added, the organic layer was washed with aqueous saturated sodium chloride. The aqueous phase was re-extracted once with dichloromethane. The combined organic phases were dried over magnesium sulfate, filtered, and concentrated to dryness. The crude product was purified by chromatography on silica gel using ethyl acetate and ethyl acetate-methanol (15:1). Fractions containing the product were combined, the solvent was evaporated to yield 0.88 g of the title compound as a white solid.

MS (ESI) m/z: 468.4 [M+H]$^+$ $^1$H-NMR (DMSO): δ [ppm] 8.55 (t, 1H, NH), 7.7 (d, 1H), 7.65 (m, 1H), 7.5 (m, 1H), 7.35 (m, 1H), 6.4 (s, 1H), 3.6 (m, br, 4H), 3.4 (m, 1H), 3.3 (m, 2H), 2.4 (m, br, 4H), 2.3 (m, 2H), 2.25 (m, 2H), 2.15 (m, 2H), 1.95 (m, 1H), 1.8 (m, 1H), 1.45-1.6 (m, 4H), 1.3 (s, 9H).

Example 20

N-{4-[4-(2-tert-Butyl-6-cyclobutyl-pyrimidin-4-yl)-piperazin-1-yl]-butyl}-4-fluoro-N-methyl-benzamide hydrochloride 0.5 g of 4-fluorobenzoic acid (3.57 mmol) and 1.27 g of triethylamine (12.57 mmol) were dissolved in 40 ml of dimethylformamide. 0.5 g of hydroxybenzotriazole (HOBt, 3.7 mmol), 1.3 g of {4-[4-(2-tert-Butyl-6-cyclobutyl-pyrimidin-4-yl)-piperazin-1-yl]-butyl}-methyl-amine hydrochloride (2.77 mmol), and 0.75 g of N-ethyl-N'-(3-dimethylaminopropyl)-carbodiimide hydrochloride (EDCl, 3.91 mmol) were added at room temperature, and the reaction mixture was stirred for 16 h. The reaction mixture was partitioned between water and ethyl acetate, the organic phase dried over magnesium sulfate, filtered, and concentrated to dryness. The crude product was purified by chromatography on silica gel using dichloromethane-methanol (2%). The residue was re-dissolved in isopropanol, treated with 4 N hydrochloric acid in dioxan. The precipitate was collected by filtration and dried to yield 0.6 g of the title compound as a white solid.

MS (ESI) m/z: 482.4 [M+H]$^+$ $^1$H-NMR (DMSO): δ [ppm] 14.1 (s, broad, 1H), 12.1 (s, broad, 1H), 7.5 (m, broad, 2H), 7.25 (m, 2H), 7.15 (s, 1H), 5.0 (m, broad, 1H), 4.7 (m, broad, 1H), 4.4 (m, broad, 1H), 4.15 (m, 1H), 3.85 (m, 1H), 3.55-3.75 (m, broad, 3H), 3.5 (m, 1H), 3.2 (m, broad, 4H), 2.95 (broad, 3H), 2.3 (broad, 4H), 2.0 (m, 1H), 1.85 (broad, 2H), 1.55-1.7 (broad, 3H), 1.4 (s, 9H).

Example 21

6-{3-[4-(2-tert-Butyl-6-cyclobutyl-pyrimidin-4-yl)-piperazin-1-yl]-propoxy}-pyrimidin-4-ol 1.5 g of 2-tert-Butyl-4-[4-(3-chloro-propyl)-piperazin-1-yl]-6-cyclobutyl-pyrimidine (4.27 mmol), 0.72 g of pyrimidine-4,6-diol (6.4 mmol) and 1.31 g of triethylamine in 30 ml of dimethylformamide were stirred for 16 h at 80° C. The mixture was extracted with water and ethyl acetate. The organic layer was dried over magnesium sulfate, filtered, and concentrated to dryness. The crude product was purified by chromatography on silica gel using dichloromethane-methanol (1-10%). Fractions containing the product were combined. The solvents were evaporated and the oily residue was treated with acetonitrile. The precipitate was collected by filtration and dried to yield 0.27 g of the title compound.

MS (ESI) m/z: 427.2 [M+H]$^+$ $^1$H-NMR (DMSO): δ [ppm] 8.1 (s, 1H), 6.4 (s, 1H), 5.5 (s, 1H), 4.15 (m, 2H), 3.6 (m, 4H), 3.4 (m, 2H), 2.4 (m, 6H), 2.25 (m, 2H), 2.15 (m, 2H), 1.95 (m, 1H), 1.85 (m, 2H), 1.8 (m, 1H), 1.3 (s, 9H).

Example 22

2-tert-Butyl-4-cyclobutyl-6-{4-[3-(2-methylsulfanyl-pyrimidin-4-yloxy)-propyl]-piperazin-1-yl}-pyrimidine 0.36 g of sodium hydride (9 mmol, 60% in paraffin) were washed oil-free with pentane before 1.5 g of 3-[4-(2-tert-butyl-6-cyclobutyl-pyrimidin-4-yl)-piperazin-1-yl]-propan-1-ol (4.5 mmol) dissolved in 20 ml of dioxane were added. The reaction was heated to reflux for 1 h. After cooling, 0.75 g of 4-chloro-2-methylsulfanyl-pyrimidine (4.67 mmol) dissolved in 10 ml of dioxane were added. The reaction mixture was stirred under reflux for 2 h. The reaction mixture was partitioned between water and ethyl acetate. The organic layer was extracted with 5% aqueous citric acid, the pH of the aqueous phase was adjusted to basic pH with 2 N sodium hydroxide solution. The aqueous layer was re-extracted with ethyl acetate, the organic layer was dried over magnesium sulfate, filtered, and the solvent was evaporated to yield 1.75 g of the title compound as a yellowish oil.

MS (ESI) m/z: 457.2 [M+H]$^+$

Example 23

2-tert-Butyl-4-cyclobutyl-6-{4-[3-(2-methanesulfinyl-pyrimidin-4-yloxy)-propyl]-piperazin-1-yl}-pyrimidine 0.7 g of 2-tert-bButyl-4-cyclobutyl-6-{4-[3-(2-methylsulfanyl-pyrimidin-4-yloxy)-propyl]-piperazin-1-yl}-pyrimidine (1.53 mmol) were dissolved in 50 ml of methanol and 60 ml of water. 2.8 g of (4.56 mmol) oxone were added in portions at 0-5° C. The reaction mixture was stirred for 1 h at 5° C. before a spatula tip of sodium pyrosulfite was added. After stirring for 5 min, the reaction mixture was poured onto water and the aqueous phase was adjusted to pH 9 with saturated aqueous sodium carbonate solution. After extraction with dichloromethane, the organic phase was dried over magnesium sulfate, filtered and the solvent was evaporated under reduced pressure to yield 0.8 g of the crude sulfoxide compound that was directly used in the next reaction step.
MS (ESI) m/z: 473.2 [M+H]+

Example 24

4-{3-[4-(2-tert-Butyl-6-cyclobutyl-pyrimidin-4-yl)-piperazin-1-yl]-propoxy}-pyrimidin-2-ol Route a:
0.8 g of 2-tert-Butyl-4-cyclobutyl-6-{4-[3-(2-methane-sulfinyl-pyrimidin-4-yloxy)-propyl]-piperazin-1-yl}-pyrimidine (1.7 mmol) were dissolved in 15 ml of acetone and 100 ml of aqueous 1 N sodium hydroxide were added. The reaction mixture was stirred for 5 h at room temperature. The reaction mixture was partitioned between water and dichloromethane. The organic layer was dried over magnesium sulfate, filtered, and the solvent evaporated under reduced pressure to yield an oily residue that crystallized after addition of acetonitrile. Recrystallization with acetonitrile yielded 0.07 g of the title compound.
MS (ESI) m/z: 427.2 [M+H]+
Route b:
0.5 g of 2-tert-Butyl-4-cyclobutyl-6-{4-[3-(2-methane-sulfinyl-pyrimidin-4-yloxy)-propyl]-piperazin-1-yl}-pyrimidine (1.1 mmol) were dissolved in 3.8 ml of acetic acid. 1.2 g of aqueous hydrogen peroxide (10.6 mmol, 30% in water) were added at 0° C. The reaction mixture was stirred for 15 h at room temperature, poured onto water. The aqueous reaction mixture was adjusted to alkaline pH with saturated sodium bicarbonate solution. After addition of ethyl acetate, a precipitate formed that was filtered and dried to yield 0.2 g of the title compound.
MS (ESI) m/z: 427.2 [M+H]+
1H-NMR (DMSO): δ [ppm] 7.65 (m, 2H), 6.4 (s, 1H), 5.8 (m, 1H), 4.25 (m, 2H), 3.35-3.65 (m, 6H), 2.4 (m, 4H), 2.25 (m, 2H), 2.15 (m, 2H), 1.95 (m, 1H), 1.7-1.8 (m, 3H), 1.35 (s, 9H).

Example 25

4-{4-[3-(4-Benzyloxy-pyrimidin-2-yloxy)-propyl]-piperazin-1-yl}-2-tert-butyl-6-cyclobutyl-pyrimidine 0.9 g of 3-[4-(2-tert-butyl-6-cyclobutyl-pyrimidin-4-yl)-piperazin-1-yl]-propan-1-ol (2.71 mmol) were dissolved in 20 ml of tetrahydrofuran. 2.75 ml of n-butyllithium (15% in hexane) were added at 0° C. The reaction mixture was stirred for 30 min. 0.79 g of 4-benzyloxy-2-methanesulfonyl-pyrimidine (3.0 mmol) dissolved in 10 ml of tetrahydrofuran were then added. The reaction mixture was stirred overnight at room temperature and for an additional 6 h at 60° C. The reaction mixture was partitioned between water and ethyl acetate. The organic layer was dried over magnesium sulfate, filtered, and the solvent was evaporated. The crude product was purified by chromatography on silica gel using dichloromethane-methanol (1.5%) as eluent to yield 0.75 g of the title compound.

Example 26

2-{3-[4-(2-tert-Butyl-6-cyclobutyl-pyrimidin-4-yl)-piperazin-1-yl]-propoxy}-pyrimidin-4-ol 0.75 g of 4-{4-[3-(4-benzyloxy-pyrimidin-2-yloxy)-propyl]-piperazin-1-yl}-2-tert-butyl-6-cyclobutyl-pyrimidine (1.45 mmol) were dissolved in 20 ml of tetrahydrofuran and, after addition of 0.1 g of 10% Pd/C, the reaction mixture was hydrogenated for 3 h at 40° C. After filtration, additional catalyst (0.2 g of 10% Pd/C) was added and the mixture was again hydrogenated for 1 h at 40° C. Finally, the catalyst was removed by filtration, the solvent evaporated under reduced pressure, and the remaining oil crystallized by addition of acetonitril to yield 0.37 g of the title compound.
MS (ESI) m/z: 427.2 [M+H]+
1H-NMR (DMSO): δ [ppm] 12.3 (s, 1H), 7.7 (d, 1H), 6.4 (d, 1H), 5.9 (d, 1H), 4.3 (m, 2H), 3.6 (m, 4H), 3.4 (m, 1H), 2.4 (m, 6H), 2.25 (m, 2H), 2.15 (m, 2H), 1.95 (m, 1H), 1.85 (m, 2H), 1.8 (m, 1H), 1.3 (s, 9H).

Example 27

2-tert-Butyl-4-cyclobutyl-6-{4-[3-(pyrimidin-2-yloxy)-propyl]-piperazin-1-yl}-pyrimidine hydrochloride 0.31 g of sodium hydride (7.8 mmol; 60% in paraffin) was washed oil-free with pentane before 1.3 g of 3-[4-(2-tert-butyl-6-cyclobutyl-pyrimidin-4-yl)-piperazin-1-yl]-propan-1-ol (3.91 mmol) dissolved in 20 ml of dioxane were added. The reaction was heated to reflux for 1 h. After cooling, 0.7 g of 2-chloro-pyrimidine (6.11 mmol) dissolved in 10 ml of dioxane were added. The reaction mixture was heated under reflux for 2 h. The reaction mixture was partitioned between water and ethyl acetate. The organic layer was dried over magnesium sulfate, filtered, the solvent evaporated, and the residue re-dissolved in isopropanol and treated with hydrochloric acid in diethyl ether. After removing most of the organic phase, the residue was treated with isopranol/diisopropyl ether, which, after cautious evaporation, yielded 1.6 g of the title compound.
MS (ESI) m/z: 411.1 [M+H]+
1H-NMR (DMSO): δ [ppm] 14.0 (s, broad, 1H), 12.1 (s, broad, 1H), 8.6 (m, 2H), 7.15 (m, 2H), 5.0 (m, broad, 1H), 4.7 (m, broad, 1H), 4.4 (m, 2H), 4.0-4.3 (m, broad, 4H), 3.6-3.9 (m, broad, 3H), 3.1-3.3 (m, broad, 4H), 2.2-2.4 (m, broad, 6H), 2.0 (m, 1H), 1.9 (m, 1H), 1.4 (s, 9H).

Example 28

(R)-2-tert-Butyl-4-cyclobutyl-6-{4-[2-methyl-3-(pyrimidin-2-yloxy)-propyl]-piperazin-1-yl}-pyrimidine hydrochloride 0.755 g of (R)-3-[4-(2-tert-butyl-6-cyclobutyl-pyrimidin-4-yl)-piperazin-1-yl]-2-methyl-propan-1-ol (2.18 mmol) were stirred in 7.6 ml of dimethylformamide under argon. 0.105 g of 60% sodium hydride (2.6 mmol) were added and stirred for 10 min. A solution of 0.275 g of 2-chloro-pyrimidine (2.4 mmol) in 2.4 ml of dimethylformamide was added. The reaction mixture was stirred for 16 h, followed by the addition of 30 ml of water and 40 ml of ethyl acetate. The organic layer was separated and the aqueous phase extracted with a further portion of ethyl acetate. The combined extracts were concentrated to dryness and the crude product purified by flash column chromatography eluting with ethyl acetate. The fractions containing the product were combined and evaporated under reduced pressure to give a pale yellow oil. The oil was dissolved in tert-butyl methylether and 4 N hydrochloric acid in dioxan was added to the solution. A white solid separated. The precipitate was collected by filtration, washed with tert-butyl methyl ether and dried in a vacuum oven to yield 0.42 g of the title compound.

MS (ESI) m/z: 425.2 [M+H]+

¹H-NMR (DMSO): δ [ppm] 14.1 (s, broad, 1H), 11.75 (s, broad, 1H), 8.6 (m, 2H), 7.2 (m, 2H), 5.0 (m, 1H), 4.7 (m, 1H), 4.3 (m, 2H), 4.2 (m, 1H), 4.0 (m, 1H), 3.8 (m, 1H), 3.75 (m, 2H); 3.25 (m, 2H), 3.15 (m, 2H), 2.6 (m, 1H), 2.3 (m, 4H), 2.0 (m, 1H), 1.85 (m, 1H), 1.4 (s, 9H), 1.2 (d, 3H).

Example 29

(S)-2-tert-Butyl-4-cyclobutyl-6-{4-[2-methyl-3-(pyrimidin-2-yloxy)-propyl]-piperazin-1-yl}-pyrimidine hydrochloride 0.755 g of (S)-3-[4-(2-tert-butyl-6-cyclobutyl-pyrimidin-4-yl)-piperazin-1-yl]-2-methyl-propan-1-ol (2.18 mmol) were stirred in 7.6 ml of dimethylformamide under argon. 0.105 g of 60% sodium hydride (2.6 mmol) were added and the reaction mixture was stirred for 10 min. A solution of 0.275 g of 2-chloro-pyrimidine (2.4 mmol) in 2.4 ml of dimethylformamide was added and the reaction mixture was stirred for 16 h. 30 ml of water and 40 ml of ethyl acetate were then added to the reaction mixture. The organic layer was separated and the aqueous phase extracted with a further portion of ethyl acetate. The combined organic extracts were concentrated to dryness to give a yellowish oil (0.9 g). The crude product was purified by flash column chromatography eluting with ethyl acetate. The fractions containing the product were combined and evaporated under reduced pressure to give an almost colourless oil. The oil was dissolved in tert-butyl methyl ether and 4 N hydrochloric acid in dioxan was added. A white solid precipitated. The precipitate was collected by filtration, washed with tert-butyl methyl ether and dried in a vacuum oven to yield 0.5 g of the title compound.

MS (ESI) m/z: 425.3 [M+H]+

¹H-NMR (DMSO): δ [ppm] 14.1 (s, broad, 1H), 11.7 (s, broad, 1H), 8.6 (m, 2H), 7.2 (m, 2H), 5.0 (m, 1H), 4.7 (m, 1H), 4.3 (m, 2H), 4.2 (m, 1H), 4.0 (m, 1H), 3.8 (m, 1H), 3.75 (m, 2H); 3.25 (m, 2H), 3.15 (m, 2H), 2.6 (m, 1H), 2.3 (m, 4H), 2.0 (m, 1H), 1.85 (m, 1H), 1.4 (s, 9H), 1.2 (d, 3H).

Example 30

(R)-2-tert-Butyl-4-cyclobutyl-6-{4-[2-methyl-3-(2-methylsulfanyl-pyrimidin-4-yloxy)-pronyl]-piperazin-1-yl}-pyrimidine 0.24 g of sodium hydride (6 mmol; 60% in mineral oil) was washed oil-free with pentane before 1 g of (R)-3-[4-(2-tert-butyl-6-cyclobutyl-pyrimidin-4-yl)-piperazin-1-yl]-2-methyl-propan-1-ol (2.89 mmol) dissolved in 30 ml of dioxane were added. The reaction mixture was heated to reflux for 1 h. After cooling, 0.5 g of 4-chloro-2-methylsulfanyl-pyrimidine (3.11 mmol) dissolved in 10 ml of dioxane were added. The reaction mixture was heated under reflux for 2 h. An additional 0.24 g of sodium hydride were added and the reaction mixture was heated under reflux for 2 h while stirring. The reaction mixture was partitioned between water and ethyl acetate. The organic layer was extracted with 5% aqueous citric acid, the aqueous phase was adjusted to basic pH with 2 N sodium hydroxide solution. The aqueous phase was re-extracted with ethyl acetate. The organic layer was dried over magnesium sulfate, filtered, and the solvent was evaporated to yield 1.34 g of the title compound as a yellowish oil.

MS (ESI) m/z: 471.3 [M+H]+

Example 31

(R)-4-{3-[4-(2-tert-Butyl-6-cyclobutyl-pyrimidin-4-yl)-piperazin-1-yl]-2-methyl-propoxy}-pyrimidin-2-ol 1.3 g of (R)-2-tert-butyl-4-cyclobutyl-6-{4-[2-methyl-3-(2-methylsulfanyl-pyrimidin-4-yloxy)-propyl]-piperazin-1-yl}-pyrimidine (2.76 mmol) were dissolved in 15 ml of acetic acid. 2.5 g of aqueous hydrogen peroxide (22.1 mmol, 30% in water) were added at 0° C. The reaction mixture was stirred for 15 h at room temperature, poured onto water and the aqueous phase was adjusted to alkaline pH with saturated sodium bicarbonate solution. After extraction with ethyl acetate, the organic phase was dried over magnesium sulfate, filtered, and the solvent evaporated. The crude product was purified by chromatography on silica gel using dichloromethane-methanol (2%), fractions containing the product were combined, the solvent was evaporated, and the residue treated with acetonitril, filtered and dried to yield 0.13 g of the title compound as a white solid.

MS (ESI) m/z: 441.2 [M+H]+

Example 32

(S)-2-tert-Butyl-4-cyclobutyl-6-{4-[2-methyl-3-(2-methylsulfanyl-pyrimidin-4-yloxy)-propyl]-piperazin-1-yl}-pyrimidine 0.48 g of sodium hydride (12 mmol; 60% in mineral oil) was washed oil-free with pentane before 1 g of (S)-3-[4-(2-tert-butyl-6-cyclobutyl-pyrimidin-4-yl)-piperazin-1-yl]-2-methyl-propan-1-ol (2.89 mmol) dissolved in 30 ml of dioxane were added. The reaction mixture was heated to reflux for 1 h. After cooling, 0.5 g of 4-chloro-2-methyl-sulfanyl-pyrimidine (3.11 mmol) dissolved in 10 ml of dioxane were added. Stirring under reflux conditions was continued for 2 h. The reaction mixture was partitioned between water and ethyl acetate. The organic layer was extracted with 5% aqueous citric acid, the aqueous phase was adjusted to basic pH with 2 N sodium hydroxide solution and re-extracted with ethyl acetate. The organic layer was dried over magnesium sulfate, filtered, and the solvent evaporated. The crude product was purified by chromatography on silica gel using ethyl acetate. Fractions containing the product were combined and the solvent was evaporated to yield 1 g of the title compound as a yellowish oil.

MS (ESI) m/z: 471.3 [M+H]+

Example 33

(S)-4-{3-[4-(2-tert-Butyl-6-cyclobutyl-pyrimidin-4-yl)-piperazin-1-yl]-2-methyl-propoxy}-pyrimidin-2-ol 1 g of (S)-2-tert-butyl-4-cyclobutyl-6-{4-[2-methyl-3-(2-methylsulfanyl-pyrimidin-4-yloxy)-propyl]-piperazin-1-yl}-pyrimidine (2.12 mmol) were dissolved in 10 ml of acetic acid. 2 g of aqueous hydrogen peroxide (17.6 mmol, 30% in water) were added at 0° C. The reaction mixture was stirred for 15 h at room temperature, poured onto water and the aqueous phase was adjusted to alkaline pH with saturated sodium bicarbonate solution. After extraction with ethyl acetate, the organic phase was dried over magnesium sulfate, filtered, and the solvent evaporated. The crude product was purified by chromatography on silica gel using dichloromethane-methanol (2%). Fractions containing the product were combined, the solvent was evaporated, and the residue treated with acetonitril, filtered and dried to yield 0.36 g of the title compound as a white solid.

MS (ESI) m/z: 441.2 [M+H]$^+$ $^1$H-NMR (DMSO): δ [ppm]11.3 (s, broad, 1H), 7.7 (d, 1H), 6.4 (s, 1H), 5.85 (d, 1H), 4.3 (m, 1H), 4.0 (m, 1H), 3.6 (m, 4H), 3.4 (m, 1H), 2.1-2.45 (several m, 10H), 1.95 (m, 1H), 1.85 (m, 1H), 1.25 (s, 9H), 0.95 (d, 3H).

Example 34

2-{4-[4-(2-tert-Butyl-6-cyclobutyl-pyrimidin-4-yl)-piperazin-1-yl]-butyl}-pyrimidin-4-ol 0.9 g of 5-[4-(2-tert-Butyl-6-cyclobutyl-pyrimidin-4-yl)-piperazin-1-yl]-pentamidine hydrochloride (2.42 mmol) and 0.65 g of 3-hydroxy-acrylic acid ethyl ester (4.71 mmol) were dissolved in 5 ml of tetrahydrofuran and 20 ml of water and stirred for 16 h at room temperature. The reaction mixture was partitioned between water and ethyl acetate, the organic layer dried over magnesium sulfate, filtered, and concentrated to dryness. The crude product was purified by chromatography on silica gel (eluent dichloromethane/methanol 95:5 to 9:1 v/v). Fractions containing the product were combined. The solvent was evaporated and the residue treated with acetonitrile. The precipitate was collected by filtration and dried to yield 0.35 g of the title compound as a white solid.

MS (ESI) m/z: 425.5 [M+H]$^+$ $^1$H-NMR (DMSO): δ [ppm] 12.4 (s, broad, 1H), 7.8 (d, 1H), 6.4 (s, 1H), 6.15 (d, 1H), 3.5-3.6 (m, 4H), 3.3-3.4 (m, 2H), 2.55 (m, 2H), 2.4 (m, 4H), 2.1-2.35 (m, 6H), 1.95 (m, 1H), 1.8 (m, 1H), 1.7 (m, 2H), 1.45 (m, 2H), 1.3 (s, 9H).

Example 35

2-tert-Butyl-4-cyclopropyl-6-{4-[3-(1-methyl-1H-tetrazol-5-ylsulfanyl)-propyl]-piperazin-1-yl}-pyrimidine hydrochloride 0.346 g of 1-Methyl-1H-tetrazole-5-thiol (2.98 mmol), 0.071 g of lithium hydroxide (2.98 mmol), and 0.223 g of sodium iodide (1.49 mmol) were stirred in 25 ml of dimethylformamide at 70° C. A solution of 1 g of 2-tert-butyl-4-[4-(3-chloro-propyl)-piperazin-1-yl]-6-cyclopropyl-pyrimidine (2.98 mmol) in 4 ml of dimethylformamide was added slowly within 2 h. After stirring for 2 h at 80° C., the dimethylformamide was evaporated under reduced pressure. The residue was partitioned between 15 ml of aqueous sodium chloride, 15 ml of water and 30 ml of ethyl acetate. The aqueous phase was re-extracted twice with ethyl acetate. The combined ethyl acetate phases were combined and dried over magnesium sulfate. The solvent was evaporated under reduced pressure. The crude product obtained was purified by column chromatography on silica gel using dichloromethane-ethyl acetate (7:3). Fractions containing the product were combined. The solvent was evaporated under reduced pressure. The residue was re-dissolved in 12 ml of ethyl acetate and treated with 2 equivalents of hydrochloric acid in dioxane. The supernatant was removed with a pipette, diisopropyl ether was added, the mixture was stirred, and the solvent was evaporated slowly under reduced pressure to yield 0.9 g of the title compound.

MS (ESI) m/z: 417.3 [M+H]$^+$ $^1$H-NMR (DMSO): S [ppm] 11.5 (s, broad, 1H), 6.55 (s, 1H), 3.95 (s, 3H), 3.5-3.7 (m, 6H), 3.4 (m, 2H), 3.25 (m, 2H), 3.15 (m, broad, 2H), 2.6 (m, 1H), 2.2 (m, 2H), 1.4 (s, 9H), 1.2 (m, 2H), 1.15 (m, 2H).

Example 36

4-{4-[3-(4-Benzyloxy-pyrimidin-2-yloxy)-propyl]-piperazin-1-yl}-2-tert-butyl-6-cyclopropyl-pyrimidine 0.5 g of 3-[4-(2-tert-Butyl-6-cyclopropyl-pyrimidin-4-yl)-piperazin-1-yl]-propan-1-ol (1.57 mmol) were dissolved in 5 ml of tetrahydrofuran. 1.5 ml of n-butyllithium (15% in hexane) were added to the mixture at 0° C. Stirring was continued for 30 min and then 0.45 g of 4-benzyloxy-2-methanesulfonyl-pyrimidine (1.7 mmol) dissolved in 5 ml of tetrahydrofuran were added. The reaction was stirred overnight at room temperature and for an additional 2 h at 40° C. The reaction mixture was partitioned between water and ethyl acetate. The organic layer was dried over magnesium sulfate, filtered, and the solvent was evaporated. The crude product was purified by chromatography on silica gel using dichloromethane-methanol (0-3%) as eluent to yield 0.6 g of the title compound.

Example 37

2-{3-[4-(2-tert-Butyl-6-cyclopropyl-pyrimidin-4-yl)-piperazin-1-yl]-propoxy}-pyrimidin-4-ol 0.5 g of 4-{4-[3-(4-Benzyloxy-pyrimidin-2-yloxy)-propyl]-piperazin-1-yl}-2-tery-butyl-6-cyclopropyl-pyrimidine (1.0 mmol) were dissolved in 20 ml of tetrahydrofuran and, after addition of 0.1 g of 10% Pd/C, the reaction mixture was hydrogenated for 1 h at 40° C. The catalyst was removed by filtration and the solvent was evaporated under reduced pressure. The remaining oil crystallized by addition of acetonitril to yield 0.2 g of the title compound.

MS (ESI) m/z: 413.3 [M+H]$^+$ $^1$H-NMR (CDCl$_3$): δ [ppm] 7.7 (d, 1H), 6.15 (s, 1H), 6.1 (d, 1H), 4.45 (m, 2H), 3.6 (m, 4H), 2.55 (m, 6H), 2.0 (m, 2H), 1.8 (m, 1H), 1.3 (s, 9H), 1.05 (m, 2H), 0.85 (m, 2H).

Example 38

2-tert-Butyl-4-cyclopropyl-6-{4-[3-([1,3,4]thiadiazol-2-ylsulfanyl)-propyl]-piperazin-1-yl}-pyrimidine 0.21 g of [1,3,4]thiadiazol-2-thiol (1.77 mmol) were dissolved in 20 ml of dimethylformamide. After addition of 0.04 g of lithium hydroxide (1.77 mmol) and 0.13 g of sodium iodide (0.88 mmol), the reaction mixture was stirred at 70° C. and 0.6 g of 2-tert-butyl-4-[4-(3-chloro-propyl)-piperazin-1-yl]-6-cyclopropyl-pyrimidine (1.77 mmol), dissolved in 5 ml of dimethylformamide, were added dropwise within 2 h. The mixture was stirred at 80° C. for 2 h, cooled to room temperature and the solvent was evaporated. The residue was partitioned between 40 ml of ethyl acetate and 15 ml of saturated aqueous sodium chloride solution. The aqueous phase was reextracted twice with ethyl acetate, the combined organic layers were dried over magnesium sulfate, filtered, and concentrated to dryness, to yield 0.69 g of the crude product, which was further purified by chromatography on silica gel using dichloromethane-methanol (1:1) and ethyl acetate. Fractions containing the product were combined and the solvents were evaporated. The oily residue crystallized upon standing to yield 0.39 g of the title compound.

MS (ESI) m/z: 419.2 [M+H]$^+$ $^1$H-NMR (DMSO): δ [ppm] 9.5 (s, 1H), 6.5 (S, 1H), 3.55 (m, 3H), 3.35 (m, 2H), 2.45 (m, 6H), 1.95 (m, 2H), 1.85 (m, 2H), 1.2 (s, 9H), 0.95 (m, 2H), 0.85 (m, 2H).

Example 39

2-tert-Butyl-4-cyclopropyl-6-{4-[3-(5-methyl-[1,3,4]
thiadiazol-2-ylsulfanyl)-propyl]-piperazin-1-yl}-
pyrimidine 0.23 g of 5-methyl-[1,3,4]thiadiazol-2-thiol (1.77 mmol) were dissolved in 20 ml of dimethylformamide. After addition of 0.04 g of lithium hydroxide (1.77 mmol) and 0.13 g of sodium iodide (0.88 mmol), the reaction mixture was stirred at 70° C. and 0.6 g of 2-tert-butyl-4-[4-(3-chloro-propyl)-piperazin-1-yl]-6-cyclopropyl-pyrimidine (1.77 mmol), dissolved in 5 ml of dimethylformamide, added dropwise over 2 h. The mixture was stirred at 80° C. for 2 h. The dimethylformamide was then evaporated. The residue was partitioned between 40 ml of ethyl acetate and 15 ml of saturated aqueous sodium chloride solution and 15 ml of water. The aqueous phase was re-extracted twice with ethyl acetate. The combined organic layers were dried over magnesium sulfate, filtered, and concentrated to dryness, to yield 0.69 g of the title compound as an oily residue. 0.8 g of the crude product were treated with 10 ml of n-hexane, the precipitate was collected by filtration and dried to yield 0.56 g of the title compound.

MS (ESI) m/z: 433.3 [M+H]$^+$ $^1$H-NMR (DMSO): δ [ppm] 6.5 (s, 1H), 3.55 (m, 4H), 3.3 (m, 2H), 2.7 (s, 3H), 2.4 (m, 5H), 1.8-1.95 (m, 3H), 1.2 (s, 9H), 0.9 (m, 2H), 0.85 (m, 2H).

Example 40

2-tert-Butyl-4-cyclopropyl-6-{4-[3-(pyrimidin-2-
ylsulfanyl)-propyl]-piperazin-1-yl}-pyrimidine 0.4 g of 2-mercapto-pyrimidine (3.57 mmol) were dissolved in 20 ml of dimethylformamide. After addition of 0.09 g of lithium hydroxide (3.57 mmol) and 0.27 g of sodium iodide (1.78 mmol), the reaction mixture was stirred at 60° C. and 1.2 g of 2-tert-butyl-4-[4-(3-chloro-propyl)-piperazin-1-yl]-6-cyclopropyl-pyrimidine (3.56 mmol) were added in portions. The reaction mixture was stirred at 60° C. for 1 h, and, after evaporation of dimethylformamide, the residue was partitioned between 30 ml of ethyl acetate and 15 ml of saturated aqueous sodium chloride solution and 15 ml of water. The aqueous phase was re-extracted twice with ethyl acetate. The combined organic layers were dried over magnesium sulfate, filtered, and concentrated to dryness. The crude product was re-dissolved in 30 ml of ethyl acetate and treated with 4 N hydrochloric acid in dioxane. The precipitated hydrochloride salt was collected by filtration and dried to yield 1.66 g of the title compound.

MS (ESI) m/z: 413.3 [M+H]$^+$ $^1$H-NMR (DMSO): δ [ppm] 14.45 (s, broad, 1H), 12.0 (s, broad, 1H), 8.7 (m, 2H), 7.25 (m, 1H), 6.5 (s, 1H), 5.0 (m, broad, 1H), 4.55 (m, broad, 1H), 3.5-3.8 (m, broad, 6H), 3.2 (m, 4H), 3.15 (m, 2H), 2.9 (m, 1H), 2.2 (m, 2H), 1.4 (s, 9H), 1.15-1.3 (m, 4H).

Example 41

2-tert-Butyl-4-{4-[3-(4-methyl-4H-[1,2,4]triazol-3-
ylsulfanyl)-propyl]-piperazin-1-yl}-6-cyclobutylpyri-
midine 0.8 g of 2-tert-Butyl-4-[4-(3-chloro-propyl)-piperazin-1-yl]-6-cyclobutyl-pyrimidine (2.28 mmol), 0.29 g of 4-methyl-3-mercapto-1,2,4-triazole (2.52 mmol), 0.15 g of lithium hydroxide and a tip of a spatula of potassium iodide were dissolved in 20 ml of dimethylformamide. The mixture was stirred for 14 h at room temperature and then extracted with water and ethyl acetate. The organic layer was dried over magnesium sulfate, filtered, and evaporated to dryness. The residue was then purified by column chromatography on silica gel (dichloromethane-methanol (2-10%)) to yield an oily residue that was precipitated with acetonitrile thereby yielding 0.46 g of the title compound (47%).

A larger batch was run using the following modification of the above procedure: Before extraction, dimethylformamide was evaporated. The silica gel chromatography was performed with ethyl acetate-methanol (0-20%). For final crystallization, the product was dissolved in 100 ml dichloromethane, 500 ml diisopropyl ethyl ether added. The first crop consisted of 65 g of the title compound, a second crop yielded another 7 g of the title compound (overall yield 73%)

MS (ESI) m/z: 430.5 [M+H]$^+$ $^1$H-NMR (DMSO): δ [ppm] 8.1 (s, 1H), 6.1 (s, 1H), 3.15 (m, 4H), 3.1 (s, 3H), 3.4 (m, 1H), 3.3 (m, 2H), 2.45 (m, 6H), 2.25 (m, 4H), 2.0 (m, 3H), 1.9 (m, 1H), 1.3 (s, 9H).

Example 42

2-tert-Butyl-4-{4-[3-(4-methyl-5-trifluoromethyl-
4H-[1,2,4]triazol-3-ylsulfanyl)-propyl]-piperazin-1-
yl}-6-cyclobutyl-pyrimidine 0.4 g of 2-tert-Butyl-4-[4-(3-chloro-propyl)-piperazin-1-yl]-6-cyclobutyl-pyrimidine (1.14 mmol), 0.22 g of 4-methyl-5-trifluoromethyl-4H-[1,2,4]triazole-3-thiol (1.2 mmol), 0.07 g of lithium-hydroxide (2.92 mmol) and a spatula tip of potassium iodide were stirred in 10 ml of dimethylformamide for 14 h at room temperature and for an additional 2 h at 80° C. After addition of water and ethyl acetate, the organic layer was separated, dried over magnesium sulfate, filtered and the solvent was evaporated. The residue was purified twice by column chromatography on silica gel using dichloromethane-methanol (1-5%). Fractions containing the product were combined, the solvents evaporated, the residue stirred with acetonitrile yielding 0.03 g (5.3%) of the product as a solid.

MS (ESI) m/z: 498.4 [M+H]$^+$ $^1$H-NMR (DMSO): δ [ppm] 12.0 (s, broad, 1H), 7.2 (s, 1H), 4.7 (m, 1H), 4.15 (m, 1H), 3.75 (m, 1H), 3.65 (m, broad, 4H), 3.45 (s, 3H), 3.4 (m, 2H), 3.1-3.3 (m, broad, 4H), 2.3 (m, broad, 4H), 2.2 (m, 2H), 2.0 (m, 1H), 1.85 (m, 1H), 1.4 (s, 9H),

Example 43

2-tert-Butyl-4-{4-[3-(4-methyl-5-methyl-4H-[1,2,4]
triazol-3-ylsulfanyl)-propyl]-piperazin-1-yl}-6-cy-
clobutyl-pyrimidine fumarate 0.4 g of 2-tert-Butyl-4-[4-(3-chloro-propyl)-piperazin-1-yl]-6-cyclobutyl-pyrimidine (1.14 mmol), 0.16 g of 4-methyl-5-methyl-4H-[1,2,4]triazole-3-thiol (1.24 mmol), 0.07 g of lithium-hydroxide (2.92 mmol) and a spatula tip of potassium iodide were stirred in 20 ml of dimethylformamide for 14 h at room temperature. After addition of water and ethyl acetate, the organic layer was separated, dried over magnesium sulfate, filtered and the solvent was evaporated. The residue was purified by silica gel column chromatography using dichloromethane-methanol (2-20%). Fractions containing the product were combined, the solvents evaporated. The residue was dissolved in isopropanol and 50 mg of fumaric acid were added. The solution was concentrated in vacuo to dryness to yield 0.15 g (23.5%) of a white solid.

MS (ESI) m/z: 444.2 [M+H]$^+$ $^1$H-NMR (DMSO): δ [ppm] 6.65 (s, 2H, fumarate), 6.4 (s, 1H), 3.65 (m, 4H), 3.5 (s, 3H), 3.4 (m, 1H), 3.1 (m, 2H), 2.6 (m, 6H), 2.35 (s, 3H), 2.25 (m, 2H), 2.15 (m, 2H), 1.95 (m, 1H), 1.85 (m, 3H), 1.3 (s, 9H)

Example 44

2-tert-Butyl-4-{4-[3-(4-methyl-5-cyclopropyl-4H-[1,2,4]triazol-3-ylsulfanyl)-propyl]-piperazin-1-yl}-6-cyclobutyl-pyrimidine fumarate 0.4 g of 2-tert-Butyl-4-[4-(3-chloro-propyl)-piperazin-1-yl]-6-cyclobutyl-pyrimidine (1.14 mmol), 0.2 g of 4-methyl-5-cyclopropyl-4H-[1,2,4]triazole-3-thiol (1.29 mmol), 0.07 g lithium-hydroxide (2.92 mmol) and a spatula tip of potassium iodide were stirred in 20 ml of dimethylformamide overnight at room temperature and for an additional 3 h at 40° C. After addition of water and ethyl acetate, the organic layer was separated, dried over magnesium sulfate, filtered and the solvent was evaporated. The residue was purified by column chromatography on silica gel using dichloromethane-methanol (0-2%). Fractions containing the product were combined and the solvents were evaporated. The residue was dissolved in isopropanol and 1 equivalent of fumaric acid was added. The solvent was evaporated and the residue was dissolved in diisopropylether to which some drops of isopropanol were added upon warming, thereby forming a precipitate. After cooling the precipitate was collected by filtration and dried. Yield: 0.04 g (6%)

MS (ESI) m/z: 470.5 [M+H]$^+$ $^1$H-NMR (DMSO): δ [ppm] 6.6 (s, 1H), 3.75 (m, 1H), 3.65 (m, 4H), 3.6 (m, 3H), 3.4 (m, 1H), 3.1 (m, 2H), 2.5 (m, 5H), 2.25 (m, 2H), 2.15 (m, 2H), 1.9 (m, 2H), 1.8 (m, 3H), 1.3 (s, 9H), 1.0 (m, 2H), 0.9 (m, 2H).

Example 45

2-tert-Butyl-4-{4-[3-(4-methyl-5-methyl-4H-[1,2,4]triazol-3-ylsulfanyl)-propyl]-piperazin-1-yl}-6-cyclopropyl-pyrimidine hydrochloride 0.23 g of 4-Methyl-5-methyl-4H-[1,2,4]triazole-3-thiol (1.78 mmol), 0.04 g lithium hydroxide (1.78 mmol) and 0.13 g sodium iodide (0.89 mmol) were dissolved in 20 ml of dimethylformamide. Within 2 h, 0.6 g of 2-tert-butyl-4-[4-(3-chloro-propyl)-piperazin-1-yl]-6-cyclopropyl-pyrimidine (1.78 mmol), dissolved in 5 ml dimethylformamide, were added at 70° C. The mixture was stirred for 1 h at 80° C. After cooling to room temperature, the solvent was evaporated and the oily residue partitioned between 30 ml of ethyl acetate and 15 ml of water plus 15 ml of a saturated solution of sodium chloride in water. The aqueous layer was reextracted twice with 20 ml of ethyl acetate each, the organic phases combined, dried over magnesium sulfate, filtered, and the solvent was evaporated. The residue was purified by column chromatography on silica gel using ethyl acetate, ethyl acetate-methanol 9:1, and ethyl acetate-methanol 1:1. Fractions containing the product were combined. After evaporation of the solvent, the residue was re-dissolved in diisopropylethyl ether and a 1 N solution of HCl in diethylether was added. The precipitated hydrochloride salt was collected by filtration. Yield: 343 mg.

MS (ESI) m/z: 430.5 [M+H]$^+$ $^1$H-NMR (DMSO): δ [ppm] 14.3 (s, 1H, broad), 12.0 (s, 1H, broad), 6.55 (s, 1H), 4.7-5.1 (m, 2H, very broad), 3.45-3.8 (m, 3H, very broad), 3.6 (s, 3H), 3.4 (m, 2H), 3.0-3.3 (m, 2H, very broad), 3.25 (m, 2H), 2.9 (m, 1H), 2.6 (s, 3H), 2.2 (m, 2H), 1.45 (s, 9H), 1.2-1.3 (m, 4H)

Example 46

2-tert-Butyl-4-{4-[3-(4-methyl-4H-[1,2,4]triazol-3-ylsulfanyl)-propyl]-piperazin-1-yl}-6-cyclopropyl-pyrimidine acetate 0.7 g of 2-tert-Butyl-4-[4-(3-chloro-propyl)-piperazin-1-yl]-6-cyclopropyl-pyrimidine (1.45 mmol) and 0.55 g of 4-methyl-4H-[1,2,4]triazole-3-thiol (2.08 mmol) were dissolved in 10 ml of dimethylformamide. After addition of 0.104 g of lithium hydroxide (4.36 mmol) and 0.109 g of sodium iodide (0.73 mmol), the reaction mixture was stirred at 70° C. for 3 h. After cooling, the solvent was evaporated and the residue partitioned between dichloromethane and half-saturated sodium chloride solution. The organic layer was dried over magnesium sulfate, filtered, and the solvent was evaporated. The residue was purified via preparative HPLC on a C18-Symmetry column (Waters) with water/methanol (0.1% acetic acid). Fractions containing the product were combined and lyophilised to yield 0.075 g of the product.

MS (ESI) m/z: 416.2 [M+H]$^+$

Example 47

2-tert-Butyl-4-{4-[3-(4-methyl-5-trifluoromethyl-4H-[1,2,4]triazol-3-ylsulfanyl)-propyl]-piperazin-1-yl}-6-cyclopropyl-pyrimidine hydrochloride 0.3 g of 2-tert-Butyl-4-[4-(3-chloro-propyl)-piperazin-1-yl]-6-cyclopropyl-pyrimidine (0.89 mmol) were dissolved in 10 ml dimethylformamide. After the addition of 0.163 g 4-Methyl-5-trifluoromethyl-4H-[1,2,4]triazole-3-thiol (0.89 mmol), 0.064 g lithium hydroxide (2.76 mmol) and 0.067 g sodium iodide (0.45 mmol), the reaction mixture was stirred at 78° C. for 3 h. After cooling, the solvent was evaporated and the residue was dissolved in 30 ml of ethyl acetate. After washing twice with water, the organic phase was dried over magnesium sulfate, filtered, and the solvent was evaporated. The residue was purified chromatography on silica gel with ethyl acetate. Fractions containing the product were combined and the solvent was evaporated. The hydrochloride was formed by addition of 4 N HCl in dioxan to yield 0.14 g of the title compound.

MS (ESI) m/z: 484.2 [M+H]$^+$ $^1$H-NMR (DMSO): δ [ppm] 14.3 (s, broad, 1H), 11.95 (s, broad, 1H), 6.55 (s, 1H), 5.0 (m, broad, 1H), 4.55 (m, broad, 1H), 3.7-3.9 (m, very broad, 2H), 3.7 (s, 3H), 3.6 (m, 2H), 3.35 (m, 2H), 3.2 (m, 2H), 3.1 (m, 2H), 2.8 (m, 1H), 2.2 (m, 2H), 1.45 (s, 9H), 1.3 (m, 2H).

The compounds of the examples 48 to 50 and 55 to 63 were prepared in a similar manner as described in the examples 1 to 47.

Example 48

2-tert-Butyl-4-{4-[3-(1,3-dimethyl-1H-pyrazol-5-ylsulfanyl)-propyl]-piperazin-1-yl}-6-cyclobutylpyrimidine MS (ESI) m/z: 443 [M+H]$^+$

Example 49

2-tert-Butyl-4-{4-[3-(1,3-dimethyl-1H-pyrazol-5-yloxy)-propyl]-piperazin-1-yl}-6-cyclobutylpyrimidine MS (ESI) m/z: 427 [M+H]+

Example 50

2-tert-Butyl-4-cyclobutyl-6-{4-[3-(1-cyclopropyl-1H-pyrazol-3-yloxy)-pronyl]-piperazin-1-yl}-pyrimidine MS (ESI) m/z: 439 [M+H]+

Example 51

2-{(R)-3-[4-(2-tert-Butyl-6-cyclobutylpyrimidin-4-yl)-piperazin-1-yl]-2-methylpropoxy}-4-benzoyloxypyrimidin 1.05 g of (R)-3-[4-(2-tert-Butyl-6-cyclobutyl-pyrimidin-4-yl)-piperazin-1-yl]-2-methyl-propan-1-ol (3.02 mmol) were dissolved in 8 ml of tetrahydrofuran. At 0° C., 1.71 ml (3.37 mmol) of n-butyllithium (2 M in pentane) were added within 15 minutes. 0.85 g of 2-methylsulfonyl-4-benzyloxy-pyrimidine (3.21 mmol), dissolved in 5 ml of tetrahydrofurane, were added. Stirring continued for 16 h at room temperature. By cooling with, 2 ml of water were added. The obtained mixture was poured into 15 ml of water and extracted three times with 15 ml of diethyl ether each. The organic layers were combined, dried over magnesium sulfate, filtered and evaporated to dryness. The residue was purified via silica gel chromatography with dichloromethane, dichloromethane/ethyl acetate 9:1, and dichlormethane/ethyl acetate 3:2 to yield 0.83 g of the product.

MS (ESI) m/z: 531.3 [M+H]+

Example 52

(R)-2-{4-(2-tert-Butyl-6-cyclobutyl-pyrimidin-4-yl)-piperazin-1-yl]-2-methyl-propoxy}-pyrimidine-4-ol 0.82 g of (R)-2-{3-[4-(2-tert-Butyl-6-cyclobutyl-pyrimidin-4-yl)-piperazin-1-yl]-2-methyl-propoxy}-4-benzyloxy-pyrimidine (1.545 mmol) were dissolved in 15 ml of tetrahydrofurane under nitrogen atmosphere. 0.2 g of Pd/C (10%) were added, and the mixture hydrogenated at 50° C. The catalyst was removed by filtration and the filtrate was evaporated to dryness to yield 0.62 g of the title compound product in 87% purity. $^1$H-NMR (CDCl$_3$): δ [ppm] 7.75 (d, 1H), 6.1 (m, 2H), 4.45 (m, 1H), 4.25 (m, 1H), 3.55-3.65 (m, broad, 4H), 3.4-3.5 (m, broad, 1H), 2.5 (m, 2H), 2.4 (m, 3H), 2.2-2.3 (m, broad, 6H), 2.0 (m, 1H), 1.9 (m, 1H), 1.3 (s, 9H), 1.0 (d, 3H).

Example 53

2-tert-butyl-4-{4-[3-(4-methyl-4H-[1,2,4]triazol-3-ylsulfanyl)-propyl]-piperazin-1-yl}-6-(1-methyl)cyclopropyl-pyrimidine 0.3 g of 4-methyl-3-mercapto-1,2,4-triazole-triazole (2.6 mmol) and 0.91 g of 2-tert-Butyl-4-[4-(3-chloro-propyl)-piperazin-1-yl]-6-(1-methyl)cyclopropyl-pyrimidine (2.6 mmol) were reacted as described for EXAMPLE 41 to yield, after silicia gel chromatography (ethyl acetate and ethyl acetate-methanol 4:1 as eluents), 0.77 g of the title compound MS (ESI) m/z: 430.2 [M+H]+

$^1$H-NMR (CDCl$_3$): δ [ppm] 8.1 (s, 1H), 6.3 (s, 1H), 3.65 (m, 4H), 3.6 (s, 3H), 3.3 (m, 2H), 2.45-2.55 (m, 6H), 2.0 (m, 2H), 1.4 (s, 3H), 1.345 (M, 2H), 1.25 (s, 9H), 0.7 (m, 2H).

Example 54

2-tert-butyl-4-{4-[3-(4-methyl-5-methyl-4H-[1,2,4]triazol-3-ylsulfanyl)-propyl]piperazin-1-yl}-6-(1-methyl)cyclopropyl-pyrimidine 0.3 g of 4-methyl-5-methyl-3-mercapto-1,2,4-triazole (2.32 mmol) and 0.81 g of 2-tert-Butyl-4-[4-(3-chloro-propyl)-piperazine-1-yl]-6-(1-methyl)cyclopropyl-pyrimidine (2.32 mmol) were reacted as described for EXAMPLE 41 to yield, after silica gel chromatography (ethyl acetate and ethyl acetate-methanol 4:1 as eluents), 0.56 g of the desired product.

MS (ESI) m/z: 444.2 [M+H]+

$^1$H-NMR (DMSO): δ [ppm] 6.45 (s, 1H), 3.6 (m, 4H), 3.45 (s, 3H), 3.2 (s, 3H), 3.1 (t, 2H), 2.3-2.45 (m, broad, 8H), 1.8 (m, 2H), 1.4 (s, 3H), 1.15-1.25 (m, broad, 9H), 0.7 (m, 2H).

The compounds of examples 55 to 66 were prepared according to the methods outlined in examples 1 to 54.

Example 55

2-tert-butyl-4-{4-[3-(5-fluoro-pyrimidin-2-yloxy)-propyl]-piperazin-1-yl}-6-cyclobutylpyrimidine MS (ESI) m/z: 429.3 [M+H]+

$^1$H-NMR (CDCl$_3$): δ [ppm] 8.35 (s, 2H), 6.1 (s, 1H), 4.4 (t, 2H), 3.6 (m, broad, 4H), 3.4 (m, 1H), 2.45-2.6 (m, broad, 6H), 2.2-2.35 (m, 4H), 1.95-2.1 (m, 3H), 1.8-1.9 (m, 1H), 1.35 (s, 9H).

Example 56

2-tert-butyl-4-{4-[3-(5-pyrazin-4-methyl-4H-[1,2,4]triazol-3-ylsulfanyl)-propyl]-piperazin-1-yl}6-cyclopropyl-pyrimidine hydrochloride MS (ESI) m/z: 494.25 [M+H]+

$^1$H-NMR (DMSO): δ [ppm] 14.4 (s, broad, 1H), 12.0 (s, broad, 1H), 9.3 (s, 1H), 8.8 (m, 2H), 6.5 (s, 1H), 5.0 (s, br, 1H), 4.5 (s, br, 1H), 4.0-4.2 (m, br, 3H), 3.9 (s, 3H), 3.5-3.8 (m, br, 3H), 3.4 (m, 2H), 3.25 (m, br, 2H), 2.85 (m, br, 1H), 2.2-2.3 (m, br, 2H), 1.4-1.5 (s, br, 9H), 1.1-1.3 (m, br, 4H).

Example 57

2-cyclopropyl-4-{4-[3-(5-pyrazin-4-methyl-4H-[1,2,4]triazol-3-ylsulfanyl)-propyl]-piperazin-1-yl}6-tert-butyl-pyrimidine hydrochloride MS (ESI) m/z: 494.25 [M+H]+

$^1$H-NMR (DMSO): δ [ppm] 14.4 (s, broad, 1H), 11.95 (s, broad, 1H), 9.3 (s, 1H), 8.8 (m, 2H), 6.8 (s, 1H), 4.9 (s, br, 1H), 4.6 (s, br, 1H), 4.1-4.4 (m, br, 4H), 3.9 (s, 3H), 3.8 (m, br, 1H), 3.4 (m, 2H), 3.25 (m, br, 2H), 3.05-3.2 (m, br, 2H), 2.2-2.3 (m, br, 2H), 1.4-1.5 (s, br, 9H), 1.1-1.3 (m, br, 4H).

Example 58

2-cyclobutyl-4-{4-[3-(4-methyl-4H-[1,2,4]triazol-3-ylsulfanyl)-propyl]-piperazin-1-yl}-6-tert-butyl-pyrimidine hydrochloride MS (ESI) m/z: 430.25 [M+H]$^+$

Example 59

2-tert-butyl-4-{4-[3-(5-(pyrid-3-yl)-4-methyl-4H-[1,2,4]triazol-3-ylsulfanyl)-propyl]-piperazin-1-yl}-6-cyclopropyl-pyrimidine hydrochloride MS (ESI) m/z: 493.25 [M+H]$^+$

Example 60

2-tert-butyl-4-{4-[3-(1-methyl-1H-[1,2,4]triazol-3-ylsulfanyl)-propyl]-piperazin-1-yl}-6-cyclobutyl-pyrimidine hydrochloride MS (ESI) m/z: 430.2 [M+H]$^+$

Example 61

2-tert-butyl-4-{4-[3-(4-methyl-4H-[1,2,4]triazol-3-yloxy)-propyl]-piperazin-1-yl}-6-cyclobutyl-pyrimidine MS (ESI) m/z: 414 [M+H]$^+$

Example 62

2-tert-Butyl-4-cyclobutyl-6-{4-[3-(1H-[1,2,4]triazol-3-ylsulfanyl)-pronyl]-piperazin-1-yl}-pyrimidine MS (ESI) m/z: 416.2 [M+H]$^+$
$^1$H-NMR (CDCl$_3$): δ [ppm] 8.0 (s, 1H), 6.15 (s, 1H), 3.75 (m, 4H), 3.45 (m, 1H), 3.2 (m, 2H), 2.55-2.7 (2m, 6H), 2.2-2.35 (m, 4H), 1.95-2.1 (m, 3H), 1.9 (m, 1H), 1.35 (s, 9H).

Example 63

2-tert-Butyl-4-(1-methyl-cyclopropyl)-6-{4-[3-(4-methyl-5-phenyl-4H-[1,2,4]triazol-3-yloxy)-propyl]-piperazin-1-yl}-pyrimidine MS (ESI) m/z: 490.4 [M+H]$^+$
$^1$H-NMR (CDCl$_3$): δ [ppm] 7.65 (m, 2H), 7.45 (m, 3H), 6.3 (s, 1H), 4.6 (m, 2H), 3.65 (m, broad, 4H), 3.45 (s, 3H), 2.5-2.6 (m, broad, 6H), 2.1 (m, 2H), 1.4 (s, 3H), 1.35 (m, 2H), 1.3 (s, 9H), 0.7 (m, 2H).

Example 64

2-tert-Butyl-4-cyclobutyl-6-{4-[3-(4-methyl-5-phenyl-4H-[1,2,4]triazol-3-yloxy)-propyl]-piperazin-1-yl}-pyrimidine MS (ESI) m/z: 490.2 [M+H]$^+$
$^1$H-NMR (CDCl$_3$): δ [ppm] 7.65 (m, 2H), 7.45 (m, 3H), 6.1 (s, 1H), 4.6 (m, 2H), 3.65 (m, broad, 4H), 3.45 (s, 3H), 3.4 (m, 1H), 2.5-2.6 (m, broad, 6H), 2.2-2.35 (m, broad, 4H), 2.1 (m, 2H), 2.0 (m, 1H), 1.85 (m, 1H), 1.3 (s, 9H).

Example 65

2-(1-Methyl-cyclopropyl)-4-{4-[3-(4-methyl-4H-[1,2,4]triazol-3-ylsulfanyl)-propyl]-piperazin-1-yl}-6-trifluoromethyl-pyrimidine MS (ESI) m/z: 442.1 [M+H]$^+$
$^1$H-NMR (CDCl$_3$): δ [ppm] 8.1 (s, 1H), 6.5 (s, 1H), 3.65 (m, broad, 4H), 3.6 (s, 3H), 3.3 (m, 2H), 2.5 (m, broad, 6H), 2.1 (m, broad, 1H), 2.0 (m, 2H), 1.5 (s, 3H), 1.3 (m, 2H), 0.8 (m, 2H).

Example 66

2-tert-Butyl-4-cyclobutyl-6-(4-{3-[4-methyl-5-(1-methyl-1H-pyrrol-2-yl)-4H-[1,2,4]triazol-3-ylsulfanyl]-propyl}-piperazin-1-yl)-pyrimidine hydrochloride MS (ESI) m/z: 509.2 [M+H]$^+$
$^1$H-NMR (DMSO): δ [ppm] 14.0 (s, broad, 1H), 12.05 (s, broad, 1H), 7.15 (s, 1H), 7.1 (s, 1H), 6.6 (m, 1H), 6.2 (m, 1H), 5.0 (m, very broad, 1H), 4.4 (m, very broad, 5H), 4.1 (m, 1H), 3.75 (s, 3H), 3.7 (m, very broad, 1H), 3.6 (s, 3H), 3.4 (m, 2H), 3.25 (m, 2H), 3.2 (m, very broad, 1H), 2.15-2.4 (several m, 6H), 2.0 (m, 1H), 1.85 (m, 1H), 1.4 (s, 9H).

The compounds of the general formula I as shown in table 1 can be prepared according to the methods outlined in examples 1 to 54.

TABLE 1

| Exp. # | Ar | -X-A- | R$^1$ | R$^{1a}$ |
|---|---|---|---|---|
| 67 | [1,3,4]thiadiazol-2-yl | —O—(CH$_2$)$_3$— | tert.-butyl | cyclobutyl |
| 68 | 5-methyl-[1,3,4]thiadiazol-2-yl | —O—(CH$_2$)$_3$— | tert.-butyl | cyclobutyl |
| 69 | 2,4-difluoro-benzoyl- | —NH(CH$_2$)$_4$— | tert.-butyl | cyclobutyl |
| 70 | 4-methyl-4H[1,2,4]triazol-3-yl | —S—(CH$_2$)$_3$— | cyclopropyl | tert.-butyl |
| 71 | 4-methyl-4H[1,2,4]triazol-3-yl | —S—(CH$_2$)$_3$— | 1-methyl-cyclopropyl | tert.-butyl |
| 72 | 5-phenyl-4-methyl-4H[1,2,4]triazol-3-yl | —O—(CH$_2$)$_3$— | cyclopropyl | tert.-butyl |
| 73 | 5-phenyl-4-methyl-4H[1,2,4]triazol-3-yl | —O—(CH$_2$)$_3$— | tert.-butyl | cyclopropyl |
| 74 | 5-(4-fluorophenyl)-4-methyl-4H[1,2,4]triazol-3-yl | —O—(CH$_2$)$_3$— | cyclopropyl | tert.-butyl |
| 75 | 5-(4-fluorophenyl)-4-methyl-4H[1,2,4]triazol-3-yl | —O—(CH$_2$)$_3$— | tert.-butyl | cyclopropyl |
| 76 | 5-phenyl-4-methyl-4H[1,2,4]triazol-3-yl | —O—(CH$_2$)$_3$— | 1-methyl-cyclopropyl | tert.-butyl |

TABLE 1-continued

| Exp. # | Ar | -X-A- | R¹ | R¹ᵃ |
|---|---|---|---|---|
| 77 | 5-pyrazinyl-4-methyl-4H[1,2,4]triazol-3-yl | —O—(CH₂)₃— | tert.-butyl | cyclopropyl |
| 78 | 1-methyl-1H-tetrazol-5-yl | —O—(CH₂)₃— | tert.-butyl | cyclobutyl |
| 79 | 2-methyl-1H-tetrazol-5-yl | —O—(CH₂)₃— | tert.-butyl | cyclobutyl |
| 80 | 2-methyl-1H-tetrazol-5-yl | —S—(CH₂)₃— | tert.-butyl | cyclobutyl |
| 81 | 2-hydroxy-pyrimidyl-4-yl | —(CH₂)₄— | tert.-butyl | cyclobutyl |
| 82 | 4-methyl-5-ethyl-4H-1,2,4-triazol-3-yl | —S—(CH₂)₃ | tert.-butyl | 1-methyl-cyclopropyl |
| 83 | 4-methyl-5-methoxymethyl-4H-1,2,4-triazol-3-yl | —S—(CH₂)₃ | tert.-butyl | 1-methyl-cyclopropyl |
| 84 | 5-pyrazinyl-4-methyl-4H[1,2,4]triazol-3-yl | —O—(CH₂)₃— | cyclopropyl | tert.-butyl |

III. Examples of Galenic Administration Forms

A) Tablets

Tablets of the following composition are pressed on a tablet press in the customary manner:

40 mg of substance from Example 8
120 mg of corn starch
13.5 mg of gelatin
45 mg of lactose
2.25 mg of Aerosil® (chemically pure silicic acid in sub-microscopically fine dispersion)
6.75 mg of potato starch (as a 6% paste)

B) Sugar-Coated Tablets 20 mg of substance from Example 8
60 mg of core composition
70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

IV. Biological Investigations

Receptor Binding Studies:

The substance to be tested was either dissolved in methanol/Chremophor® (BASF-AG) or in dimethyl sulfoxide and then diluted with water to the desired concentration.

Dopamine $D_3$ receptor:

The assay mixture (0.250 ml) was composed of membranes derived from ~$10^6$ HEK-293 cells possessing stably expressed human dopamine $D_3$ receptors, 0.1 nM [$^{125}$I]-iodosulpride and incubation buffer (total binding) or, in addition, test substance (inhibition curve) or 1 µM spiperone (nonspecific binding). Each assay mixture was run in triplicate.

The incubation buffer contained 50 mM tris, 120 mM NaCl, 5 mM KCl, 2 mM CaCl₂, 2 mM MgCl₂ and 0.1% bovine serum albumin, 10 µM quinolone and 0.1% ascorbic acid (prepared fresh daily). The buffer was adjusted to pH 7.4 with HCl.

Dopamine $D_{2L}$ Receptor:

The assay mixture (1 ml) was composed of membranes from ~$10^6$ HEK-293 cells possessing stably expressed human dopamine $D_{2L}$ receptors (long isoform) and 0.01 nM [$^{125}$I] iodospiperone and incubation buffer (total binding) or, in addition, test substance (inhibition curve) or 1 µM haloperidol (nonspecific binding). Each assay mixture was run in triplicate.

The incubation buffer contained 50 mM tris, 120 mM NaCl, 5 mM KCl, 2 mM CaCl₂, 2 mM MgCl₂ and 0.1% bovine serum albumin. The buffer was adjusted to pH 7.4 with HCl.

Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptro binding studies are expressed as receptor binding constants $K_i(D_2)$ and $K_i(D_3)$, respectively, as herein before described, and given in table 2.

In these tests, the compounds according to the invention exhibit very good affinities for the $D_3$ receptor (<10 nM, frequently <5 nM) and bind selectively to the $D_3$ receptor.

The results of the binding tests are given in table 2.

TABLE 2

| Exp. # | Ar | —X—A— | R¹ | R¹ᵃ | $K_i(D_3)$* [nm] | $K_i(D_2)$* [nm] | $K_i(D_2)/K_i(D_3)$ |
|---|---|---|---|---|---|---|---|
| 1 | [1,3,4]thiadiazol-2-yl | —S—(CH₂)₃— | tert.-butyl | cyclobutyl | 0.9 | 49 | 54 |
| 2 | 5-methyl-[1,3,4]thiadiazol-2-yl | —S—(CH₂)₃— | tert.-butyl | cyclobutyl | 1.4 | 135 | 96 |
| 4 | pyrimidyl-2-yl | —S—(CH₂)₃— | tert.-butyl | cyclobutyl | 0.9 | 113 | 127 |
| 9 | 1-methyl-1H-tetrazol-5-yl | —S—(CH₂)₃— | tert.-butyl | Cyclobutyl | 4.1 | 432 | 106 |
| 10 | 4-fluoro-benzoyl- | —NH(CH₂)₄— | tert.-butyl | cyclobutyl | 0.5 | 87 | 163 |
| 11 | pyridyl-4-carbonyl- | —NH(CH₂)₄— | tert.-butyl | cyclobutyl | 0.9 | 137 | 150 |
| 12 | pyridyl-3-carbonyl- | —NH(CH₂)₄— | tert.-butyl | cyclobutyl | 1.0 | 115 | 121 |

TABLE 2-continued

| Exp. # | Ar | —X—A— | $R^1$ | $R^{1a}$ | $K_i(D_3)$* [nm] | $K_i(D_2)$* [nm] | $K_i(D_2)/K_i(D_3)$ |
|---|---|---|---|---|---|---|---|
| 24 | 2-hydroxy-pyrimidyl-4-yl | —O—(CH$_2$)$_3$— | tert.-butyl | cyclobutyl | 1.2 | 112 | 93 |
| 26 | 4-hydroxy-pyrimidyl-2-yl | —O—(CH$_2$)$_3$— | tert.-butyl | cyclobutyl | 4.8 | 337 | 70 |
| 27 | pyrimidyl-2-yl | —O—(CH$_2$)$_3$— | tert.-butyl | cyclobutyl | 2.1 | 222 | 107 |
| 28 | pyrimidyl-2-yl | -(R)-O—CH$_2$CH(CH$_3$)CH$_2$— | tert.-butyl | cyclobutyl | 3.8 | 296 | 78 |
| 31 | 2-hydroxy-pyrimidyl-4-yl | -(R)-O—CH$_2$CH(CH$_3$)CH$_2$— | tert.-butyl | cyclobutyl | 2.0 | 143 | 72 |
| 34 | 4-hydroxy-pyrimidyl-2-yl | —(CH$_2$)$_4$— | tert.-butyl | cyclobutyl | 1.1 | 77 | 71 |
| 35 | 1-methyl-1H-tetrazol-5-yl | —S—(CH$_2$)$_3$— | tert.-butyl | cyclopropyl | 3.8 | 587 | 154 |
| 37 | 4-hydroxy-pyrimidyl-2-yl | —O—(CH$_2$)$_3$— | tert.-butyl | cyclopropyl | 7.1 | 359 | 51 |
| 41 | 4-methyl-4H-1,2,4-triazol-3-yl | —S—(CH$_2$)$_3$— | tert.-butyl | cyclobutyl | 1.3 | 405 | 314 |
| 42 | 4-methyl-5-trifluoromethyl-4H-1,2,4-triazol-3-yl | —S—(CH$_2$)$_3$— | tert.-butyl | cyclobutyl | 2 | 405 | 203 |
| 43 | 4,5-dimethyl-4H-1,2,4-triazol-3-yl | —S—(CH$_2$)$_3$— | tert.-butyl | cyclobutyl | 1.5 | 305 | 210 |
| 44 | 4-methyl-5-cyclopropyl-4H-1,2,4-triazol-3-yl | —S—(CH$_2$)$_3$— | tert.-butyl | cyclobutyl | 0.6 | 142 | 250 |
| 45 | 4,5-dimethyl-4H-1,2,4-triazol-3-yl | —S—(CH$_2$)$_3$— | tert.-butyl | cyclopropyl | 1.2 | 272 | 234 |
| 47 | 4-methyl-5-trifluoromethyl-4H-1,2,4-triazol-3-yl | —S—(CH$_2$)$_3$— | tert.-butyl | cyclopropyl | 1.9 | 484 | 253 |
| 52 | 2-hydroxy-pyrimidyl-4-yl | 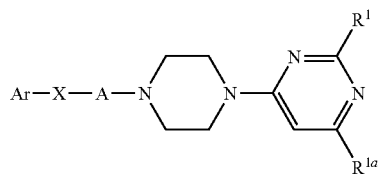 | tert.-butyl | cyclobutyl | 11.2 | 926 | 82 |
| 53 | 4-methyl-1,2,4-triazol-3-yl | —S—(CH$_2$)$_3$— | tert.-butyl | 1-methyl-cyclopropyl | 1.2 | 58 | 50 |
| 54 | 4,5-dimethyl-1,2,4-triazol-3-yl | —S—(CH$_2$)$_3$— | tert.-butyl | 1-methyl-cyclopropyl | 0.64 | 80 | 124 |
| 56 | 5-pyrazine-4-methyl-4H[1,2,4]triazol-4-yl | —S—(CH$_2$)$_3$— | tert.-butyl | cyclopropyl | 0.47 | 51.2 | 109 |
| 57 | 5-pyrazine-4-methyl-4H[1,2,4]triazol-4-yl | —S—(CH$_2$)$_3$— | cyclopropyl | tert.-butyl | 5.47 | 1607 | 296 |
| 63 | 4-methyl-5-phenyl-4H-[1,2,4]triazol-3-yl | —O—(CH$_2$)$_3$— | tert.-butyl | 1-methyl-cyclopropyl | 2.6 | 104 | 40 |
| 64 | 4-methyl-5-phenyl-4H-[1,2,4]triazol-3-yl | —O—(CH$_2$)$_3$— | tert.-butyl | cyclobutyl | 1.6 | 147 | 92 |
| 65 | 4-methyl-4H-[1,2,4]triazol-3-yl | —S—(CH$_2$)$_3$— | 1-methyl-cyclopropyl | CF$_3$ | 22.1 | 797 | 36 |
| 66 | 4-methyl-5-(1-methyl-1H-pyrrol-2-yl)-4H-[1,2,4]triazol-3-yl | —S—(CH$_2$)$_3$— | tert-butyl | cyclobutyl | 0.96 | 102 | 106 |

*Receptor binding constants obtained according to the assays as herein before described

We claim:

1. 4-piperazinylpyrimidine compounds of the formula I

wherein

Ar is phenyl or an aromatic 5- or 6-membered C-bound heteroaromatic radical, having 1 nitrogen atom as ring member and 0, 1, 2 or 3 further heteroatoms, independently of each other, selected from O, S and N, as ring members, wherein Ar may carry 1, 2 or 3 radicals $R^a$ which are, independently of each other, selected from the group consisting of $C_1$-$C_6$ alkyl, $C_3$-$C_6$ cycloalkyl, $C_1$-$C_4$ alkoxy-$C_1$-$C_4$-alkyl, $C_1$-$C_4$ haloalkyl, CN, NO$_2$, halogen, OR$^2$, NR$^3$R$^4$, C(O)NR$^3$R$^4$, O—C(O)NR$^3$R$^4$, SO$_2$NR$^3$R$^4$, COOR$^5$, SR$^6$, SOR$^6$, SO$_2$R$^6$, O—C(O)R$^7$, COR$^7$ or $C_3$-$C_5$ cycloalkylmethyl, wherein Ar may also carry a phenyl group or an aromatic 5- or 6-membered C-bound heteroaromatic radical, having 1 nitrogen atom as ring member and 0, 1, 2 or 3 further heteroatoms, independently of each other, selected from O, S and N, wherein the last two mentioned radicals may carry 1, 2, 3 or 4 of the aforementioned radicals $R^a$;

X is a single bond, CONR$^8$, S, or O;

A is linear $C_3$-$C_4$ alkylene, which may have a double bond or a triple bond and which also may carry 1 or 2 methyl groups;

$R^1$, $R^{1a}$ are independently from each other selected from $C_3$-$C_6$ alkyl, $C_1$-$C_2$-fluoroalkyl, or $C_3$-$C_6$ cycloalkyl, which may carry 1 or 2 $C_1$-$C_4$ alkyl groups, provided that at least one of the radicals $R^1$, $R^{1a}$ is selected from $C_3$-$C_4$ cycloalkyl optionally substituted with a $C_1$-$C_4$ alkyl group;

$R^2$, $R^3$, $R^4$, $R^5$, $R^6$, and $R^7$ independent of each other are H, $C_1$-$C_6$ alkyl, optionally substituted with OH, $C_1$-$C_4$ alkoxy or phenyl, $C_1$-$C_4$ haloalkyl or phenyl, which may carry 1, 2 or 3 radicals selected from the group consisting of $C_1$-$C_6$ alkyl, $C_1$-$C_6$ alkoxy, NR$^3$R$^4$, CN, $C_1$-$C_2$ fluoroalkyl oder halogen, R$^4$ may also be a radical COR$^9$, wherein R$^9$ is hydrogen, $C_1$-$C_6$ alkyl, $C_1$-$C_6$ alkoxy or phenyl, which may carry 1, 2 or 3 radicals selected from the group consisting of $C_1$-$C_6$ alkyl, $C_1$-$C_6$ alkoxy, NR$^3$R$^4$, CN, $C_1$-$C_2$ fluoroalkyl oder halogen, R$^3$ and R$^4$ may together with the nitrogen atom to which they are bound form a N-bound 5 or 6 membered saturated heterocycle, which may have an oxygen atom or an additional nitrogen atom as a ring member and which may carry 1, 2, 3 or 4 $C_1$-$C_6$ alkyl groups; and $R^8$ is hydrogen or $C_1$-$C_6$ alkyl;

their tautomers, enantiomers and diastereomers, and the physiologically tolerated acid addition salts of these compounds and the enantiomers, diastereomers and tautomers thereof.

2. The compounds as claimed in claim 1, wherein $R^{1a}$ is selected from the group consisting of cyclopropyl, cyclobutyl and 1-methylcyclopropyl.

3. The compounds as claimed in claim 1, wherein $R^a$ is selected from the group consisting of $NH_2$, OH, SH, $C_1$-$C_4$ alkyl, $C_3$-$C_5$ cycloalkyl, $C_1$-$C_4$ alkoxymethyl and trifluoromethyl.

4. The compounds as claimed in claim 1, wherein $R^1$ is tert.-butyl.

5. The compound as claimed in claim 1, wherein Ar is a radical of the formulae a to k

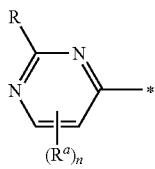
(a)

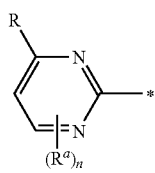
(b)

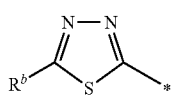
(c)

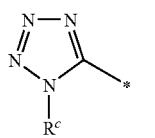
(d)

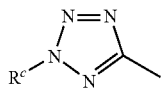
(e)

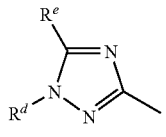
(f)

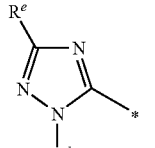
(g)

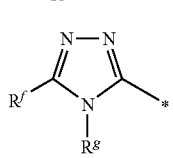
(h)

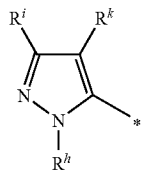
(i)

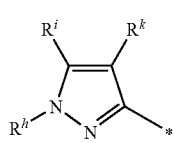
(k)

wherein the * indicates the position at which Ar is connected with X and wherein n in formulae a and b is 0 or 1 and $R^a$ is as defined for formula I;

$R^b$, $R^e$, $R^f$, $R^i$, $R^k$ are each independently hydrogen or a radical $R^a$, as defined above; and $R^c$, $R^d$, $R^g$, $R^h$ are each independently hydrogen, $C_1$-$C_4$ alkyl, $C_3$-$C_6$ cycloalkyl, $C_1$-$C_4$-alkoxymethyl or $C_1$-$C_2$ fluoroalkyl, R is hydrogen, OH or halogen.

6. The compound as claimed in claim 5 of the following formula Ia:

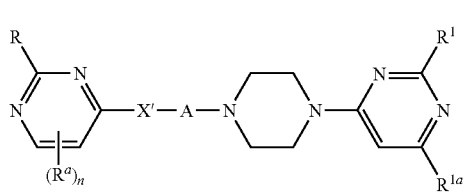
(Ia)

wherein $R^1$, $R^{1a}$ and $R^a$ are as defined in claim 1,

A is propane-1,3-diyl or 2-methylpropane-1,3-diyl n is 0 or 1;

R is hydrogen or hydroxyl; and

X' is $CH_2$, O or S;

the tautomers of Ia and the physiologically tolerated acid addition salts of these compounds and of the tautomers.

7. The compounds of the formula Ia as claimed in claim 6, selected from the group consisting of 2-tert-Butyl-4-cyclobutyl-6-{4-[3-(pyrimidin-4-yloxy) propyl]-piperazin-1-yl}pyrimidine;

4-{3-[4-(2-tert-Butyl-6-cyclobutylpyrimidin-4-yl)piperazin-1-yl]propoxy}pyrimidin-2-ol;

4-{3-[4-(2-tert-Butyl-6-cyclobutylpyrimidin-4-yl)piperazin-1-yl]butyl}pyrimidin-2-ol;

(R)-4-{3-[4-(2-tert-Butyl-6-cyclobutylpyrimidin-4-yl) piperazin-1-yl]-2-methylpropoxy}pyrimidin-2-ol;

(S)-4-{3-[4-(2-tert-Butyl-6-cyclobutylpyrimidin-4-yl) piperazin-1-yl]-2-methylpropoxy}pyrimidin-2-ol;

2-tert-Butyl-4-cyclopropyl-6-{4-[3-(pyrimidin-4-yloxy) propyl]-piperazin-1-yl}pyrimidine;

4-{3-[4-(2-tert-Butyl-6-cyclopropylpyrimidin-4-yl)piperazin-1-yl]propoxy}pyrimidin-2-ol;

4-{3-[4-(2-tert-Butyl-6-cyclopropylpyrimidin-4-yl)piperazin-1-yl]butyl}pyrimidin-2-ol;

(R)-4-{3-[4-(2-tert-Butyl-6-cyclopropylpyrimidin-4-yl) piperazin-1-yl]-2-methylpropoxy}pyrimidin-2-ol;

(S)-4-{3-[4-(2-tert-Butyl-6-cyclopropylpyrimidin-4-yl) piperazin-1-yl]-2-methylpropoxy}pyrimidin-2-ol;

their tautomers, enantiomers and diastereomers, and the physiologically tolerated acid addition salts of these compounds and the enantiomers, diastereomers and tautomers thereof.

8. The compound as claimed in claim 5 of the formula Ib:

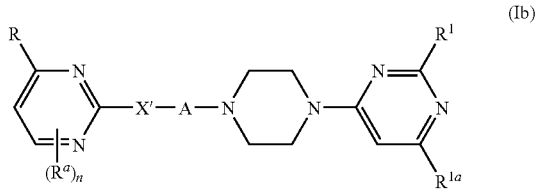

wherein $R^1$, $R^{1a}$ and $R^a$ are as defined in claim 1,
A is propane-1,3-diyl or 2-methylpropane-1,3-diyl
n is 0 or 1;
R is hydrogen, $C_1$-$C_4$ alkyl, or hydroxyl; and
X' is $CH_2$, O or S;
their tautomers, enantiomers and diastereomers, and the physiologically tolerated acid addition salts of these compounds and the enantiomers, diastereomers and tautomers thereof.

9. The compound of the formula Ib as claimed in claim 8, selected from the group consisting of
2-{3-[4-(2-tert-Butyl-6-cyclobutylpyrimidin-4-yl)piperazin-1-yl]propylsulfanyl}pyrimidin-4-ol fumarate,
2-tert-Butyl-4-cyclobutyl-6-{4-[3-(pyrimidin-2-ylsulfanyl)propyl]-piperazin-1-yl}pyrimidine,
2-tert-Butyl-4-cyclobutyl-6-{4-[3-(4-methylpyrimidin-2-ylsulfanyl)propyl]-piperazin-1-yl}pyrimidine,
2-{3-[4-(2-tert-Butyl-6-cyclobutylpyrimidin-4-yl)piperazin-1-yl]propoxy}pyrimidin-4-ol,
2-tert-Butyl-4-cyclobutyl-6-{4-[3-(pyrimidin-2-yloxy)propyl]-piperazin-1-yl}pyrimidine,
(R)-2-tert-Butyl-4-cyclobutyl-6-{4-[2-methyl-3-(pyrimidin-2-yloxy)propyl]-piperazin-1-yl}pyrimidine,
(S)-2-tert-Butyl-4-cyclobutyl-6-{4-[2-methyl-3-(pyrimidin-2-yloxy)propyl]-piperazin-1-yl}pyrimidine,
2-{4-[4-(2-tert-Butyl-6-cyclobutylpyrimidin-4-yl)piperazin-1-yl]butyl}pyrimidin-4-ol,
2-{3-[4-(2-tert-Butyl-6-cyclopropylpyrimidin-4-yl)piperazin-1-yl]propoxy}pyrimidin-4-ol,
2-{3-[4-(2-tert-Butyl-6-cyclopropylpyrimidin-4-yl)piperazin-1-yl]propylsulfanyl}pyrimidin-4-ol fumarate,
2-tert-Butyl-4-cyclopropyl-6-{4-[3-(pyrimidin-2-ylsulfanyl)propyl]-piperazin-1-yl}pyrimidine,
2-tert-Butyl-4-cyclopropyl-6-{4-[3-(4-methylpyrimidin-2-ylsulfanyl)propyl]-piperazin-1-yl}pyrimidine,
2-{3-[4-(2-tert-Butyl-6-cyclopropylpyrimidin-4-yl)piperazin-1-yl]propoxy}pyrimidin-4-ol,
2-tert-Butyl-4-cyclopropyl-6-{4-[3-(pyrimidin-2-yloxy)propyl]-piperazin-1-yl}pyrimidine,
(R)-2-tert-Butyl-4-cyclopropyl-6-{4-[2-methyl-3-(pyrimidin-2-yloxy)propyl]-piperazin-1-yl}pyrimidine,
(S)-2-tert-Butyl-4-cyclopropyl-6-{4-[2-methyl-3-(pyrimidin-2-yloxy)propyl]-piperazin-1-yl}pyrimidine,
2-{4-[4-(2-tert-Butyl-6-cyclopropylpyrimidin-4-yl)piperazin-1-yl]butyl}pyrimidin-4-ol,
2-{3-[4-(2-tert-Butyl-6-cyclopropylpyrimidin-4-yl)piperazin-1-yl]propoxy}pyrimidin-4-ol,
2-tert-Butyl-4-cyclopropyl-6-{4-[3-(pyrimidin-2-ylsulfanyl)propyl]-piperazin-1-yl}pyrimidine,
2-tert-Butyl-4-cyclobutyl-6-{4-[3-(5-fluoropyrimidin-2-ylsulfanyl)propyl]-piperazin-1-yl}pyrimidine,
2-tert-Butyl-4-cyclobutyl-6-{4-[3-(5-fluoropyrimidin-2-yloxy)propyl]-piperazin-1-yl}pyrimidine,
(R)-2-tert-Butyl-4-cyclobutyl-6-{4-[2-methyl-3-(5-fluoropyrimidin-2-yloxy)propyl]-piperazin-1-yl}pyrimidine,
(S)-2-tert-Butyl-4-cyclobutyl-6-{4-[2-methyl-3-(5-fluoropyrimidin-2-yloxy)propyl]-piperazin-1-yl}pyrimidine,
2-tert-Butyl-4-cyclopropyl-6-{4-[3-(5-fluoropyrimidin-2-ylsulfanyl)propyl]-piperazin-1-yl}pyrimidine,
2-tert-Butyl-4-cyclopropyl-6-{4-[3-(5-fluoropyrimidin-2-yloxy)propyl]-piperazin-1-yl}pyrimidine,
(R)-2-tert-Butyl-4-cyclopropyl-6-{4-[2-methyl-3-(5-fluoropyrimidin-2-yloxy)propyl]-piperazin-1-yl}pyrimidine,
(S)-2-tert-Butyl-4-cyclopropyl-6-{4-[2-methyl-3-(5-fluoropyrimidin-2-yloxy)propyl]-piperazin-1-yl}pyrimidine,
their tautomers, enantiomers and diastereomers, and the physiologically tolerated acid addition salts of these compounds and the enantiomers, diastereomers and tautomers thereof.

10. The compounds as claimed in claim 5 of the following formulae Ic to 1k:

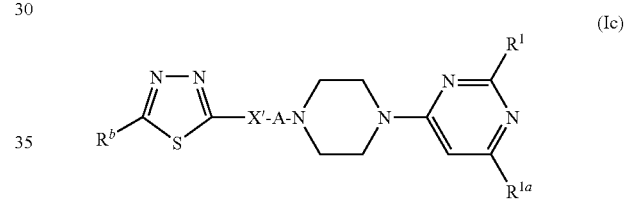

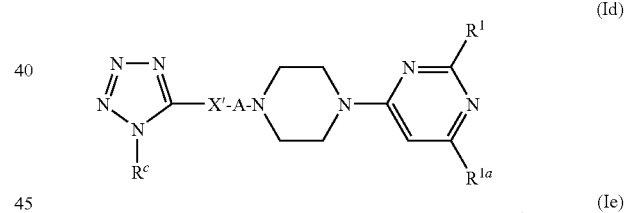

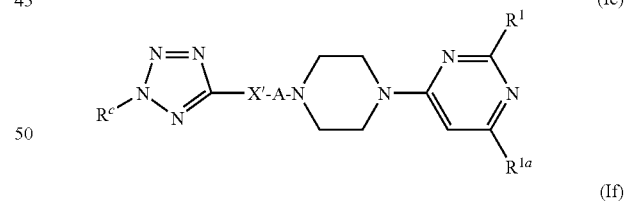

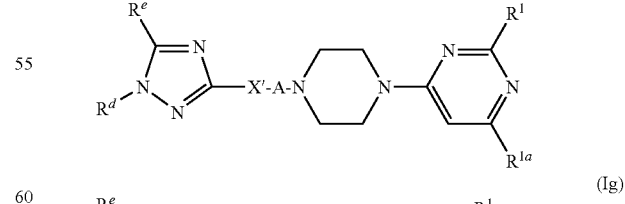

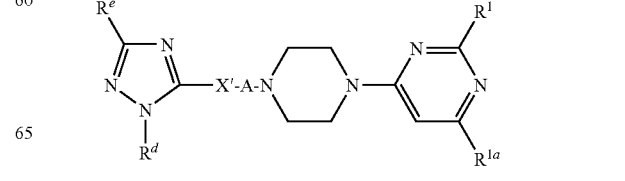

-continued

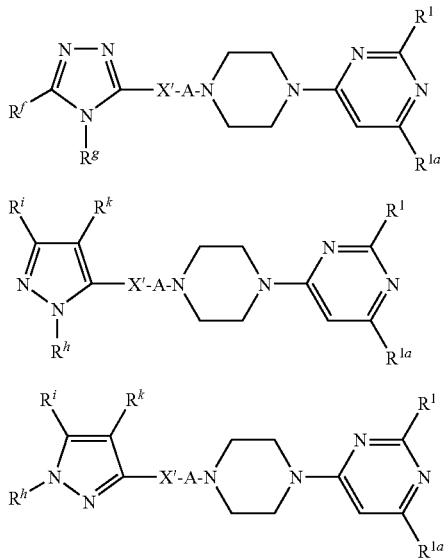

wherein $R^1$, $R^{1a}$, $R^b$, $R^c$, $R^d$, $R^e$, $R^f$, $R^g$, $R^h$, $R^i$ and $R^k$ are as defined above,
A is propane-1,3-diyl or 2-methylpropane-1,3-diyl; and
X' is $CH_2$, O or S
their tautomers, enantiomers and diastereomers, and the physiologically tolerated acid addition salts of these compounds and the enantiomers, diastereomers and tautomers thereof.

11. The compounds of the formula Ic as claimed in claim 10, selected from the group consisting of
2-tert-Butyl-4-{4-[3-(5-methyl-[1,3,4]-thiadiazol-2-ylsulfanyl)-propyl]-piperazin-1-yl}-6-cyclobutyl-pyrimidine,
2-tert-Butyl-4-{4-[3-(5-methyl-[1,3,4]-thiadiazol-2-ylsulfanyl)-propyl]-piperazin-1-yl}-6-cyclopropyl-pyrimidine,
2-tert-Butyl-4-{4-[3-(1,3,4-thiadiazol-2-ylsulfanyl)-propyl]-piperazin-1-yl}-6-cyclobutyl-pyrimidine,
2-tert-Butyl-4-{4-[3-(1,3,4-thiadiazol-2-ylsulfanyl)-propyl]-piperazin-1-yl}-6-cyclopropyl-pyrimidine,
2-tert-Butyl-4-{4-[3-(5-methyl-[1,3,4]-thiadiazol-2-yloxy)-propyl]-piperazin-1-yl}-6-cyclobutyl-pyrimidine,
2-tert-Butyl-4-{4-[3-(5-methyl-[1,3,4]-thiadiazol-2-yloxy)-propyl]-piperazin-1-yl}-6-cyclopropyl-pyrimidine,
2-tert-Butyl-4-{4-[3-(1,3,4-thiadiazol-2-yloxy)-propyl]-piperazin-1-yl}-6-cyclobutyl-pyrimidine,
2-tert-Butyl-4-{4-[3-(1,3,4-thiadiazol-2-yloxy)-propyl]-piperazin-1-yl}-6-cyclopropyl-pyrimidine,
their tautomers, enantiomers and diastereomers, and the physiologically tolerated acid addition salts of these compounds and the enantiomers, diastereomers and tautomers thereof.

12. The compounds of the formula Id as claimed in claim 10, selected from the group consisting of
2-tert-Butyl-4-{4-[3-(1-methyl-1H-tetrazol-5-ylsulfanyl)-propyl]-piperazin-1-yl}-6-cyclobutyl-pyrimidine,
2-tert-Butyl-4-{4-[3-(1-methyl-1H-tetrazol-5-ylsulfanyl)-propyl]-piperazin-1-yl}-6-cyclopropyl-pyrimidine,
2-tert-Butyl-4-{4-[3-(1-methyl-1H-tetrazol-5-yloxy)-propyl]-piperazin-1-yl}-6-cyclobutyl-pyrimidine,
2-tert-Butyl-4-{4-[3-(1-methyl-1H-tetrazol-5-yloxy)-propyl]-piperazin-1-yl}-6-cyclopropyl-pyrimidine,
their tautomers, enantiomers and diastereomers, and the physiologically tolerated acid addition salts of these compounds and the enantiomers, diastereomers and tautomers thereof.

13. The compounds of the formula Ie as claimed in claim 10, selected from the group consisting of
2-tert-Butyl-4-{4-[3-(2-methyl-2H-tetrazol-5-ylsulfanyl)-propyl]-piperazin-1-yl}-6-cyclobutyl-pyrimidine,
2-tert-Butyl-4-{4-[3-(2-methyl-2H-tetrazol-5-ylsulfanyl)-propyl]-piperazin-1-yl}-6-cyclopropyl-pyrimidine,
2-tert-Butyl-4-{4-[3-(2-methyl-2H-tetrazol-5-yloxy)-propyl]-piperazin-1-yl}-6-cyclobutyl-pyrimidine,
2-tert-Butyl-4-{4-[3-(2-methyl-2H-tetrazol-5-yloxy)-propyl]-piperazin-1-yl}-6-cyclopropyl-pyrimidine,
their tautomers, enantiomers and diastereomers, and the physiologically tolerated acid addition salts of these compounds and the enantiomers, diastereomers and tautomers thereof.

14. The compounds of the formula If as claimed in claim 10, selected from the group consisting of
2-tert-Butyl-4-{4-[3-(1-methyl-1H-[1,2,4]triazol-3-ylsulfanyl)-propyl]-piperazin-1-yl}-6-cyclopropyl-pyrimidine,
2-tert-Butyl-4-{4-[3-(1-methyl-1H-[1,2,4]triazol-3-ylsulfanyl)-propyl]-piperazin-1-yl}-6-cyclobutyl-pyrimidine,
2-tert-Butyl-4-{4-[3-(1-methyl-1H-[1,2,4]triazol-3-yloxy)-propyl]-piperazin-1-yl}-6-cyclobutyl-pyrimidine,
2-tert-Butyl-4-{4-[3-(1-methyl-1H-[1,2,4]triazol-3-yloxy)-propyl]-piperazin-1-yl}-6-cyclopropyl-pyrimidine,
2-tert-Butyl-4-cyclobutyl-6-{4-[3-(1H-[1,2,4]triazol-3-ylsulfanyl)-propyl]-piperazin-1-yl}-pyrimidine
their tautomers, enantiomers and diastereomers, and the physiologically tolerated acid addition salts of these compounds and the enantiomers, diastereomers and tautomers thereof.

15. The compounds of the formula Ig as claimed in claim 10, selected from the group consisting of
2-tert-Butyl-4-{4-[3-(2-methyl-2H-[1,2,4]triazol-3-ylsulfanyl)-propyl]-piperazin-1-yl}-6-cyclopropyl-pyrimidine,
2-tert-Butyl-4-{4-[3-(2-methyl-2H-[1,2,4]triazol-3-ylsulfanyl)-propyl]-piperazin-1-yl}-6-cyclobutyl-pyrimidine,
2-tert-Butyl-4-{4-[3-(2-methyl-2H-[1,2,4]triazol-3-yloxy)-propyl]-piperazin-1-yl}-6-cyclobutyl-pyrimidine,
2-tert-Butyl-4-{4-[3-(2-methyl-2H-[1,2,4]triazol-3-yloxy)-propyl]-piperazin-1-yl}-6-cyclopropyl-pyrimidine,
their tautomers, enantiomers and diastereomers, and the physiologically tolerated acid addition salts of these compounds and the enantiomers, diastereomers and tautomers thereof.

16. The compounds of the formula Ih as claimed in claim 10, selected from the group consisting of
2-tert-Butyl-4-{4-[3-(4-methyl-5-methyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-ethyl-4H-[1,2,4]triazol-3-ylsulfanyl)-propyl]-piperazin-1-yl}-6-cyclopropyl-pyrimidine, 2-tert-Butyl-4-{4-[3-(4-methyl-5-propyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-tert-butyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-trifluoromethyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-methyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-ethyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-propyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-tert-butyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-trifluoromethyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-5-methyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-ethyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-propyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-tert-butyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-trifluoromethyl-4H-[1,2,4]triazol-3-ylsulfanyl)-propyl]-piperazin-1-yl}-6-cyclobutyl-pyrimidine,
2-tert-Butyl-4-{4-[3-(4-methyl-4H-[1,2,4]triazol-3-ylsulfanyl)-propyl]-piperazin-1-yl}-6-(1-methylcyclobutyl)-pyrimidine,
2-tert-Butyl-4-{4-[3-(4-methyl-5-methyl-4H-[1,2,4]triazol-3-ylsulfanyl)-propyl]-piperazin-1-yl}-6-(1-methylcyclobutyl)-pyrimidine,
2-tert-Butyl-4-{4-[3-(4-methyl-5-trifluoromethyl-4H-[1,2,4]triazol-3-ylsulfanyl)-propyl]-piperazin-1-yl}-6-(1-methylcyclobutyl)-pyrimidine,
2-tert-Butyl-4-{4-[3-(4-methyl-4H-[1,2,4]triazol-3-ylsulfanyl)-propyl]-piperazin-1-yl}-6-cyclobutyl-pyrimidine,
2-tert-Butyl-4-{4-[3-(4-methyl-4H-[1,2,4]triazol-3-ylsulfanyl)-propyl]-piperazin-1-yl}-6-(1-methylcyclopropyl)-pyrimidine,
2-tert-Butyl-4-{4-[3-(4-methyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-cyclopropyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-cyclopropyl-4H-[1,2,4]triazol-3-ylsulfanyl)-propyl]-piperazin-1-yl}-6-cyclobutyl-pyrimidine,
2-tert-Butyl-4-{4-[3-(4-methyl-5-cyclobutyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-methoxymethyl-4H-[1,2,4]triazol-3-ylsulfanyl)-propyl]-piperazin-1-yl}-6-cyclopropyl-pyrimidine,
2-tert-Butyl-4-{4-[3-(4-methyl-5-methoxymethyl-4H-[1,2,4]triazol-3-ylsulfanyl)-propyl]-piperazin-1-yl}-6-cyclobutyl-pyrimidine,
2-tert-Butyl-4-{4-[3-(4H-[1,2,4]triazol-3-ylsulfanyl)-propyl]-piperazin-1-yl}-6-cyclobutyl-pyrimidine,
2-tert-butyl-4-{4-[3-(4-methyl-4H-[1,2,4]triazol-3-yloxy)-propyl]-piperazin-1-yl}-6-cyclobutyl-pyrimidine,
2-cyclopropyl-4-{4-[3-(4-methyl-4H-[1,2,4]triazol-3-ylsulfanyl)-propyl]-piperazin-1-yl}-6-tert-butyl-pyrimidine,
2-cyclopropyl-4-{4-[3-(4,5-dimethyl-4H-[1,2,4]triazol-3-ylsulfanyl)-propyl]-piperazin-1-yl}-6-tert-butyl-pyrimidine,
2-cyclobutyl-4-{4-[3-(4-methyl-4H-[1,2,4]triazol-3-ylsulfanyl)-propyl]-piperazin-1-yl}-6-tert-butyl-pyrimidine,
2-(1-methyl-cyclopropyl)-4-{4-[3-(4-methyl-4H-[1,2,4]triazol-3-ylsulfanyl)-propyl]-piperazin-1-yl}-6-tert-butyl-pyrimidine,
2-tert-butyl-4-{4-[3-(5-pyrazin-4-methyl-4H-[1,2,4]triazol-3-ylsulfanyl)-propyl]-piperazin-1-yl}-6-cyclopropyl-pyrimidine,
2-cyclopropyl-4-{4-[3-(5-pyrazin-4-methyl-4H-[1,2,4]triazol-3-ylsulfanyl)-propyl]-piperazin-1-yl}-6-tert-butyl-pyrimidine,
2-tert-butyl-4-{4-[3-(5-(pyrid-3-yl)-4-methyl-4H-[1,2,4]triazol-3-ylsulfanyl)-propyl]-piperazin-1-yl}-6-cyclopropyl-pyrimidine,
2-tert-butyl-4-{4-[3-(5-pyrazin-4-methyl-4H-[1,2,4]triazol-3-ylsulfanyl)-propyl]-piperazin-1-yl}-6-cyclopropyl-pyrimidine,
2-tert-butyl-4-{4-[3-(5-(1-methylpyrrol-2-yl)-4-methyl-4H-[1,2,4]triazol-3-ylsulfanyl)-propyl]-piperazin-1-yl}-6-cyclopropyl-pyrimidine,
2-cyclopropyl-4-{4-[3-(5-(pyrid-3-yl)-4-methyl-4H-[1,2,4]triazol-3-ylsulfanyl)-propyl]-piperazin-1-yl}-6-tert-butyl-pyrimidine,
2-tert-butyl-4-{4-[3-(5-phenyl-4-methyl-4H-[1,2,4]triazol-3-yloxy)-propyl]-piperazin-1-yl}-6-cyclopropyl-pyrimidine,
2-cyclopropyl-4-{4-[3-(5-phenyl-4-methyl-4H-[1,2,4]triazol-3-yloxy)-propyl]-piperazin-1-yl}-6-tert-butyl-pyrimidine,
2-tert-butyl-4-{4-[3-(5-(4-fluoro-phenyl)-4-methyl-4H-[1,2,4]triazol-3-yloxy)-propyl]-piperazin-1-yl}-6-cyclopropyl-pyrimidine,
2-tert-butyl-4-{4-[3-(5-pyrazin-4-methyl-4H-[1,2,4]triazol-3-yloxy)-propy-piperazin-1-yl}-6-cyclopropyl-pyrimidine,
2-cyclopropyl-4-{4-[3-(5-pyrazin-4-methyl-4H-[1,2,4]triazol-3-yloxy)-propyl]-piperazin-1-yl}-6-tert-butyl-pyrimidine,
2-cyclopropyl-4-{4-[3-(5-(1-methylpyrrol-2-yl)-4-methyl-4H-[1,2,4]triazol-3-ylsulfanyl)-propyl]-piperazin-1-yl}-6-tert-butyl-pyrimidine,
2-cyclopropyl-4-{4-[3-(5-(1-methylpyrrol-3-yl)-4-methyl-4H-[1,2,4]triazol-3-ylsulfanyl)-propyl]-piperazin-1-yl}-6-tert-butyl-pyrimidine,
2-tert-Butyl-4-(1-methyl-cyclopropyl)-6-{4-[3-(4-methyl-5-phenyl-4H-[1,2,4]triazol-3-yloxy)-propyl]-piperazin-1-yl}-pyrimidine, 2-tert-Butyl-4-cyclobutyl-6-{4-[3-(4-methyl-5-phenyl-4H-[1,2,4]triazol-3-yloxy)-propyl]-piperazin-1-yl}-pyrimidine, 2-(1-Methyl-cyclopropyl)-4-{4-[3-(4-methyl-4H-[1,2,4]triazol-3-ylsulfanyl)-propyl]-piperazin-1-yl}-6-trifluoromethyl-pyrimidine, 2-tert-Butyl-4-cyclobutyl-6-(4-{3-[4-methyl-5-(1-methyl-1H-pyrrol-2-yl)-4H-[1,2,4]triazol-3-ylsulfanyl]-propyl}-piperazin-1-yl)-pyrimidine, their tautomers, enantiomers and diastereomers, and the physiologically tolerated acid addition salts of these compounds and the enantiomers, diastereomers and tautomers thereof.

17. The compounds of the formula Ii as claimed in claim 10, selected from the group consisting of 2-tert-Butyl-4-{4-[3-(1,3-dimethyl-1H-pyrazol-5-ylsulfanyl)-propyl]-piperazin-1-yl}-6-cyclopropyl-pyrimidine, 2-tert-Butyl-4-{4-[3-(1,3-dimethyl-1H-pyrazol-5-ylsulfanyl)-propyl]-piperazin-1-yl}-6-cyclobutyl-pyrimidine, 2-tert-Butyl-4-{4-[3-(1,3-dimethyl-1H-pyrazol-5-yloxy)-propyl]-piperazin-1-yl}-6-cyclobutyl-pyrimidine, 2-tert-Butyl-4-{14-[3-(1,3-dimethyl-1H-pyrazol-5oxy)-propyl]-piperazin-1-yl}-6-cyclopropyl-pyrimidine, 2-tert-Butyl-4-{4-[3-(1-methyl-1H-pyrazol-5-ylsulfanyl)-propyl]-piperazin-1-yl}-6-cyclopropyl-pyrimidine, 2-tert-Butyl-4-{4-[3-(1-methyl-1H-pyrazol-5-ylsulfanyl)-propyl]-piperazin-1-yl}-6-cyclobutyl-pyrimidine, 2-tert-Butyl-4-{4-[3-(1-methyl-1H-pyrazol-5-yloxy)-propyl]-piperazin-1-yl}-6-cyclobutyl-pyrimidine, 2-tert-Butyl-4-{4-[3-(1-methyl-1H-pyrazol-5-yloxy)-propyl]-piperazin-1-yl}-6-cyclopropyl-pyrimidine, 2-tert-Butyl-4-{4-[3-(1-cyclopropyl-1H-pyrazol-5-ylsulfanyl)-propyl]-piperazin-1-yl}-6-cyclopropyl-pyrimidine, 2-tert-Butyl-4-{4-[3-(1-cyclopropyl-1H-pyrazol-5-ylsulfanyl)-propyl]-piperazin-1-yl}-6-cyclobutyl-pyrimidine, 2-tert-Butyl-4-{4-[3-(1-cyclopropyl-1H-pyrazol-5-yloxy)-propyl]-piperazin-1-yl}-6-cyclobutyl-pyrimidine, 2-tert-Butyl-4-{4-[3-(1-cyclopropyl-1H-pyrazol-5-yloxy)-propyl]-piperazin-1-yl}-6-cyclopropyl-pyrimidine, their tautomers, enantiomers and diastereomers, and the physiologically tolerated acid addition salts of these compounds and the enantiomers, diastereomers and tautomers thereof.

18. The compounds of the formula Ik as claimed in claim 10, selected from the group consisting of 2-tert-Butyl-4-{4-[3-(1-methyl-1H-pyrazol-3-ylsulfanyl)-propyl]-piperazin-1-yl}-6-cyclopropyl-pyrimidine, 2-tert-Butyl-4-{4-[3-(1-methyl-1H-pyrazol-3-ylsulfanyl)-propyl]-piperazin-1-yl}-6-cyclobutyl-pyrimidine, 2-tert-Butyl-4-{4-[3-(1-methyl-1H-pyrazol-3-yloxy)-propyl]-piperazin-1-yl}-6-cyclobutyl-pyrimidine, 2-tert-Butyl-4-{4-[3-(1-methyl-1H-pyrazol-3-yloxy)-propyl]-piperazin-1-yl}-6-cyclopropyl-pyrimidine, 2-tert-Butyl-4-{4-[3-(1-cyclopropyl-1H-pyrazol-3-ylsulfanyl)-propyl]-piperazin-1-yl}-6-cyclopropyl-pyrimidine, 2-tert-Butyl-4-{4-[3-(1-cyclopropyl-1H-pyrazol-3-ylsulfanyl)-propyl]-piperazin-1-yl}-6-cyclobutyl-pyrimidine, 2-tert-Butyl-4-{4-[3-(1-cyclopropyl-1H-pyrazol-3-yloxy)-propyl]-piperazin-1-yl}-6-cyclobutyl-pyrimidine, 2-tert-Butyl-4-{4-[3-(1-cyclopropyl-1H-pyrazol-3-yloxy)-propyl]-piperazin-1-yl}-6-cyclopropyl-pyrimidine, their tautomers, enantiomers and diastereomers, and the physiologically tolerated acid addition salts of these compounds and the enantiomers, diastereomers and tautomers thereof.

19. The compound as claimed in claim 1 of the following formula Im:

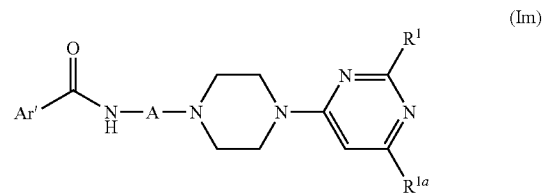

wherein $R^1$, $R^{1a}$ and A are as defined in claim 1, and Ar' is selected from phenyl, pyridyl, pyrimidinyl, pyrazinyl and pyridazinyl, wherein Ar' may carry 1, 2 or 3 of the aforementioned radicals $R^a$, their tautomers, enantiomers and diastereomers, and the physiologically tolerated acid addition salts of these compounds and the enantiomers, diastereomers and tautomers thereof.

20. The compounds of the formula Im as claimed in claim 19, selected from the group consisting of N-{4-[4-(2-tert-Butyl-6-cyclobutyl-pyrimidin-4-yl)-piperazin-1-yl]-butyl}-4-fluoro-benzamide N-{4-[4-(2-tert-Butyl-6-cyclobutyl-pyrimidin-4-yl)-piperazin-1-yl]-butyl}-2-fluoro-benzamide N-{4-[4-(2-tert-Butyl-6-cyclobutyl-pyrimidin-4-yl)-piperazin-1-yl]-butyl}-3-fluoro-benzamide N-{4-[4-(2-tert-Butyl-6-cyclobutyl-pyrimidin-4-yl)-piperazin-1-yl]-butyl}-2,4-difluoro-benzamide N-{4-[4-(2-tert-Butyl-6-cyclobutyl-pyrimidin-4-yl)-piperazin-1-yl]-butyl}-isonicotinamide N-{4-[4-(2-tert-Butyl-6-cyclobutyl-pyrimidin-4-yl)-piperazin-1-yl]-butyl}-nicotinamide Pyridine-2-carboxylic acid {4-[4-(2-tert-butyl-6-cyclobutyl-pyrimidin-4-yl)-piperazin-1-yl]-butyl}-amide Pyrazine-2-carboxylic acid {4-[4-(2-tert-butyl-6-cyclobutyl-pyrimidin-4-yl)-piperazin-1-yl]-butyl}-amide Pyrimidine-5-carboxylic acid {4-[4-(2-tert-butyl-6-cyclobutyl-pyrimidin-4-yl)-piperazin-1-yl]-butyl}-amide N-{4-[4-(2-tert-Butyl-6-cyclobutyl-pyrimidin-4-yl)-piperazin-1-yl]-butyl}-4-nitro-benzamide Pyridazine-4-carboxylic acid {4-[4-(2-tert-butyl-6-cyclobutyl-pyrimidin-4-yl)-piperazin-1-yl]-butyl}-amide N-{4-[4-(2-tert-Butyl-6-cyclobutyl-pyrimidin-4-yl)-piperazin-1-yl]-butyl}-4-fluoro-N-methyl-benzamide their tautomers, enantiomers and diastereomers, and the physiologically tolerated acid addition salts of these compounds and the enantiomers, diastereomers and tautomers thereof.

21. A pharmaceutical composition comprising at least one compound as claimed in claim 1, optionally together with at least one physiologically acceptable carrier or auxiliary substance.

22. A method for treating a medical disorder susceptible to treatment with a dopamine D3 receptor ligand, said method comprising administering an effective amount of at least one compound as claimed in claim 1 to a subject in need thereof, wherein the medical disorder is selected from the group consisting of diseases of Parkinson's disease, schizophrenia, depression, anxiety states, renal function disorders, and eating disorders.

23. A method for preparing a compound of the formula I as claimed in claim 1, wherein X is O or S, which comprises reacting a compound of the formula II

  (II)

wherein $R^x$ is SH or OH and Ar is as defined above, with a compound of the formula III

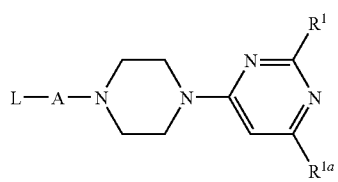  (III)

wherein A, $R^1$ and $R^{1a}$ are as defined above and L is a conventional leaving group, which is susceptible to nucleophilic replacement reaction.

24. A method for preparing a compound of the formula I as claimed in claim 1, which comprises reacting a compound of the formula IV

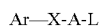  (IV)

wherein Ar, X and A are as defined above and L is a conventional leaving group, which is susceptible to nucleophilic replacement reaction, with a compound of the formula V

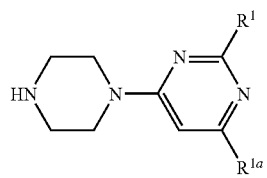  (V)

wherein A, $R^1$ and $R^{1a}$ are as defined above.

25. A method for preparing a compound of the formula I as claimed in claim 1, wherein X is a single bond and Ar is 4-hydroxypyrimidin-2-yl which comprises:

i) converting a compound of the formula IIIa into the amidinium compound VI:

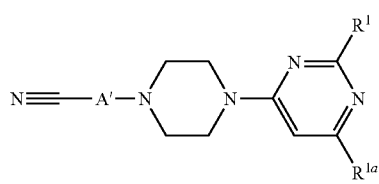  (IIIa)

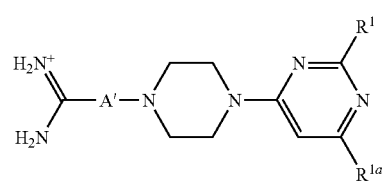  (VI)

wherein $R^1$ and $R^{1a}$ are as defined above and A' has the meanings given for A and ii) subsequently reacting the thus obtained hydroxamic ester with ammonia and reacting with an $C_1$-$C_4$-alkyl ester of 3-hydroxyacrylic acid.

26. A method for preparing a compound of the formula I as claimed in claim 1, wherein X is O, which comprises reacting a compound of the formula IIa:

  (IIa)

wherein L' is a leaving group, which is prone to undergo an aromatic substitution, and Ar is as defined above, with a compound of formula IIIb

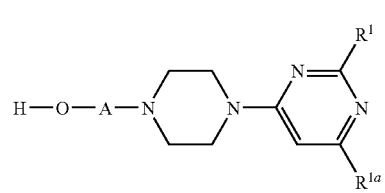  (IIIb)

wherein $R^1$ and $R^{1a}$ are as defined above.

27. A method for preparing a compound of the formula I as claimed in claim 1, wherein X is C(O)NH which comprises
i) reduction of a compound of the formula IIIa to obtain an amino compound of the formula IIIc:

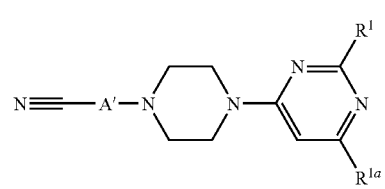  (IIIa)

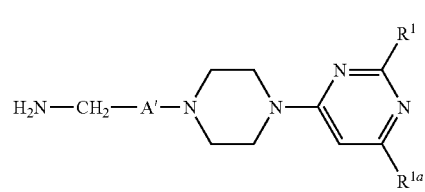  (IIIc)

wherein $R^1$ and $R^{1a}$ are as defined above and A' is ethan-1,2-diyl or propan-1,3-diyl, which may carry 1, or 2 alkyl groups, and ii) reacting the compound of formula IIIc with a compound of formula Ar—C(O)Hal or the corresponding acid Ar—C(O)OH, wherein Ar is as defined above and Hal is halogen, in an amidation reaction to obtain a compound of formula I with X being C(O)NH.

* * * * *